(12) United States Patent
Pingali et al.

(10) Patent No.: US 8,772,302 B2
(45) Date of Patent: Jul. 8, 2014

(54) GPR 119 AGONISTS

(75) Inventors: Harikishore Pingali, Ahmedabad (IN); Pandurang Zaware, Ahmedabad (IN); Mukul Jain, Ahmedabad (IN)

(73) Assignee: Cadila Healthcare Limited, Ahmedabad (IN)

( * ) Notice: Subject to any disclaimer, the term of this patent is extended or adjusted under 35 U.S.C. 154(b) by 223 days.

(21) Appl. No.: 13/377,995

(22) PCT Filed: Jun. 17, 2010

(86) PCT No.: PCT/IN2010/000418
§ 371 (c)(1),
(2), (4) Date: Jan. 25, 2012

(87) PCT Pub. No.: WO2010/146605
PCT Pub. Date: Dec. 23, 2010

(65) Prior Publication Data
US 2012/0122905 A1 May 17, 2012

(30) Foreign Application Priority Data
Jun. 18, 2009 (IN) .......................... 1458/MUM/2009

(51) Int. Cl.
*C07D 411/12* (2006.01)
*C07D 411/14* (2006.01)
*C07D 413/14* (2006.01)
*A61K 31/454* (2006.01)

(52) U.S. Cl.
USPC ........... 514/269; 514/275; 514/326; 544/319; 544/320; 544/321; 544/331; 546/207; 546/209; 546/210

(58) Field of Classification Search
USPC .......... 544/319, 320, 321, 331; 546/207, 209, 546/210; 514/269, 275, 326
See application file for complete search history.

(56) References Cited

FOREIGN PATENT DOCUMENTS

| WO | 2004065380 A1 | 8/2004 |
| WO | 2005007647 A1 | 1/2005 |
| WO | 2008083238 A2 | 7/2008 |
| WO | 2009038974 A1 | 3/2009 |

OTHER PUBLICATIONS

Overton et al., GPR119, a novel G protein-coupled receptor target for the treatment of type 2 diabetes and obesity, British Journal of Pharmacology (2008) 153, pp. S76-S81.*
Jones et al., GPR119 agonists for the treatment of type 2 diabetes, Exp. Opin. Ther. Patents (2009) 19(10): 1339-1359.*
Peterson et al., Expanding the scope of crystal form evaluation in pharmaceutical science, J Pharm Pharmaceut Sci (www.cspsCanada.org) 9(3): 317-326, 2006.*
Vippagunta, Crystalline Solids, Advanced Drug Delivery Reviews 48 (2001) pp. 3-26.*
European Patent Office, International Search Report, PCT/IN2010/000418, Nov. 4, 2010.
European Patent Office, International Preliminary Report on Patentability, PCT/IN2010/000418, Oct. 25, 2011.

* cited by examiner

*Primary Examiner* — Deepak Rao
(74) *Attorney, Agent, or Firm* — IpHorgan Ltd.

(57) ABSTRACT

The present invention relates to novel GPR 119 agonists of the general Formula (I), their pharmaceutically acceptable salts, pharmaceutically acceptable solvates, enantiomers, stereoisomers, and polymorphs. The invention also relates to processes for the preparation of the compounds of the invention, pharmaceutical compositions containing the compounds and to methods for treating one or both of diabetes and obesity using the compounds of the invention. The present invention is directed to G-protein coupled receptor (GPCR) agonists that are useful for the treatment of obesity, diabetes and related metabolic disorders.

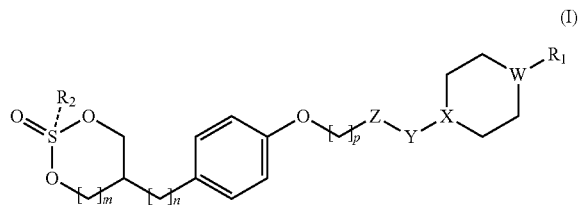

29 Claims, No Drawings

GPR 119 AGONISTS

FIELD OF THE INVENTION

The present invention relates to novel GPR 119 agonists of the general Formula (I), their pharmaceutically acceptable salts, pharmaceutically acceptable solvates, enantiomers, stereoisomers, and polymorphs. The invention also relates to processes for the preparation of the compounds of the invention, pharmaceutical compositions containing the compounds and to methods for treating one or both of diabetes and obesity using the compounds of the invention.

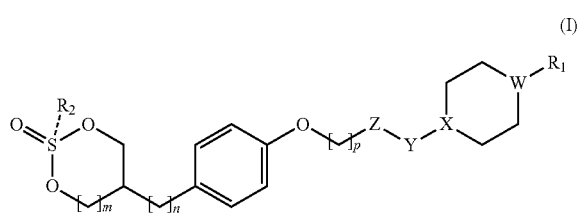

(I)

The present invention is directed to G-protein coupled receptor (GPCR) agonists that are useful for the treatment of obesity, diabetes and related metabolic disorders.

The compounds of the general Formula (I) lower blood glucose, regulate peripheral satiety, lower or modulate triglyceride levels and/or cholesterol levels and/or low-density lipoproteins (LDL) and raises the high-density lipoproteins (HDL) plasma levels and hence are useful in combating different medical conditions, where such lowering (and raising) is beneficial. Thus, it could be used in the treatment and/or prophylaxis of obesity, hyperlipidaemia, hypercholesteremia, hypertension, atherosclerotic disease events, vascular restenosis, diabetes and many other related conditions.

The compounds of general Formula (I) are useful to prevent or reduce the risk of developing atherosclerosis, which leads to diseases and conditions such as artereosclerotic cardiovascular diseases, stroke, coronary heart diseases, cerebrovascular diseases, peripheral vessel diseases and related disorders.

These compounds of general Formula (I) are useful for the treatment and/or prophylaxis of metabolic disorders loosely defined as Syndrome X. The characteristic features of Syndrome X include initial insulin resistance followed by hyperinsulinemia, dyslipidemia and impaired glucose tolerance. The glucose intolerance can lead to non-insulin dependent diabetes mellitus (NIDDM, Type 2 diabetes), which is characterized by hyperglycemia, which if not controlled may lead to diabetic complications or metabolic disorders caused by insulin resistance. Diabetes is no longer considered to be associated only with glucose metabolism, but it affects anatomical and physiological parameters, the intensity of which vary depending upon stages/duration and severity of the diabetic state. The compounds of this invention are also useful in prevention, halting or slowing progression or reducing the risk of the above mentioned disorders along with the resulting secondary diseases such as cardiovascular diseases, like arteriosclerosis, atherosclerosis; diabetic retinopathy, diabetic neuropathy and renal disease including diabetic nephropathy, glomerulonephritis, glomerular sclerosis, nephrotic syndrome, hypertensive nephrosclerosis and end stage renal diseases, like microalbuminuria and albuminuria, which may be result of hyperglycemia or hyperinsulinemia.

BACKGROUND OF THE INVENTION

Diabetes mellitus is a serious disease afflicting over 100 million people worldwide. In the United States, there are more than 12 million diabetics, with 600,000 new cases diagnosed each year.

Diabetes mellitus is a diagnostic term for a group of disorders characterized by abnormal glucose homeostasis resulting in elevated blood sugar. There are many types of diabetes, but the two most common are Type I (also referred to as insulin-dependent diabetes mellitus or IDDM) and Type II (also referred to as non-insulin-dependent diabetes mellitus or NIDDM).

The etiology of the different types of diabetes is not the same; however, everyone with diabetes has two things in common: overproduction of glucose by the liver and little or no ability to move glucose out of the blood into the cells where it becomes the body's primary fuel.

People who do not have diabetes rely on insulin, a hormone made in the pancreas, to move glucose from the blood into the cells of the body. However, people who have diabetes either don't produce insulin or can't efficiently use the insulin they produce; therefore, they can't move glucose into their cells. Glucose accumulates in the blood creating a condition called hyperglycemia, and over time, can cause serious health problems.

Diabetes is a syndrome with interrelated metabolic, vascular, and neuropathic components. The metabolic syndrome, generally characterized by hyperglycemia, comprises alterations in carbohydrate, fat and protein metabolism caused by absent or markedly reduced insulin secretion and/or ineffective insulin action. The vascular syndrome consists of abnormalities in the blood vessels leading to cardiovascular, retinal and renal complications. Abnormalities in the peripheral and autonomic nervous systems are also part of the diabetic syndrome.

About 5% to 10% of the people who have diabetes have IDDM. These individuals don't produce insulin and therefore must inject insulin to keep their blood glucose levels normal. IDDM is characterized by low or undetectable levels of endogenous insulin production caused by destruction of the insulin-producing 13 cells of the pancreas, the characteristic that most readily distinguishes IDDM from NIDDM. IDDM, once termed juvenile-onset diabetes, strikes young and older adults alike.

Approximately 90 to 95% of people with diabetes have Type II (or NIDDM). NIDDM subjects produce insulin, but the cells in their bodies are insulin resistant: the cells don't respond properly to the hormone, so glucose accumulates in their blood. NIDDM is characterized by a relative disparity between endogenous insulin production and insulin requirements, leading to elevated blood glucose levels. In contrast to IDDM, there is always some endogenous insulin production in NIDDM; many NIDDM patients have normal or even elevated blood insulin levels, while other NIDDM patients have inadequate insulin production (Rotwein, R. et al. N. Engl. J. Med. 308, 65-71 (1983)). Most people diagnosed with NIDDM are age 30 or older, and half of all new cases are age 55 and older. Compared with whites and Asians, NIDDM is more common among Native Americans, African-Americans, Latinos, and Hispanics. In addition, the onset can be insidious or even clinically non-apparent, making diagnosis difficult.

The primary pathogenic lesion on NIDDM has remained elusive. Many have suggested that primary insulin resistance of the peripheral tissues is the initial event. Genetic epidemiological studies have supported this view. Similarly, insulin secretion abnormalities have been argued as the primary defect in NIDDM. It is likely that both phenomena are important contributors to the disease process (Rimoin, D. L., et. al. Emery and Rimoin's Principles and Practice of Medical Genetics $3^{rd}$ Ed. 1:1401-1402 (1996)).

Many people with NIDDM have sedentary lifestyles and are obese; they weigh approximately 20% more than the recommended weight for their height and build. Furthermore, obesity is characterized by hyperinsulinemia and insulin resistance, a feature shared with NIDDM, hypertension and atherosclerosis.

Obesity and diabetes are among the most common human health problems in industrialized societies. In industrialized countries, a third of the population is at least 20% overweight. In the United States, the percentage of obese people has increased from 25% at the end of the 1970s, to 33% at the beginning the 1990s. Obesity is one of the most important risk factors for NIDDM. Definitions of obesity differ, but in general, a subject weighing at least 20% more than the recommended weight for his/her height and build is considered obese. The risk of developing NIDDM is tripled in subjects 30% overweight, and three-quarters with NIDDM are overweight.

Obesity, which is the result of an imbalance between caloric intake and energy expenditure, is highly correlated with insulin resistance and diabetes in experimental animals and human. However, the molecular mechanisms that are involved in obesity-diabetes syndromes are not clear. During early development of obesity, increase insulin secretion balances insulin resistance and protects patients from hyperglycemia (Le Stunff, et al. Diabetes 43, 696-702 (1989)). However, after several decades, β cell function deteriorates and non-insulin-dependent diabetes develops in about 20% of the obese population (Pederson, P. Diab. Metab. Rev. 5, 505-509 (1989)) and (Brancati, F. L., et al., Arch. Intern. Med. 159, 957-963 (1999)). Given its high prevalence in modern societies, obesity has thus become the leading risk factor for NIDDM (Hill, J. O., et al., Science 280, 1371-1374 (1998)). The present invention is directed to G-protein coupled receptor (GPCR) agonists. In particular, the present invention is directed to agonists of GPR 119 that are useful for the treatment of obesity, e.g. as regulators of satiety, and for the treatment of diabetes.

Obesity is characterized by an excessive adipose tissue mass relative to body size. Clinically, body fat mass is estimated by the body mass index (BMI; weight (kg)/height $(m)^2$), or waist circumference. Individuals are considered obese when the BMI is greater than 30 and there are established medical consequences of being overweight. It has been an accepted medical view for some time that an increased body weight, especially as a result of abdominal body fat, is associated with an increased risk for diabetes, hypertension, heart disease, and numerous other health complications, such as arthritis, stroke, gallbladder disease, muscular and respiratory problems, back pain and even certain cancers. However, the factors which predispose a fraction of patients to alteration of insulin secretion in response to fat accumulation remain unknown.

Pharmacological approaches to the treatment of obesity have been mainly concerned with reducing fat mass by altering the balance between energy intake and expenditure. Many studies have clearly established the link between adiposity and the brain circuitry involved in the regulation of energy homeostasis. Direct and indirect evidence suggest that serotonergic, dopaminergic, adrenergic, cholinergic, endocannabinoid, opioid, and histaminergic pathways in addition to many neuropeptide pathways (e.g. neuropeptide Y and melanocortins) are implicated in the central control of energy intake and expenditure. Hypothalamic centres are also able to sense peripheral hormones involved in the maintenance of body weight and degree of adiposity, such as insulin and leptin, and fat tissue derived peptides.

Drugs aimed at the pathophysiology associated with insulin dependent Type I diabetes and non-insulin dependent Type II diabetes have many potential side effects and do not adequately address the dyslipidaemia and hyperglycaemia in a high proportion of patients. Treatment is often focused at individual patient needs using diet, exercise, hypoglycaemic agents and insulin, but there is a continuing need for novel antidiabetic agents, particularly ones that may be better tolerated with fewer adverse effects.

Similarly, metabolic syndrome (syndrome X) which is characterized by hypertension and its associated pathologies including atherosclerosis, lipidemia, hyperlipidemia and hypercholesterolemia have been associated with decreased insulin sensitivity which can lead to abnormal blood sugar levels when challenged. Myocardial ischemia and microvascular disease is an established morbidity associated with untreated or poorly controlled metabolic syndrome.

There is a continuing need for novel antiobesity and antidiabetic agents, particularly ones that are well tolerated with few adverse effects.

The present invention is directed to G-protein coupled receptor agonists of GPR 119 that are useful for the treatment of obesity, e.g. as regulators of satiety, and for the treatment of diabetes. GPR 119 is a GPCR identified as SNORF25 in WO00/50562 which discloses both the human and rat receptors, U.S. Pat. No. 6,468,756 also discloses the mouse receptor (accession numbers: AAN95194 (human), AAN95195 (rat) and ANN95196 (mouse)).

In humans, GPR 119 is expressed in the pancreas, small intestine, colon and adipose tissue. A Role of G Protein-Coupled Receptor 119 expressed in β-Cell- in glycemic control by enhancing glucose dependent insulin release was demonstrated by using an agonist of GPR-119 (Endocrinology 148(6):2601-2609). Further the anti obesity effects of GPR-119 agonist which suppress food intake in rats and reduce body weight gain and white adipose tissue deposition upon subchronic oral administration to high-fat-fed rats was also demonstrated (Cell Metabolism 3, 167-175). GPR119 therefore represents a novel and attractive potential target for the therapy of obesity and related metabolic disorders.

International (PCT) Publication Nos. WO2005/061489; 2007116230; 2007116229; 2007003964; 2007003962; 2007003961; and 2006070208 disclose heterocyclic derivatives as GPR 119 receptor agonists. However, the therapeutic potential of these compounds to treat diseases has not yet been proved and so there remains the need to develop newer medicines which are better or of comparable efficacy with the present treatment regimes, have lesser side effects and require a lower dosage regime.

We herein disclose novel compounds of Formula (I) useful as antidiabetic, antiobesity, hypolipidaemic, hypolipoproteinemic, and antihyperglycemic agents which may have additional body weight lowering effect and beneficial effect in the treatment and/or prophylaxis of diseases caused by hyperlipidaemia, diseases classified under Syndrome X and atherosclerosis, and methods for their preparation.

SUMMARY OF THE INVENTION

In one aspect there are provided novel GPR 119 agonists represented by the general Formula (I),

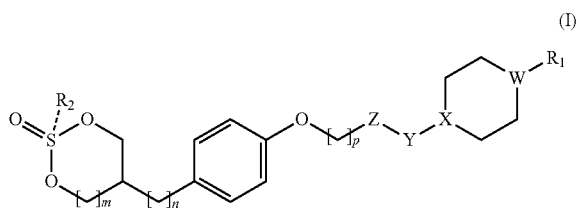

(I)

and their pharmaceutically acceptable salts, pharmaceutically acceptable solvates, enantiomers, stereoisomers, and polymorphs.

In another aspect of the invention there are provided processes for the preparation of compounds represented by the general Formula (I), and their pharmaceutically acceptable salts, pharmaceutically acceptable solvates, enantiomers, stereoisomers, and polymorphs.

In another aspect of the invention there are provided pharmaceutical compositions containing compounds of the general Formula (I), and their pharmaceutically acceptable salts, pharmaceutically acceptable solvates, enantiomers, stereoisomers, and polymorphs in combination with suitable carriers, excipients, or diluents or other media normally employed in preparing such compositions, which can be used for the treatment of one or both of diabetes and obesity.

The details of one or more embodiments of the inventions are set forth in the description below. Other features, objects and advantages of the inventions will be apparent from the description.

DETAILED DESCRIPTION OF THE INVENTION

Accordingly, the present invention relates to compounds of the general Formula (I),

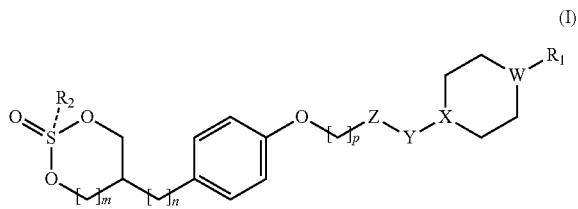

(I)

and their pharmaceutically acceptable salts, pharmaceutically acceptable solvates, enantiomers, stereoisomers, and polymorphs, and pharmaceutical compositions containing them wherein 'Z', may be present or absent & when present represents an optionally substituted single or fused group selected from aryl, heteroaryl, heterocyclyl, cycloalkyl groups;

$R_1$ represents optionally substituted groups selected from linear or branched $(C_1-C_6)$alkyl, aralkyl, cycloalkyl, cycloalkylalkyl, heterocyclyl, hererocyclylalkyl, aryl, heteroaryl, heteroaralkyl or the groups $C(O)OR_3$, $C(O)R_3$, and $SO_2R_3$ wherein $R_3$ represents optionally substituted groups selected from H, linear or branched $(C_1-C_6)$alkyl, aryl, aralkyl, cycloalkyl, cycloalkylalkyl, heterocyclyl, hererocyclylalkyl, heteroaryl, heteroaralkyl groups;

'Y' represents either a bond or groups selected from oxygen, —NH, S, SO, $SO_2$ or $NR_4$, wherein $R_4$ represents, linear or branched $(C_1-C_6)$alkyl;

'X' and 'W' may be same or different & independently represents C or N; 'm', 'n' and 'p' independently represents an integer ranging from 0 to 4; and $R_2$ may be optionally present and when present represents an oxo group;

In one embodiment there are provided compounds of Formula (I), wherein 'Z' is absent and all other symbols are as defined earlier.

In another embodiment there are provided compounds of Formula (I), wherein 'Z' represents optionally substituted single or fused group selected from aryl, heteroaryl, heterocyclyl, cycloalkyl groups and all other symbols are as defined earlier.

In another embodiment there are provided compounds of Formula (I), wherein 'Y' is a bond and all other symbols are as defined earlier.

In another embodiment there are provided compounds of Formula (I), wherein 'Y' is selected from oxygen, —NH, S, SO, $SO_2$ or $NR_4$, wherein $R_4$ represents, linear or branched $(C_1-C_6)$alkyl groups.

In a still further embodiment there are provided compounds of Formula (I), wherein 'Z' is absent, 'Y' represents a bond and all other symbols are as defined earlier. In another embodiment is provided compounds of formula (I) wherein 'Z' is absent, 'Y' is selected from oxygen, —NH, S, SO, $SO_2$ or $NR_4$, wherein $R_4$ represents, linear or branched $(C_1-C_6)$ alkyl groups.

In another embodiment there are provided compounds of Formula (I), wherein $R_1$ represents optionally substituted groups selected from linear or branched $(C_1-C_6)$alkyl, aralkyl, cycloalkyl, cycloalkylalkyl, heterocyclyl, hererocyclylalkyl, aryl, heteroaryl, heteroaralkyl groups and all other symbols are as defined earlier.

In a further embodiment there are provided compounds of Formula (I), wherein $R_1$ represents the groups $C(O)OR_3$, $C(O)R_3$, and $SO_2R_3$ wherein $R_3$ represents optionally substituted groups selected from H, linear or branched $(C_1-C_6)$ alkyl, aryl, aralkyl, cycloalkyl, cycloalkylalkyl, heterocyclyl, hererocyclylalkyl, heteroaryl, heteroaralkyl groups.

In an embodiment there are provided compounds of formula (I), wherein 'Z' is absent, $R_1$ represents optionally substituted groups selected from linear or branched $(C_1-C_6)$alkyl, aralkyl, cycloalkyl, cycloalkylalkyl, heterocyclyl, hererocyclylalkyl, aryl, heteroaryl, heteroaralkyl groups and all other symbols are as defined earlier.

In an embodiment there are provided compounds of Formula (I), wherein 'Z' is absent, $R_1$ represents the groups $C(O)OR_3$, $C(O)R_3$, and $SO_2R_3$ wherein $R_3$ represents optionally substituted groups selected from H, linear or branched $(C_1-C_6)$alkyl, aryl, aralkyl, cycloalkyl, cycloalkylalkyl, heterocyclyl, hererocyclylalkyl, heteroaryl, heteroaralkyl groups.

In another embodiment there are provided compounds of Formula (I), wherein 'Z' represents optionally substituted single or fused group selected from aryl, heteroaryl, heterocyclyl, cycloalkyl groups, and $R_1$ represents optionally substituted groups selected from linear or branched $(C_1-C_6)$alkyl, aralkyl, cycloalkyl, cycloalkylalkyl, heterocyclyl, hererocyclylalkyl, aryl, heteroaryl, heteroaralkyl groups and all other symbols are as defined earlier.

In another embodiment there are provided compounds of Formula (I), wherein 'Z' represents optionally substituted single or fused group selected from aryl, heteroaryl, heterocyclyl, cycloalkyl groups and $R_1$ represents the groups $C(O)OR_3$, $C(O)R_3$, and $SO_2R_3$ wherein $R_3$ represents optionally substituted groups selected from H, linear or branched $(C_1-C_6)$alkyl, aryl, aralkyl, cycloalkyl, cycloalkylalkyl, heterocyclyl, hererocyclylalkyl, heteroaryl, heteroaralkyl groups and all other symbols are as defined earlier.

In an embodiment there are provided compounds of Formula (I), wherein 'Z' is absent, 'Y' is a bond and $R_1$ represents optionally substituted groups selected from linear or branched $(C_1-C_6)$alkyl, aralkyl, cycloalkyl, cycloalkylalkyl, heterocyclyl, hererocyclylalkyl, aryl, heteroaryl, heteroaralkyl groups and all other symbols are as defined earlier.

In an embodiment there are provided compounds of Formula (I), wherein 'Z' is absent, 'Y' is a bond and $R_1$ represents the groups $C(O)OR_3$, $C(O)R_3$, and $SO_2R_3$ wherein $R_3$ represents optionally substituted groups selected from H, linear or branched $(C_1-C_6)$alkyl, aryl, aralkyl, cycloalkyl, cycloalkylalkyl, heterocyclyl, hererocyclylalkyl, heteroaryl, heteroaralkyl groups and all other symbols are as defined earlier.

In an embodiment there are provided compounds of Formula (I), wherein 'Z' is absent, 'Y' is selected from oxygen, —NH, S, SO, $SO_2$ or $NR_4$, wherein $R_4$ represents, linear or branched $(C_1-C_6)$alkyl groups and $R_1$ represents optionally substituted groups selected from linear or branched $(C_1-C_6)$ alkyl, aralkyl, cycloalkyl, cycloalkylalkyl, heterocyclyl, hererocyclylalkyl, aryl, heteroaryl, heteroaralkyl groups and all other symbols are as defined earlier.

In an embodiment there are provided compounds of Formula (I), wherein 'Z' is absent, 'Y' is selected from oxygen, —NH, S, SO, $SO_2$ or $NR_4$, wherein $R_4$ represents, linear or branched $(C_1-C_6)$alkyl groups and $R_1$ represents the groups $C(O)OR_3$, $C(O)R_3$, and $SO_2R_3$ wherein $R_3$ represents optionally substituted groups selected from H, linear or branched $(C_1-C_6)$alkyl, aryl, aralkyl, cycloalkyl, cycloalkylalkyl, heterocyclyl, hererocyclylalkyl, heteroaryl, heteroaralkyl groups and all other symbols are as defined earlier; In an embodiment is provided compounds of formula (I) wherein 'Y' is a bond and $R_1$ represents the groups $C(O)OR_3$, $C(O)R_3$, and $SO_2R_3$ wherein $R_3$ represents optionally substituted groups selected from H, linear or branched $(C_1-C_6)$alkyl, aryl, aralkyl, cycloalkyl, cycloalkylalkyl, heterocyclyl, hererocyclylalkyl, heteroaryl, heteroaralkyl groups and all other symbols are as defined earlier.

In an embodiment there are provided compounds of Formula (I), wherein 'Y' is selected from oxygen, —NH, S, SO, $SO_2$ or $NR_4$, wherein $R_4$ represents, linear or branched $(C_1-C_6)$alkyl groups and $R_1$ represents optionally substituted groups selected from linear or branched $(C_1-C_6)$alkyl, aralkyl, cycloalkyl, cycloalkylalkyl, heterocyclyl, hererocyclylalkyl, aryl, heteroaryl, heteroaralkyl groups and all other symbols are as defined earlier.

In another embodiment there are provided compounds of Formula (I), wherein 'Z' is selected from "heteroaryl group".

In another embodiment there are provided compounds of Formula (I), wherein 'Y' is selected from either a bond or oxygen atom.

In a further embodiment there are provided compounds of Formula (I), wherein $R_1$ is selected from the group representing $C(O)OR_3$ wherein $R_3$ is as defined earlier, or a heteroaryl group.

In still another embodiment there are provided compounds of Formula (I), wherein $R_3$ is selected from H linear or branched $(C_1-C_6)$alkyl, aryl, aralkyl group.

The substituents on 'Z' or '$R_1$' may be independently selected from hydroxyl, oxo, halo, thio, nitro, amino, cyano, formyl, or substituted or unsubstituted groups selected from amidino, alkyl, haloalkyl, alkoxy, haloalkoxy, alkenyl, alkynyl, cycloalkyl, cycloalkenyl, bicycloalkyl, bicycloalkenyl, alkoxy, alkenoxy, cycloalkoxy, aryl, aryloxy, aralkyl, aralkoxy, heterocyclyl, heteroaryl, heterocyclylalkyl, heteroaralkyl, heteroaryloxy, heteroaralkoxy, heterocyclyloxy, heterocyclylalkoxy, heterocyclylalkoxyacyl, acyl, acyloxy, acylamino, monosubstituted or disubstituted amino, arylamino, aralkylamino, carboxylic acid and its derivatives such as esters and amides, carbonylamino, hydroxyalkyl, aminoalkyl, alkoxyalkyl, aryloxyalkyl, aralkoxyalkyl, alkylthio, thioalkyl, arylthio, alkylsulfonylamino, alkylsulfonyloxy, alkoxycarbonylamino, aryloxycarbonylamino, aralkyloxycarbonylamino, aminocarbonylamino, alkylaminocarbonylamino, alkoxyamino, hydroxyl amino, sulfenyl derivatives, sulfonyl derivatives, sulfonic acid and its derivatives, each of these groups may independently be present one or more times either on 'Z' or '$R_1$'.

In another embodiment, the substituents on 'Z' or '$R_1$' may be independently selected from halo, thio, nitro, amino, cyano, or substituted or unsubstituted groups selected from alkyl, haloalkyl, alkoxy, haloalkoxy, aryl, aralkyl, sulfenyl derivatives, sulfonyl derivatives, sulfonic acid and its derivatives each of these groups may independently be present one or more times either on 'Z' or '$R_1$'.

In yet another embodiment, the alkyl groups may be selected from methyl, ethyl, n-propyl, iso-propyl, n-butyl, sec-butyl, tert-butyl, amyl, t-amyl, n-pentyl, n-hexyl, iso-hexyl groups; The aryl group may be an aromatic system containing one, two or three rings wherein such rings may be attached together in a dependant manner or may be fused; in a preferred embodiment such aryl group may be selected from phenyl, naphthyl, tetrahydronaphthyl, indane, biphenyl groups.

The heteroaryl group represents 5 to 8 membered aromatic radicals, which may be single or fused containing one or more hetero atoms selected from O, N or S; in a preferred embodiment such groups may be selected from pyridyl, thienyl, furyl, pyrrolyl, oxazolyl, thiazolyl, isothiazolyl, imidazolyl, isoxazolyl, oxadiazolyl, thiadiazolyl, triazolyl, tetrazolyl, benzopyranyl, benzopyranonyl, benzofuranyl, benzothienyl, indolinyl, indolyl, azaindolyl, azaindolinyl, benzodihydrofuranyl, benzodihydrothienyl, pyrazolopyrimidinyl, pyrazolopyrimidonyl, azaquinazolinyl, azaquinazolinoyl, pyridofuranyl, pyridothienyl, thienopyrimidyl, thienopyrimidonyl, quinolinyl, pyrimidinyl, pyrazolyl, quinazolinyl, quinazolonyl, pyrimidonyl, pyridazinyl, triazinyl, benzoxazinyl, benzoxazinonyl, benzothiazinyl, benzothiazinonyl, benzoxazolyl, benzothiazolyl, benzimidazolyl, benzotriazolyl, phthalazynil, naphthylidinyl, purinyl, carbazolyl, phenothiazinyl, phenoxazinyl groups.

The term "heterocyclyl" represents saturated, partially saturated or unsaturated ring-shaped radicals, the heteroatoms being selected from nitrogen, sulfur or oxygen; in a preferred embodiment such groups may be selected from aziridinyl, azetidinyl, pyrrolidinyl, imidazolidinyl, piperidinyl, piperazinyl, 2-oxopiperidinyl, 4-oxopiperidinyl, 2-oxopiperazinyl, 3-oxopiperazinyl, morpholinyl, thiomorpholinyl, 2-oxomorpholinyl, azepinyl, diazepinyl, oxapinyl, thiazepinyl, oxazolidinyl, thiazolidinyl, and the like; examples of partially saturated heterocyclic radicals include dihydrothiophene, dihydropyran, dihydrofuran, dihydrothiazole groups.

When the substituents on either of 'Z' or '$R_1$' are further substituted, those substituents may be independently selected from hydroxyl, oxo, halo, thio, nitro, amino, cyano, formyl, or substituted or unsubstituted groups selected from amidino, alkyl, haloalkyl, alkoxy, haloalkoxy, alkenyl, alkynyl, cycloalkyl, cycloalkenyl, bicycloalkyl, bicycloalkenyl, alkoxy, alkenoxy, cycloalkoxy, aryl, aryloxy, aralkyl, aralkoxy, heterocyclyl, heteroaryl, heterocyclylalkyl, heteroaralkyl, heteroaryloxy, heteroaralkoxy, heterocyclyloxy, heterocyclylalkoxy, heterocyclylalkoxyacyl, acyl, acyloxy, acylamino, monosubstituted or disubstituted amino, arylamino, aralkylamino, carboxylic acid and its derivatives such as esters and amides, carbonylamino, hydroxyalkyl, aminoalkyl, alkoxyalkyl, aryloxyalkyl, aralkoxyalkyl, alkylthio, thioalkyl, arylthio, alkylsulfonylamino, alkylsulfonyloxy, alkoxycarbonylamino, aryloxycarbonylamino, aralkyloxycarbonylamino, aminocarbonylamino, alkylaminocarbonylamino, alkoxyamino, hydroxyl amino, sulfenyl derivatives, sulfonyl derivatives, sulfonic acid and its derivatives.

The various groups, radicals and substituents used anywhere in the specification are further described in the following paragraphs:

- the "alkyl" group used either alone or in combination with other radicals, denotes a linear or branched radical containing one to six carbons, selected from methyl, ethyl, n-propyl, iso-propyl, n-butyl, sec-butyl, tert-butyl, amyl, t-amyl, n-pentyl, n-hexyl, and the like.
- the "alkenyl" group used either alone or in combination with other radicals, is selected from a radical containing from two to six carbons, more preferably groups selected from vinyl, allyl, 2-butenyl, 3-butenyl, 2-pentenyl, 3-pentenyl, 4-pentenyl, 2-hexenyl, 3-hexenyl, 4-hexenyl and the like; the "alkenyl" group includes dienes and trienes of straight and branched chains.
- the "alkynyl" group used either alone or in combination with other radicals, is selected from a linear or branched radical containing two to six carbon atoms, more preferably thynyl, 1-propynyl, 2-propynyl, 1-butynyl, 2-butynyl, 3-butynyl, 1-pentynyl, 2-pentynyl, 3-pentynyl, 4-pentynyl, 1-hexynyl, and the like. The term "alkynyl" includes di- and tri-ynes.
- the "cycloalkyl", or "alicyclic" group used either alone or in combination with other radicals, is selected from a cyclic radical containing three to six carbons, more preferably cyclopropyl, cyclobutyl, cyclopentyl, cyclohexyl and the like; The terms "bicycloalkyl" means more than one cycloalkyl groups fused together.
- the "cycloalkenyl" group used either alone or in combination with other radicals, are preferably selected from cyclopropenyl, 1-cyclobutenyl, 2-cyclobutenyl, 1-cyclopentenyl, 2-cyclopentenyl, 3-cyclopentenyl, 1-cyclohexenyl, 2-cyclohexenyl, 3-cyclohexenyl and the like.
- the "alkoxy" group used either alone or in combination with other radicals, is selected from groups containing an alkyl radical, as defined above, attached directly to an oxygen atom, more preferably groups selected from methoxy, ethoxy, n-propoxy, iso-propoxy, n-butoxy, t-butoxy, iso-butoxy, pentyloxy, hexyloxy, and the like.
- the "cycloalkoxy" group used either alone or in combination with other radicals, is selected from groups containing an cycloalkyl radical, as defined above, attached directly to an oxygen atom, more preferably groups selected from cyclopropoxy, cyclobutoxy, cyclopentyloxy, cyclohexyloxy, cycloheptyloxy and the like.
- the "aryloxy" group used either alone or in combination with other radicals, is selected from groups containing an aryl radical, as defined above, attached directly to an oxygen atom, more preferably groups selected from phenoxy, naphthyloxy, tetrahydronaphthyloxy, biphenyloxy, and the like.
- the "aralkyl" group used either alone or in combination with other radicals, is selected from groups containing an aryl radical, as defined above, attached directly to an alkyl radical, as define above, more preferably groups selected from benzyl, phenethyl, and the like.
- the "aralkoxy" group used either alone or in combination with other radicals, is selected from groups containing an aralkyl radical, as defined above, attached directly to an oxygen atom, more preferably groups selected from benzyloxy, phenethyloxy, and the like.
- the "heteroaralkyl" group used either alone or in combination with other radicals, is selected from groups containing an heteroaryl radical, as defined above, attached directly to an alkyl radicals, as defined above, more preferably groups selected from pyridinealkyl, thiophenealkyl, quinolinealkyl, and the like.
- the "alkenoxy" group used either alone or in combination with other radicals, is selected from groups containing an alkenyl radical, as defined above, attached to an oxygen atom, more preferably selected from vinyloxy, allyloxy, butenoxy, pentenoxy, hexenoxy, and the like.
- the "haloalkyl" group is selected from an alkyl radical, as defined above, suitably substituted with one or more halogens; such as perhaloalkyl, more preferably, perfluoro($C_1$-$C_6$)alkyl such as fluoromethyl, difluoromethyl, trifluoromethyl, fluoroethyl, difluoroethyl, trifluoroethyl, mono or polyhalo substituted methyl, ethyl, propyl, butyl, pentyl or hexyl groups.
- the "haloalkoxy" group is selected from suitable haloalkyl, as defined above, directly attached to an oxygen atom, more preferably groups selected from fluoromethoxy, chloromethoxy, fluoroethoxy, chloroethoxy and the like.
- the "perhaloalkoxy" group is selected from a suitable perhaloalkyl radical, as defined above, directly attached to an oxygen atom, more preferably groups selected from trifluoromethoxy, trifluoroethoxy, and the like.
- the groups "heteroaryloxy", "heteroaralkoxy", "heterocycloxy", "heterocylylalkoxy" are selected from suitable heteroaryl, heteroarylalkyl, heterocyclyl, heterocylylalkyl groups respectively, as defined above, attached to an oxygen atom.
- the "acyl" group used either alone or in combination with other radicals, is selected from a radical containing one to eight carbons, more preferably selected from formyl, acetyl, propanoyl, butanoyl, iso-butanoyl, pentanoyl, hexanoyl, heptanoyl, benzoyl and the like, which may be substituted.
- the "acyloxy" group used either alone or in combination with other radicals, is selected from a suitable acyl group, as defined above, directly attached to an oxygen atom, more preferably such groups are selected from acetyloxy, propionyloxy, butanoyloxy, iso-butanoyloxy, benzoyloxy and the like.
- the "acylamino" group used either alone or in combination with other radicals, is selected from a suitable acyl group as defined earlier, attached to an amino radical, more preferably such groups are selected from $CH_3CONH$, $C_2H_5CONH$, $C_3H_7CONH$, $C_4H_9CONH$, $C_6H_5CONH$ and the like, which may be substituted.
- the "mono-substituted amino" group used either alone or in combination with other radicals, represents an amino group substituted with one group selected from ($C_1$-$C_6$) alkyl, substituted alkyl, aryl, substituted aryl or arylalkyl groups as defined earlier, more preferably such groups are selected from methylamine, ethylamine, n-propylamine, n-butylamine, n-pentylamine and the like.
- the "disubstituted amino" group used either alone or in combination with other radicals, represents an amino group, substituted with two radicals that may be same or different selected from ($C_1$-$C_6$)alkyl, substituted alkyl, aryl, substituted aryl, or arylalkyl groups, as defined above, more preferably the groups are selected from dimethylamino, methylethylamino, diethylamino, phenylmethyl amino and the like.

the "arylamino" used either alone or in combination with other radicals, represents an aryl group, as defined above, linked through amino having a free valence bond from the nitrogen atom, more preferably the groups are selected from phenylamino, naphthylamino, N-methyl anilino and the like.

the "oxo" or "carbonyl" group used either alone (—C=O—) or in combination with other radicals such as alkyl described above, for e.g. "alkylcarbonyl", denotes a carbonyl radical (—C=O—) substituted with an alkyl radical described above such as acyl or alkanoyl.

the "carboxylic acid" group, used alone or in combination with other radicals, denotes a —COOH group, and includes derivatives of carboxylic acid such as esters and amides.

the "ester" group used alone or in combination with other radicals, denotes —COO-group, and includes carboxylic acid derivatives, more preferably the ester moieties are selected from alkoxycarbonyl, such as methoxycarbonyl, ethoxycarbonyl, and the like, which may optionally be substituted; aryloxycarbonyl group such as phenoxycarbonyl, napthyloxycarbonyl, and the like, which may optionally be substituted; aralkoxycarbonyl group such as benzyloxycarbonyl, phenethyloxycarbonyl, napthylmethoxycarbonyl, and the like, which may optionally be substituted; heteroaryloxycarbonyl, heteroaralkoxycarbonyl, wherein the heteroaryl group, is as defined above, which may optionally be substituted; heterocyclyloxycarbonyl, where the heterocyclic group, as defined earlier, which may optionally be substituted.

the "amide" group used alone or in combination with other radicals, represents an aminocarbonyl radical ($H_2N$—C=O), wherein the amino group is mono- or di-substituted or unsubstituted, more preferably the groups are selected from methyl amide, dimethyl amide, ethyl amide, diethyl amide, and the like.

the "aminocarbonyl" group used either alone or in combination with other radicals, may be selected from 'aminocarbonyl', "aminocarbonylalkyl", "n-alkylaminocarbonyl", "N-arylaminocarbonyl", "N,N-dialkylaminocarbonyl", "N-alkyl-N-arylaminocarbonyl", "N-alkyl-N-hydroxyaminocarbonyl", and "N-alkyl-N-hydroxyaminocarbonylalkyl", each of them being optionally substituted. The terms "N-alkylaminocabonyl" and "N,N-dialkylaminocarbonyl" denotes aminocarbonyl radicals, as defined above, which have been substituted with one alkyl radical and with two alkyl radicals, respectively. Preferred are "lower alkylaminocarbonyl" having lower alkyl radicals as described above attached to aminocarbonyl radical. The terms "N-arylaminocarbonyl" and "N-alkyl-N-arylaminocarbonyl" denote aminocarbonyl radicals substituted, respectively, with one aryl radical, or one alkyl, and one aryl radical. The term "aminocarbonylalkyl" includes alkyl radicals substituted with aminocarbonyl radicals.

the "hydroxyalkyl" group used either alone or in combination with other radicals, is selected from an alkyl group, as defined above, substituted with one or more hydroxy radicals, more preferably the groups are selected from hydroxymethyl, hydroxyethyl, hydroxypropyl, hydroxybutyl, hydroxypentyl, hydroxyhexyl and the like.

the "aminoalkyl" group used alone or in combination with other radicals, denotes an amino (—$NH_2$) moiety attached to an alkyl radical, as defined above, which may be substituted, such as mono- and di-substituted aminoalkyl. The term "alkylamino" used herein, alone or in combination with other radicals, denotes an alkyl radical, as defined above, attached to an amino group, which may be substituted, such as mono- and di-substituted alkylamino.

the "alkoxyalkyl" group used alone or in combination with other radicals, denotes an alkoxy group, as defined above, attached to an alkyl group as defined above, more preferably the groups may be selected from methoxymethyl, ethoxymethyl, methoxyethyl, ethoxyethyl and the like.

the "alkylthio" group used either alone or in combination with other radicals, denotes a straight or branched or cyclic monovalent substituent comprising an alkyl group as defined above, linked through a divalent sulfur atom having a free valence bond from the sulfur atom, more preferably the groups may be selected from methylthio, ethylthio, propylthio, butylthio, pentylthio and the like or cyclic alkylthio selected from cyclopropylthio, cyclobutylthio, cyclopentylthio, cyclohexylthio and the like, which may be optionally substituted.

the "thioalkyl" group used either alone or in combination with other radicals, denotes an alkyl group, as defined above, attached to a group of formula —SR', where R' represents, alkyl or aryl group, e.g. thiomethyl, methylthiomethyl, phenylthiomethyl and the like, which may be optionally substituted.

the "alkoxycarbonylamino" group used alone or in combination with other radicals, is selected from a suitable alkoxycarbonyl group, as defined above, attached to an amino group, more preferably methoxycarbonylamino, ethoxycarbonylamino, and the like.

the "aminocarbonylamino", "alkylaminocarbonylamino", "dialkylaminocarbonylamino" groups used alone or in combination with other radicals, is a carbonylamino (—$CONH_2$) group, attached to amino($NH_2$), alkylamino group or dialkylamino group respectively, where alkyl group is as defined above;

the "amidino" group used either alone or in combination with other radicals, represents a —C(=NH)—$NH_2$ radical; the "alkylamidino" group represents an alkyl radical, as described above, attached to an amidino group.

the "alkoxyamino" group used alone or in combination with other radicals, represents a suitable alkoxy group as defined above, attached to an amino group;

the "hydroxyamino" group used either alone or in combination with other radicals, represents a —NHOH moiety, and may be optionally substituted with suitable groups selected from those described above.

the "sulfenyl" group or "sulfenyl derivatives" used alone or in combination with other radicals, represents a bivalent group, —SO— or $R_x$SO, where $R_x$ is an optionally substituted alkyl, aryl, heteroaryl, heterocyclyl, group selected from those described above.

the "sulfonyl" group or "sulfones derivatives" used either alone or in combination with other radicals, with other terms such as alkylsulfonyl, represents a divalent radical —$SO_2$—, or $R_xSO_2$—, where $R_x$ is as defined above. More preferably, the groups may be selected from "alkylsulfonyl" wherein suitable alkyl radicals, selected from those defined above, is attached to a sulfonyl radical, such as methylsulfonyl, ethylsulfonyl, propylsulfonyl and the like, "arylsulfonyl" wherein an aryl radical, as defined above, is attached to a sulfonyl radical, such as phenylsulfonyl and the like.

the "sulfonyloxy" group used either alone or in combination with other radicals, with other terms such as alkylsulfonyloxy, represents a divalent radical —SO$_3$—, or R$_x$SO$_3$—, where R$_x$ is as defined above. More preferably, the groups may be selected from "alkylsulfonyl" wherein suitable alkyl radicals, selected from those defined above, is attached to a sulfonyloxy radical, such as methanesulfonyloxy, ethanesulfonyloxy, propanesulfonyloxy and the like, "arylsulfonyl" wherein an aryl radical, as defined above, is attached to a sulfonyl radical, such as benzenesulfonyloxy and the like.

Suitable groups and substituents on the groups may be selected from those described anywhere in the specification.

In another aspect there are provided compounds selected from:

cis-5-(4-((6-(4-(3-isopropyl-1,2,4-oxadiazol-5-yl)piperidin-1-yl)-5-nitropyrimidin-4-yl)oxy)phenyl)-1,3,2-dioxathiane 2-oxide;

trans-5-(4-((6-(4-(3-isopropyl-1,2,4-oxadiazol-5-yl)piperidin-1-yl)-5-nitropyrimidin-4-yl)oxy)phenyl)-1,3,2-dioxathiane 2-oxide;

cis-5-(4-((6-((1-(3-isopropyl-1,2,4-oxadiazol-5-yl)piperidin-4-yl)oxy)-5-methylpyrimidin-4-yl)oxy)phenyl)-1,3,2-dioxathiane 2-oxide;

trans-5-(4-((6-((1-(3-isopropyl-1,2,4-oxadiazol-5-yl)piperidin-4-yl)oxy)-5-methylpyrimidin-4-yl)oxy)phenyl)-1,3,2-dioxathiane 2-oxide;

cis-5-(4-((5-methyl-6-((1-(pyrimidin-2-yl)piperidin-4-yl)oxy)pyrimidin-4-yl)oxy)phenyl)-1,3,2-dioxathiane 2-oxide;

trans-5-(4-((5-methyl-6-((1-(pyrimidin-2-yl)piperidin-4-yl)oxy)pyrimidin-4-yl)oxy)phenyl)-1,3,2-dioxathiane 2-oxide;

cis-5-(4-((2-(1-(pyrimidin-2-yl)piperidin-4-yl)thiazol-4-yl)methoxy)phenyl)-1,3,2-dioxathiane 2-oxide;

trans-5-(4-((2-(1-(pyrimidin-2-yl)piperidin-4-yl)thiazol-4-yl)methoxy)phenyl)-1,3,2-dioxathiane 2-oxide;

cis-5-(4-((6-((1-(5-ethylpyrimidin-2-yl)piperidin-4-yl)oxy)-5-methylpyrimidin-4-yl)oxy)phenyl)-1,3,2-dioxathiane 2-oxide;

trans-5-(4-((6-((1-(5-ethylpyrimidin-2-yl)piperidin-4-yl)oxy)-5-methylpyrimidin-4-yl)oxy)phenyl)-1,3,2-dioxathiane 2-oxide;

cis-5-(4-((6-(4-(3-isopropyl-1,2,4-oxadiazol-5-yl)piperidin-1-yl)-5-methylpyrimidin-4-yl)oxy)phenyl)-1,3,2-dioxathiane 2-oxide;

trans-5-(4-((6-(4-(3-isopropyl-1,2,4-oxadiazol-5-yl)piperidin-1-yl)-5-methylpyrimidin-4-yl)oxy)phenyl)-1,3,2-dioxathiane 2-oxide;

cis-5-(4-((2-(1-(5-ethylpyrimidin-2-yl)piperidin-4-yl)thiazol-4-yl)methoxy)phenyl)-1,3,2-dioxathiane 2-oxide;

trans-5-(4-((2-(1-(5-ethylpyrimidin-2-yl)piperidin-4-yl)thiazol-4-yl)methoxy)phenyl)-1,3,2-dioxathiane 2-oxide;

cis-tert-butyl 4-((5-methyl-6-(4-(2-oxido-1,3,2-dioxathian-5-yl)phenoxy)pyrimidin-4-yl)oxy)piperidine-1-carboxylate;

trans-tert-butyl 4-((5-methyl-6-(4-(2-oxido-1,3,2-dioxathian-5-yl)phenoxy)pyrimidin-4-yl)oxy)piperidine-1-carboxylate;

cis-tert-butyl 4-(4-((4-(2-oxido-1,3,2-dioxathian-5-yl)phenoxy)methyl)thiazol-2-yl)piperidine-1-carboxylate;

trans-tert-butyl 4-(4-((4-(2-oxido-1,3,2-dioxathian-5-yl)phenoxy)methyl)thiazol-2-yl)piperidine-1-carboxylate;

trans-tert-butyl 4-(2-(4-(2-oxido-1,3,2-dioxathian-5-yl)phenoxy)ethoxy)piperidine-1-carboxylate;

cis-tert-butyl 4-(3-((5-methyl-6-(4-(2-oxido-1,3,2-dioxathian-5-yl)phenoxy)pyrimidin-4-yl)oxy)propyl)piperidine-1-carboxylate;

trans-tert-butyl 4-(3-((5-methyl-6-(4-(2-oxido-1,3,2-dioxathian-5-yl)phenoxy)pyrimidin-4-yl)oxy)propyl)piperidine-1-carboxylate;

cis-5-(4-(3-((1-(pyrimidin-2-yl)piperidin-4-yl)oxy)propoxy)phenyl)-1,3,2-dioxathiane 2-oxide;

trans-5-(4-(3-((1-(pyrimidin-2-yl)piperidin-4-yl)oxy)propoxy)phenyl)-1,3,2-dioxathiane 2-oxide;

cis-tert-butyl 4-((5-methyl-6-(4-((2-oxido-1,3,2-dioxathian-5-yl)methyl)phenoxy)pyrimidin-4-yl)oxy)piperidine-1-carboxylate;

trans-tert-butyl 4-((5-methyl-6-(4-((2-oxido-1,3,2-dioxathian-5-yl)methyl)phenoxy)pyrimidin-4-yl)oxy)piperidine-1-carboxylate;

tert-butyl 4-((5-methyl-6-(4-((2-oxido-1,3,2-dioxathiolan-4-yl)methyl)phenoxy)pyrimidin-4-yl)oxy)piperidine-1-carboxylate.

cis-isobutyl 4-((5-methyl-6-(4-(2-oxido-1,3,2-dioxathian-5-yl)phenoxy)pyrimidin-4-yl)oxy)piperidine-1-carboxylate;

trans-isobutyl 4-((5-methyl-6-(4-(2-oxido-1,3,2-dioxathian-5-yl)phenoxy)pyrimidin-4-yl)oxy)piperidine-1-carboxylate;

cis-5-(4-((6-((1-(3-isopropyl-1,2,4-oxadiazol-5-yl)piperidin-4-yl)oxy)-5-methylpyrimidin-4-yl)oxy)benzyl)-1,3,2-dioxathiane 2-oxide;

trans-5-(4-((6-((1-(3-isopropyl-1,2,4-oxadiazol-5-yl)piperidin-4-yl)oxy)-5-methylpyrimidin-4-yl)oxy)benzyl)-1,3,2-dioxathiane 2-oxide;

cis-5-(4-((6-((1-(5-ethylpyrimidin-2-yl)piperidin-4-yl)oxy)-5-methylpyrimidin-4-yl)oxy)benzyl)-1,3,2-dioxathiane 2-oxide;

trans-5-(4-((6-((1-(5-ethylpyrimidin-2-yl)piperidin-4-yl)oxy)-5-methylpyrimidin-4-yl)oxy)benzyl)-1,3,2-dioxathiane 2-oxide;

cis-ethyl 4-((5-methyl-6-(4-(2-oxido-1,3,2-dioxathian-5-yl)phenoxy)pyrimidin-4-yl)oxy)piperidine-1-carboxylate;

trans-ethyl 4-((5-methyl-6-(4-(2-oxido-1,3,2-dioxathian-5-yl)phenoxy)pyrimidin-4-yl)oxy)piperidine-1-carboxylate;

cis-benzyl 4-((5-methyl-6-(4-(2-oxido-1,3,2-dioxathian-5-yl)phenoxy)pyrimidin-4-yl)oxy)piperidine-1-carboxylate;

trans-benzyl 4-((5-methyl-6-(4-(2-oxido-1,3,2-dioxathian-5-yl)phenoxy)pyrimidin-4-yl)oxy)piperidine-1-carboxylate;

cis-5-(4-((6-((1-benzylpiperidin-4-yl)oxy)-5-methylpyrimidin-4-yl)oxy)phenyl)-1,3,2-dioxathiane 2-oxide;

trans-5-(4-((6-((1-benzylpiperidin-4-yl)oxy)-5-methylpyrimidin-4-yl)oxy)phenyl)-1,3,2-dioxathiane 2-oxide;

cis-ethyl 4-((5-methyl-6-(4-((2-oxido-1,3,2-dioxathian-5-yl)methyl)phenoxy)pyrimidin-4-yl)oxy)piperidine-1-carboxylate;

trans-ethyl 4-((5-methyl-6-(4-((2-oxido-1,3,2-dioxathian-5-yl)methyl)phenoxy)pyrimidin-4-yl)oxy)piperidine-1-carboxylate;

cis-5-(4-((5-methyl-6-((1-(pyrimidin-2-yl)piperidin-4-yl)oxy)pyrimidin-4-yl)oxy)benzyl)-1,3,2-dioxathiane 2-oxide;

trans-5-(4-((5-methyl-6-((1-(pyrimidin-2-yl)piperidin-4-yl)oxy)pyrimidin-4-yl)oxy)benzyl)-1,3,2-dioxathiane 2-oxide;

cis-isobutyl 4-((5-methyl-6-(4-((2-oxido-1,3,2-dioxathian-5-yl)methyl)phenoxy)pyrimidin-4-yl)oxy)piperidine-1-carboxylate;

trans-isobutyl 4-((5-methyl-6-(4-((2-oxido-1,3,2-dioxathian-5-yl)methyl)phenoxy)pyrimidin-4-yl)oxy)piperidine-1-carboxylate;

cis-N-(2,4-dichlorophenyl)-4-((5-methyl-6-(4-(2-oxido-1,3,2-dioxathian-5-yl)phenoxy)pyrimidin-4-yl)oxy)piperidine-1-carboxamide;

trans-N-(2,4-dichlorophenyl)-4-(5-methyl-6-(4-(2-oxido-1,3,2-dioxathian-5-yl)phenoxy)pyrimidin-4-yl)oxy)piperidine-1-carboxamide;

cis-isopropyl 4-((5-methyl-6-(4-(2-oxido-1,3,2-dioxathian-5-yl)phenoxy)pyrimidin-4-yl)oxy)piperidine-1-carboxylate;

trans-isopropyl 4-((5-methyl-6-(4-(2-oxido-1,3,2-dioxathian-5-yl)phenoxy)pyrimidin-4-yl)oxy)piperidine-1-carboxylate;

cis-isopropyl 4-((5-methyl-6-(4-((2-oxido-1,3,2-dioxathian-5-yl)methyl)phenoxy)pyrimidin-4-yl)oxy)piperidine-1-carboxylate;

trans-isopropyl 4-((5-methyl-6-(4-((2-oxido-1,3,2-dioxathian-5-yl)methyl)phenoxy)pyrimidin-4-yl)oxy)piperidine-1-carboxylate;

cis-tert-butyl 4-(4-((2-oxido-1,3,2-dioxathian-5-yl)methyl)phenoxy)piperidine-1-carboxylate;

trans-tert-butyl 4-(4-((2-oxido-1,3,2-dioxathian-5-yl)methyl)phenoxy)piperidine-1-carboxylate;

cis-5-(4-((1-(3-isopropyl-1,2,4-oxadiazol-5-yl)piperidin-4-yl)oxy)benzyl)-1,3,2-dioxathiane 2-oxide;

trans-5-(4-((1-(3-isopropyl-1,2,4-oxadiazol-5-yl)piperidin-4-yl)oxy)benzyl)-1,3,2-dioxathiane 2-oxide;

cis-tert-butyl 4-(4-((4-((2-oxido-1,3,2-dioxathian-5-yl)methyl)phenoxy)methyl)thiazol-2-yl)piperidine-1-carboxylate;

trans-tert-butyl 4-(4-((4-((2-oxido-1,3,2-dioxathian-5-yl)methyl)phenoxy)methyl)thiazol-2-yl)piperidine-1-carboxylate;

cis-tert-butyl 4-(2-methoxy-4-((2-oxido-1,3,2-dioxathian-5-yl)methyl)phenoxy)piperidine-1-carboxylate;

trans-tert-butyl 4-(2-methoxy-4-((2-oxido-1,3,2-dioxathian-5-yl)methyl)phenoxy)piperidine-1-carboxylate;

cis-5-(4-((1-(5-ethylpyrimidin-2-yl)piperidin-4-yl)oxy)benzyl)-1,3,2-dioxathiane 2-oxide;

trans-5-(4-((1-(5-ethylpyrimidin-2-yl)piperidin-4-yl)oxy)benzyl)-1,3,2-dioxathiane 2-oxide;

cis-5-(3-chloro-4-((6-(1-(3-isopropyl-1,2,4-oxadiazol-5-yl)piperidin-4-yl)oxy)-5-methylpyrimidin-4-yl)oxy)benzyl)-1,3,2-dioxathiane 2-oxide;

trans-5-(3-chloro-4-((6-((1-(3-isopropyl-1,2,4-oxadiazol-5-yl)piperidin-4-yl)oxy)-5-methylpyrimidin-4-yl)oxy)benzyl)-1,3,2-dioxathiane 2-oxide;

cis-tert-butyl 4-((6-(2-chloro-4-((2-oxido-1,3,2-dioxathian-5-yl)methyl)phenoxy)-5-methylpyrimidin-4-yl)oxy)piperidine-1-carboxylate;

trans-tert-butyl 4-((6-(2-chloro-4-((2-oxido-1,3,2-dioxathian-5-yl)methyl)phenoxy)-5-methylpyrimidin-4-yl)oxy)piperidine-1-carboxylate;

cis-isobutyl 4-((6-(2-chloro-4-(2-oxido-1,3,2-dioxathian-5-yl)phenoxy)-5-methylpyrimidin-4-yl)oxy)piperidine-1-carboxylate;

trans-isobutyl 4-((6-(2-chloro-4-(2-oxido-1,3,2-dioxathian-5-yl)phenoxy)-5-methylpyrimidin-4-yl)oxy)piperidine-1-carboxylate;

cis-isobutyl 4-((6-(2-chloro-4-((2-oxido-1,3,2-dioxathian-5-yl)methyl)phenoxy)-5-methylpyrimidin-4-yl)oxy)piperidine-1-carboxylate;

trans-isobutyl 4-((6-(2-chloro-4-((2-oxido-1,3,2-dioxathian-5-yl)methyl)phenoxy)-5-methylpyrimidin-4-yl)oxy)piperidine-1-carboxylate;

cis-isobutyl 4-((6-(2-methoxy-4-((2-oxido-1,3,2-dioxathian-5-yl)methyl)phenoxy)-5-methylpyrimidin-4-yl)oxy)piperidine-1-carboxylate;

trans-isobutyl 4-((6-(2-methoxy-4-((2-oxido-1,3,2-dioxathian-5-yl)methyl)phenoxy)-5-methylpyrimidin-4-yl)oxy)piperidine-1-carboxylate;

cis-tert-butyl 4-((6-(2-methoxy-4-((2-oxido-1,3,2-dioxathian-5-yl)methyl)phenoxy)-5-methylpyrimidin-4-yl)oxy)piperidine-1-carboxylate;

trans-tert-butyl 4-((6-(2-methoxy-4-((2-oxido-1,3,2-dioxathian-5-yl)methyl)phenoxy)-5-methylpyrimidin-4-yl)oxy)piperidine-1-carboxylate;

cis-5-(4-((6-((1-(3-isopropyl-1,2,4-oxadiazol-5-yl)piperidin-4-yl)oxy)-5-methylpyrimidin-4-yl)oxy)-3-methoxybenzyl)-1,3,2-dioxathiane 2-oxide;

trans-5-(4-((6-((1-(3-isopropyl-1,2,4-oxadiazol-5-yl)piperidin-4-yl)oxy)-5-methylpyrimidin-4-yl)oxy)-3-methoxybenzyl)-1,3,2-dioxathiane 2-oxide;

cis-tert-butyl 4-((5-methyl-6-((6-((2-oxido-1,3,2-dioxathian-5-yl)methyl)pyridin-3-yl)oxy)pyrimidin-4-yl)oxy)piperidine-1-carboxylate;

trans-tert-butyl 4-((5-methyl-6-((6-((2-oxido-1,3,2-dioxathian-5-yl)methyl)pyridin-3-yl)oxy)pyrimidin-4-yl)oxy)piperidine-1-carboxylate;

cis-tert-butyl 4-((6-(4-(2-oxido-1,3,2-dioxathian-5-yl)phenoxy)pyrimidin-4-yl)oxy)piperidine-1-carboxylate;

trans-tert-butyl 4-((6-(4-(2-oxido-1,3,2-dioxathian-5-yl)phenoxy)pyrimidin-4-yl)oxy)piperidine-1-carboxylate;

cis-tert-butyl 4-(4-((4-(2-oxido-1,3,2-dioxathian-5-yl)phenoxy)methyl)phenoxy)piperidine-1-carboxylate.

cis-tert-butyl 4-(4-((4-((2-oxido-1,3,2-dioxathian-5-yl)methyl)phenoxy)methyl)phenoxy)piperidine-1-carboxylate;

isobutyl 4-((6-(4-(2,2-dioxido-1,3,2-dioxathian-5-yl)phenoxy)-5-methylpyrimidin-4-yl)oxy)piperidine-1-carboxylate;

5-(4-((6-((1-(3-isopropyl-1,2,4-oxadiazol-5-yl)piperidin-4-yl)oxy)-5-methylpyrimidin-4-yl)oxy)phenyl)-1,3,2-dioxathiane 2,2-dioxide;

isobutyl 4-((6-(4-((2,2-dioxido-1,3,2-dioxathian-5-yl)methyl)phenoxy)-5-methylpyrimidin-4-yl)oxy)piperidine-1-carboxylate;

5-(4-((6-((1-(5-ethylpyrimidin-2-yl)piperidin-4-yl)oxy)-5-methylpyrimidin-4-yl)oxy)benzyl)-1,3,2-dioxathiane 2,2-dioxide;

5-(4-((6-(4-(3-isopropyl-1,2,4-oxadiazol-5-yl)piperidin-1-yl)-5-nitropyrimidin-4-yl)oxy)phenyl)-1,3,2-dioxathiane 2,2-dioxide;

5-(4-((5-methyl-6-((1-(pyrimidin-2-yl)piperidin-4-yl)oxy)pyrimidin-4-yl)oxy)phenyl)-1,3,2-dioxathiane 2,2-dioxide;

5-(4-((6-((1-(5-ethylpyrimidin-2-yl)piperidin-4-yl)oxy)-5-methylpyrimidin-4-yl)oxy)phenyl)-1,3,2-dioxathiane 2,2-dioxide;

5-(4-((2-(1-(pyrimidin-2-yl)piperidin-4-yl)thiazol-4-yl)methoxy)phenyl)-1,3,2-dioxathiane 2,2-dioxide;

5-(4-((6-(4-(3-isopropyl-1,2,4-oxadiazol-5-yl)piperidin-1-yl)-5-methylpyrimidin-4-yl)oxy)phenyl)-1,3,2-dioxathiane 2,2-dioxide;

5-(4-((2-(1-(5-ethylpyrimidin-2-yl)piperidin-4-yl)thiazol-4-yl)methoxy)phenyl)-1,3,2-dioxathiane 2,2-dioxide;

tert-butyl 4-((6-(4-(2,2-dioxido-1,3,2-dioxathian-5-yl)phenoxy)-5-methylpyrimidin-4-yl)oxy)piperidine-1-carboxylate;

tert-butyl 4-(2-(4-(2,2-dioxido-1,3,2-dioxathian-5-yl)phenoxy)ethoxy)piperidine-1-carboxylate;

tert-butyl 4-(3-((6-(4-(2,2-dioxido-1,3,2-dioxathian-5-yl)phenoxy)-5-methylpyrimidin-4-yl)oxy)propyl)piperidine-1-carboxylate;
5-(4-(2-((1-(pyrimidin-2-yl)piperidin-4-yl)oxy)ethoxy)phenyl)-1,3,2-dioxathiane 2,2-dioxide;
5-(4-(2-((1-(5-ethylpyrimidin-2-yl)piperidin-4-yl)oxy)ethoxy)phenyl)-1,3,2-dioxathiane 2,2-dioxide;
5-(4-(2-((1-(3-isopropyl-1,2,4-oxadiazol-5-yl)piperidin-4-yl)oxy)ethoxy)phenyl)-1,3,2-dioxathiane 2,2-dioxide;
tert-butyl 4-((6-(4-((2,2-dioxido-1,3,2-dioxathian-5-yl)methyl)phenoxy)-5-methylpyrimidin-4-yl)oxy)piperidine-1-carboxylate;
tert-butyl 4-((6-(4-(2,2-dioxido-1,3,2-dioxathiolan-4-yl)phenoxy)-5-methylpyrimidin-4-yl)oxy)piperidine-1-carboxylate;
5-(4-((6-((1-(3-isopropyl-1,2,4-oxadiazol-5-yl)piperidin-4-yl)oxy)-5-methylpyrimidin-4-yl)oxy)benzyl)-1,3,2-dioxathiane 2,2-dioxide;
ethyl 4-((6-(4-(2,2-dioxido-1,3,2-dioxathian-5-yl)phenoxy)-5-methylpyrimidin-4-yl)oxy)piperidine-1-carboxylate;
benzyl 4-((6-(4-(2,2-dioxido-1,3,2-dioxathian-5-yl)phenoxy)-5-methylpyrimidin-4-yl)oxy)piperidine-1-carboxylate;
5-(4-(((6-((1-benzylpiperidin-4-yl)oxy)-5-methylpyrimidin-4-yl)oxy)phenyl)-1,3,2-dioxathiane 2,2-dioxide;
ethyl 4-((6-(4-((2,2-dioxido-1,3,2-dioxathian-5-yl)methyl)phenoxy)-5-methylpyrimidin-4-yl)oxy)piperidine-1-carboxylate;
5-(4-((5-methyl-6-((1-(pyrimidin-2-yl)piperidin-4-yl)oxy)pyrimidin-4-yl)oxy)benzyl)-1,3,2-dioxathiane 2,2-dioxide;
N-(2,4-dichlorophenyl)-4-((6-(4-(2,2-dioxido-1,3,2-dioxathian-5-yl)phenoxy)-5-methylpyrimidin-4-yl)oxy)piperidine-1-carboxamide;
isopropyl 4-((6-(4-(2,2-dioxido-1,3,2-dioxathian-5-yl)phenoxy)-5-methylpyrimidin-4-yl)oxy)piperidine-1-carboxylate;
isopropyl 4-((6-(4-((2,2-dioxido-1,3,2-dioxathian-5-yl)methyl)phenoxy)-5-methylpyrimidin-4-yl)oxy)piperidine-1-carboxylate;
tert-butyl 4-((2,2-dioxido-1,3,2-dioxathian-5-yl)methyl)phenoxy)piperidine-1-carboxylate;
5-(4-((1-(3-isopropyl-1,2,4-oxadiazol-5-yl)piperidin-4-yl)oxy)benzyl)-1,3,2-dioxathiane 2,2-dioxide;
tert-butyl 4-(4-((4-((2,2-dioxido-1,3,2-dioxathian-5-yl)methyl)phenoxy)methyl)thiazol-2-yl)piperidine-1-carboxylate;
5-(4-((1-(5-ethylpyrimidin-2-yl)piperidin-4-yl)oxy)benzyl)-1,3,2-dioxathiane 2,2-dioxide;
5-(3-chloro-4-((6-((1-(3-isopropyl-1,2,4-oxadiazol-5-yl)piperidin-4-yl)oxy)-5-methylpyrimidin-4-yl)oxy)benzyl)-1,3,2-dioxathiane 2,2-dioxide;
tert-butyl 4-((6-(2-chloro-4-((2,2-dioxido-1,3,2-dioxathian-5-yl)methyl)phenoxy)-5-methylpyrimidin-4-yl)oxy)piperidine-1-carboxylate;
isobutyl 4-((6-(2-chloro-4-(2,2-dioxido-1,3,2-dioxathian-5-yl)phenoxy)-5-methylpyrimidin-4-yl)oxy)piperidine-1-carboxylate;
isobutyl 4-((6-(2-chloro-4-((2,2-dioxido-1,3,2-dioxathian-5-yl)methyl)phenoxy)-5-methylpyrimidin-4-yl)oxy)piperidine-1-carboxylate;
isobutyl 4-((6-(4-((2,2-dioxido-1,3,2-dioxathian-5-yl)methyl)-2-methoxyphenoxy)-5-methylpyrimidin-4-yl)oxy)piperidine-1-carboxylate;
tert-butyl 4-((6-(4-((2,2-dioxido-1,3,2-dioxathian-5-yl)methyl)-2-methoxyphenoxy)-5-methylpyrimidin-4-yl)oxy)piperidine-1-carboxylate;
5-(4-((6-((1-(3-isopropyl-1,2,4-oxadiazol-5-yl)piperidin-4-yl)oxy)-5-methylpyrimidin-4-yl)oxy)-3-methoxybenzyl)-1,3,2-dioxathiane 2,2-dioxide;
tert-butyl 4-((6-((6-((2,2-dioxido-1,3,2-dioxathian-5-yl)methyl)pyridin-3-yl)oxy)-5-methylpyrimidin-4-yl)oxy)piperidine-1-carboxylate;
tert-butyl 4-((6-(4-(2,2-dioxido-1,3,2-dioxathian-5-yl)phenoxy)pyrimidin-4-yl)oxy)piperidine-1-carboxylate;
tert-butyl 4-(4-((4-((2,2-dioxido-1,3,2-dioxathian-5-yl)methyl)phenoxy)methyl)phenoxy)piperidine-1-carboxylate.
tert-butyl 4-(4-((4-(2,2-dioxido-1,3,2-dioxathian-5-yl)phenoxy)methyl)phenoxy)piperidine-1-carboxylate;
tert-butyl 4-(4-((2,2-dioxido-1,3,2-dioxathian-5-yl)methyl)-2-methoxyphenoxy)piperidine-1-carboxylate;
tert-butyl 4-(4-((4-(2,2-dioxido-1,3,2-dioxathian-5-yl)phenoxy)methyl)thiazol-2-yl)piperidine-1-carboxylate;
tert-butyl 4-((6-(4-((2,2-dioxido-1,3,2-dioxathiolan-4-yl)methyl)phenoxy)-5-methylpyrimidin-4-yl)oxy)piperidine-1-carboxylate;
5-(4-(3-(1-(pyrimidin-2-yl)piperidin-4-yl)propoxy)phenyl)-1,3,2-dioxathiane 2,2-dioxide.

The novel compounds of this invention may be prepared using the reactions and techniques described in the below section along with, whenever appropriate other suitable processes known to a skilled person. The reactions are performed in solvents appropriate to the reagents and materials employed and are suitable for the transformations being effected. It is understood by those skilled in the art that the nature and order of the synthetic steps presented may be varied for the purpose of optimizing the formation of the compounds of the present invention and also that certain steps may be modified, altered, obvious steps added or deleted in order to optimize as well as required for preparing the compounds of the present invention. Such, obvious changes should also be considered as being part of the present invention.

Scheme 1: Compounds of general Formula (I) where X, Y, Z, W, $R_1$, $R_2$, m, n and p are as defined earlier and 'X' is CH, 'W' is N may be prepared according to the scheme described below:

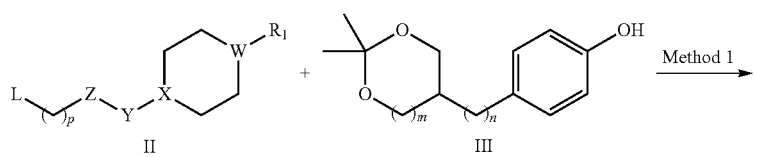

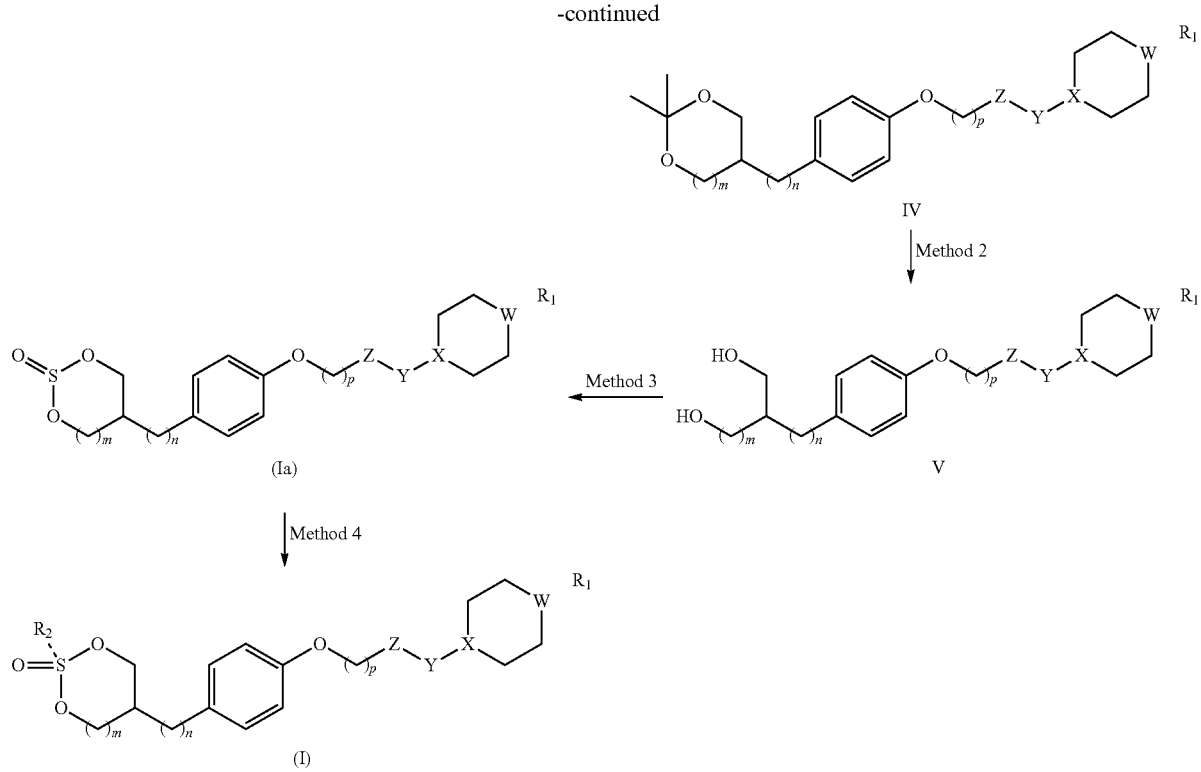

The process of synthesizing the compounds of general Formula (I) comprises the steps of:
i. reacting compounds of general Formula (II), wherein 'L' represents a suitable leaving group such as halogen, mesylate, tosylate, triflate, and the like with compounds of general Formula (III), to yield compound of general Formula (IV);
ii. deprotecting compounds of general Formula (IV), where all symbols are as defined earlier with suitable deprotecting reagents to yield the compound of general Formula (V);
iii. converting compounds of general Formula (V) to cyclic sulfite of general Formula (Ia); and
iv Oxidizing the cyclic sulfite of Formula (Ia) with suitable oxidizing agents to yield compounds of general Formula (I) where 'R$_2$' represents an oxo group.

Scheme 2: Compounds of general Formula (I) where Z, W, R$_1$, R$_2$, m, n and p are as defined earlier and X is N, Y is a bond, may be prepared according to the scheme described here:

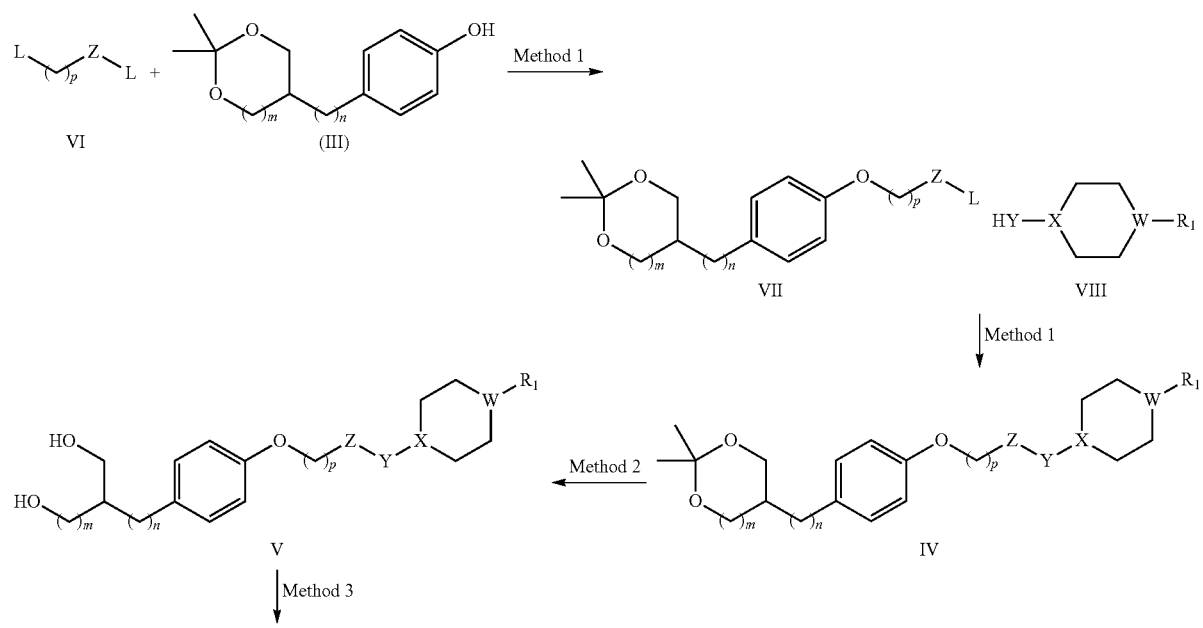

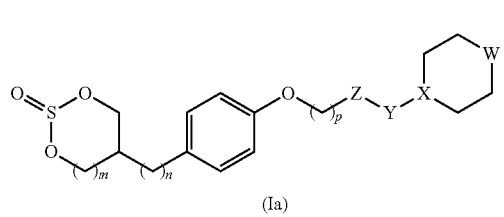

(Ia)

Method 4 →

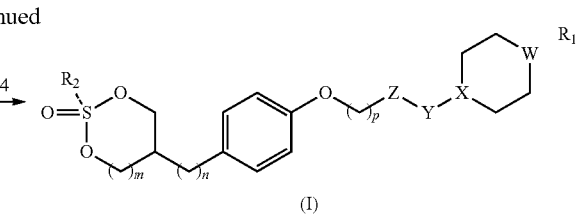

(I)

The process of synthesizing the compounds of general Formula (I), the process comprising:
i. reacting compounds of general Formula (VI), wherein L represents suitable leaving group such as halogen, mesylate, tosylate, triflate, and the like and Z is as defined earlier with compounds of general Formula (III) to yield compound of general Formula (VII), where all symbols are as defined earlier;
ii. reacting compounds of general Formula (VII) with compounds of general Formula (VIII), where X, Y, W and $R_1$ are as defined earlier with the similar procedure given for the preparation of compounds of general Formula (VII) to yield compound of general Formula (IV), where all symbols are as defined earlier;
iii. deprotecting compounds of general Formula (IV), where all symbols are as defined earlier with suitable deprotecting reagents, to yield the compound of general Formula (V);
iv. reacting compounds of general Formula (V), where all symbols are as defined earlier with suitable regents, to yield cyclic sulfite of the compounds of general Formula (Ia); and
v. oxidizing cyclic sulfite of Formula (Ia) with suitable oxidizing agents to yield compound of general Formula (I), where $R_2$ represents an oxo group.

Method 1: The compound of Formula (IV) of scheme 1 may be prepared by reacting compounds of Formula (II) with compounds of Formula (III) and the compounds of Formula (VII) and (IV) of scheme 2 may be prepared by reacting compounds of Formula (VI) with compounds of Formula (III) and compounds of Formula (VII) with compounds of Formula (VIII), respectively under suitable conditions. The reaction may be carried out in presence of one or more solvents such as acetone, tetrahydrofuran, dimethyl sulfoxide, dioxane, acetonitrile, dimethyl formamide, dimethoxy ethane, benzene, toluene, petroleum ether, heptane, hexane, 2-butanone, xylene, alcohols such as methanol, ethanol, propanol, butanol, iso-butanol, tert-butanol, pentanol and the like or mixtures thereof. Bases such as alkali metal carbonates such as $K_2CO_3$, $Na_2CO_3$, $CsCO_3$, and the like, or alkali metal hydroxides such as NaOH, KOH, and the like, or alkali metal alkoxides such as tert-BuOK, tert-BuONa, and the like, may be used during this reaction. Alkali metal hydrides such as NaH, KH can be used whenever solvent employed is not protic or contain carbonyl group. The reaction may be carried out at a temperature in the range from about 0° C. to about reflux temperature of the solvent(s) used and the reaction time may range from about 1 to about 48 hours.

Method 2: The compound of Formula (V) may be prepared by reacting compounds of Formula (IV) under suitable conditions. The reactions may be carried out in the presence of one or more solvents such as acetone and the like or mixtures thereof. Acids such as conc. HCl and the like may be used during this reaction. The reaction may be carried out at a temperature in the range from about 0° C. to about reflux temperature of the solvent(s) used and the reaction time may range from about 1 to about 48 hours.

Method 3: The compound of Formula (Ia) may be prepared by reacting compounds of Formula (V) under suitable conditions. The reactions may be carried out in the presence of one or more solvents such as dichloromethane, and the like or mixtures thereof and thionyl chloride may be used during this reaction. The reaction may be carried out at a temperature in the range from about 0° C. to about reflux temperature of the solvent(s) used and the reaction time may range from about 1 to about 48 hours.

Method 4: The compounds of Formula (I) may be prepared by oxidizing compounds of Formula (Ia). The reactions may be carried out in the presence of oxidizing agents such as $KMnO_4$, $RuCl_3.3H_2O$ and $NaIO_4$, and the like, and solvents such as acetonitrile, water, and the like or mixtures thereof may be used. The reaction may be carried out at a temperature in the range from about 0° C. to about reflux temperature of the solvent(s) used and the reaction time may range from about 1 to about 48 hours.

The invention is further illustrated by the following examples, which are provided merely to be exemplary of the invention and do not limit the scope of the invention. Certain modifications and equivalents will be apparent to those skilled in the art and are intended to be included within the scope of the invention.

1H NMR spectral data given in the examples (vide infra) are recorded using a 400 MHz spectrometer (Bruker AVANCE-400) and reported in δ scale. Until and otherwise mentioned the solvent used for NMR is $CDCl_3$.

Example 1

Preparation of cis-5-(4-((6-(4-(3-isopropyl-1,2,4-oxadiazol-5-yl)piperidin-1-yl)-5-nitropyrimidin-4-yl)oxy)phenyl)-1,3,2-dioxathiane 2-oxide Step I: Preparation of diethyl 2-(4-(benzyloxy)phenyl)malonate To a suspension of NaH (54 gm, 1.11 moles) in dry THF (500 ml) a solution of ethyl 2-(4-(benzyloxy)phenyl)acetate (100 gm, 0.37 moles) in dry THF (100 ml) was added at 0° C. To this was added diethyl carbonate (180 ml, 1.48 mole) dropwise over a period of one hour maintaining the reaction temperature at below 5° C. The reaction mixture was then stirred for 18 hours at 30° C. The contents of the reaction mixture were poured into ice cold water and extracted with ethyl acetate. The organic extract was successively washed with water & brine, dried over sodium sulfate and evaporated under reduced pressure to yield 100 gm of product as white solid.

$^1$HNMR: 1.26 (t, J=6.8 Hz, 6H), 4.12-4.27 (m, 4H), 4.55 (s, 1H), 5.05 (s, 2H), 6.94-6.98 (m, 2H), 7.30-7.34 (m, 3H), 7.36-7.44 (m, 4H).

Step II: Preparation of 2-(4-(benzyloxy)phenyl)propane-1,3-diol

To a solution of diethyl 2-(4-(benzyloxy)phenyl)malonate (20 gm, 0.0585 mole) in ethanol (200 ml) was added sodium borohydride (17.4 gm, 0.4678 mole) in portions at 0° C. and the reaction mixture was stirred for 4 hrs at 30° C. The reaction mixture was poured into ice cold water, acidified with conc. HCl and extracted with ethyl acetate. The organic extract was successively washed with water & brine, dried over sodium sulfate and concentrated under reduced pressure to provide 14.5 gm of product as white solid.

$CDCl_3$, 400 MHz, 2.81 (m, 1H), 3.88-4.14 (m, 4H), 5.04 (s, 2H), 6.92-6.99 (m, 2H), 7.7-7.22 (m, 3H), 7.28-7.43 (m, 4H).

Step III: Preparation of 5-(4-(benzyloxy)phenyl)-2,2-dimethyl-1,3-dioxane

To a suspension of 2-(4-(benzyloxy)phenyl)propane-1,3-diol (2.0 gm, 0.00775 moles) in dry toluene (500 ml), dry acetone (20 ml) and PTSA (1.2 gm, 0.0062 mole) were added and the reaction mixture was stirred for 18 hours at 30° C. The reaction mixture was poured into ice cold water and extracted with ethyl acetate. The organic extract was washed successively with water & brine, dried over sodium sulfate and evaporated under reduced pressure to yield 1.47 gm product as white solid.

$^1$HNMR: 1.46 (s, 3H), 1.55 (s, 3H), 3.04-3.12 (m, 1H), 3.92-3.12 (m, 4H), 5.04 (s, 2H), 6.93 (d, J=8.4 & 2.8 Hz, 2H), 7.15 (d, J=8.8 Hz, 2H), 7.26 (s, 1H), 7.30-7.43 (m, 4H).

Step IV: Preparation of 4-(2,2-dimethyl-1,3-dioxan-5-yl)phenol

To a suspension of 10% Pd/C (85 mg) in methanol was added a solution of 5-(4-(benzyloxy)phenyl)-2,2-dimethyl-1, 3-dioxane (850.0 gm, 0.00775 moles) in methanol (20 ml). To this was added ammonium formate (900 mg, 0.0143 mole) and the reaction mixture was refluxed for 2 hrs. The reaction mixture was then cooled to 30° C. and filtered through celite. The filtrate was evaporated under reduced pressure and residue was dissolved in dichloromethane and filtered through celite. The filtrate was evaporated under reduced pressure to yield 600 mg product as white solid.

$^1$HNMR: 1.47 (s, 3H), 1.55 (s, 3H), 3.03-3.11 (m, 4H), 6.77-6.81 (m, 2H), 7.11 (d, J=9.2 Hz, 2H).

Step V: Preparation of 4-chloro-6-(4-(2,2-dimethyl-1,3-dioxan-5-yl)phenoxy)-5-nitropyrimidine To a solution of 4-(2,2-dimethyl-1,3-dioxan-5-yl)phenol (500 mg, 0.0026 moles) and 4,6 dichloro-5-nitropyrimidine (600 mg, 0.0028 mole) in dimethyl acetamide (10 ml) $K_2CO_3$ (776 mg, 0.00577 mole) was added –20° C. The reaction mixture was stirred for about 2 hours at –10° C. to –18° C. The reaction mixture was then poured into ice cold water and extracted with ethyl acetate. The organic extract was successively washed with water & brine, dried over sodium sulfate and evaporated under reduced pressure to yield crude product which was purified by column chromatography using 15% ethyl acetate in hexane as eluent to yield 500 mg product as pale yellow solid.

Step VI: Preparation of 5-(1-(6-(4-(2,2-dimethyl-1,3-dioxan-5-yl)phenoxy)-5-nitropyrimidin-4-yl)piperidin-4-yl)-3-isopropyl-1,2,4-oxadiazole To an ice-cold solution of 4-chloro-6-(4-(2,2-dimethyl-1, 3-dioxan-5-yl)phenoxy)-5-nitropyrimidine (500 mg, 0.0013 moles) and 3-isopropyl-5-(piperidin-4-yl)-1,2,4-oxadiazole hydrochloride (293 mg, 0.0015 mole) in dichloromethane (10 ml) diisopropyl ethyl amine (0.24 ml, 0.0016 mole) was added and the reaction mixture was stirred for 4 hours at 27° C. The reaction mixture was poured into ice cold water and extracted with dichloromethane. The organic extract was successively washed with water & brine, dried over calcium chloride and evaporated under reduced pressure. The crude product so obtained was purified by column chromatography using 20% ethyl acetate in hexane as eluent to yield 450 mg product as pale yellow solid.

Step VII: Preparation of 2-(4-(6-(4-(3-isopropyl-1,2, 4-oxadiazol-5-yl)piperidin-1-yl)-5-nitropyrimidin-4-yloxy)phenyl)propane-1,3-diol To a solution of 5-(1-(6-(4-(2,2-dimethyl-1,3-dioxan-5-yl) phenoxy)-5-nitropyrimidin-4-yl)piperidin-4-yl)-3-isopropyl-1,2,4-oxadiazole (500 mg, 0.0095 moles) in acetone (10 ml) was added conc. HCl (3 ml) and the reaction mixture was stirred for 4 hours at 27° C. The reaction mixture was concentrated and the residue was dissolved in ethyl acetate. The organic extract was successively washed with water & brine, dried over sodium sulfate and evaporated under reduced pressure to yield 250 mg product as yellow solid.

Step VIII: Preparation of cis-5-(4-((6-(4-(3-isopropyl-1,2,4-oxadiazol-5-yl)piperidin-1-yl)-5-nitropyrimidin-4-yl)oxy)phenyl)-1,3,2-dioxathiane 2-oxide To an ice-cold solution of 2-(4-(6-(4-(3-isopropyl-1,2,4-oxadiazol-5-yl)piperidin-1-yl)-5-nitropyrimidin-4-yloxy) phenyl)propane-1,3-diol (200 mg, 0.000413 moles) in dichloromethane (10 ml) triethylamine (0.23 ml) was added followed by thionyl chloride (0.045 ml, 0.0062 mole) and the reaction mixture was stirred for 5 hours at 27° C. The reaction mixture was poured into ice cold water and extracted with dichloromethane. The organic extract was successively washed with water and brine, dried over sodium sulfate and evaporated under reduced pressure to yield crude product containing a mixture of cis and trans isomers which were separated by column chromatography using 16% ethyl acetate in hexane as eluent.

$^1$HNMR: 1.33 (d, J=7.2 Hz, 6H), 1.97-2.07 (m, 2H), 2.28 (dd, J=9.6 & 14 Hz, 2H), 3.05-3.11 (m, 1H), 3.23-3.35 (m, 3H), 3.59-3.65 (m, 1H), 3.89-3.95 (m, 2H), 4.08-4.13 (m, 2H), 4.97 (t, J=23.0 Hz, 2H), 7.16 (d, J=8.3 Hz, 2H), 7.30 (d, J=8.4 Hz, 2H), 8.21 (s, 1H).

Example 2

Preparation of trans-5-(4-((6-(4-(3-isopropyl-1,2,4-oxadiazol-5-yl)piperidin-1-yl)-5-nitropyrimidin-4-yl) oxy)phenyl)-1,3,2-dioxathiane 2-oxide Later fractions from column chromatography in example 1 were evaporated to yield the trans isomer $^1$HNMR: 1.33 (d, J=6.8 Hz, 6H), 2.00-2.07 (m, 2H), 2.20 (dd, J=14 & 3.6 Hz, 2H), 3.04-3.10 (m, 2H), 3.24-3.35 (m, 3H), 4.06-4.12 (m, 4H), 5.22 (dd, J=12.0 & 3.6 Hz, 2H), 7.17 (d, J=8.4 Hz, 2H), 7.55 (d, J=8.8 Hz, 2H), 8.21 (s, 1H).

Example 3

Preparation of cis-5-(4-((6-((1-(3-isopropyl-1,2,4-oxadiazol-5-yl)piperidin-4-yl)oxy)-5-methylpyrimidin-4-yl)oxy)phenyl)-1,3,2-dioxathiane 2-oxide Step I: Preparation of 5-(4-(6-chloro-5-methylpyrimidin-4-yloxy)piperidin-1-yl)-3-isopropyl-1,2,4-oxadiazole Potassium tert-butoxide (478 mg, 0.00426 moles) was added to a solution of 1-(3-iso-propyl-1,2,4-oxadiazol-5-yl)

piperidin-4-ol (0.9 gm, 0.00426 moles) and 4,6-dichloro-5-methylpyrimidine (690 mg, 0.00426 moles) in dry THF (30 ml) at 0° C. and the reaction mixture was stirred for 20 hours at 30° C. The reaction mixture was poured into ice cold water and extracted with ethyl acetate. The organic extract was successively washed with water & brine, dried over sodium sulfate and evaporated under reduced pressure to yield 900 mg product as off white solid.

$^1$HNMR: 1.29 (d, J=7.2 Hz, 6H), 1.89-1.97 (m, 2H), 2.07-2.24 (m, 2H), 2.24 (s, 3H), 2.86-2.93 (m, 1H), 3.60-3.66 (m, 2H), 3.81-3.87 (m, 2H), 5.40-5.45 (m, 1H), 8.40 (m, 1H).

Step II: Preparation of 5-(4-(6-(4-(2,2-dimethyl-1,3-dioxan-5-yl)phenoxy)-5-methylpyrimidin-4-yloxy)piperidin-1-yl)-3-isopropyl-1,2,4-oxadiazole Cesium carbonate (755 mg, 0.002317 moles) was added to a solution of 5-(4-(6-chloro-5-methylpyrimidin-4-yloxy)piperidin-1-yl)-3-isopropyl-1,2,4-oxadiazole (1.2 gm, 0.003365 moles) and 4-(2,2-dimethyl-1,3-dioxan-5-yl)phenol (700 mg, 0.003365 moles) in dry DMF (10 ml) and the reaction mixture was stirred at 80° C. for 3 hours. Then reaction mixture was poured into ice cold water and extracted with ethyl acetate. The organic extract was successively washed with water & brine, dried over sodium sulfate and concentrated under reduced pressure. The crude product so obtained was purified by column chromatography (silica gel) using 15% ethyl acetate in hexane as eluent to obtain 770 mg product as white solid.

Step III: Preparation of Preparation of 2-(4-(6-(1-(3-isopropyl-1,2,4-oxadiazol-5-yl)piperidin-4-yloxy)-5-methylpyrimidin-4-yloxy)phenyl)propane-1,3-diol To a solution of 5-(4-(6-(4-(2,2-dimethyl-1,3-dioxan-5-yl)phenoxy)-5-methylpyrimidin-4-yloxy)piperidin-1-yl)-3-isopropyl-1,2,4-oxadiazole (500 mg, 0.0095 moles) in acetone (10 ml) conc. HCl (3 ml) was added portion-wise and reaction mixture was stirred for 2 hours at 27° C. The reaction mixture was concentrated and residue was dissolved in ethyl acetate. The organic extract was successively washed with water & brine, dried over sodium sulfate and evaporated under reduced pressure to yield 360 mg product as white solid.

Step IV: Preparation of Cis-5-(4-((6-((1-(3-isopropyl-1,2,4-oxadiazol-5-yl)piperidin-4-yl)oxy)-5-methylpyrimidin-4-yl)oxy)phenyl)-1,3,2-dioxathiane 2-oxide To an ice-cold solution of 2-(4-(6-(1-(3-isopropyl-1,2,4-oxadiazol-5-yl)piperidin-4-yloxy)-5-methylpyrimidin-4-yloxy)phenyl)propane-1,3-diol (360 mg, 0.000767 moles) in dichloromethane (10 ml) pyridine (0.2 ml, 0.00307 mole) was added followed by thionyl chloride (0.06 ml, 0.00092 mole) and the reaction mixture was stirred for 15 min. The reaction mixture was poured into ice cold water and extracted with dichloromethane. The organic extract was successively washed with water & brine, dried over calcium chloride and evaporated under reduced pressure to yield crude product containing a mixture of cis and trans isomers which were separated by column chromatography using 20% ethyl acetate in hexane as eluent.

$^1$HNMR: 1.30 (d, J=6.8 Hz, 6H), 1.93-1.97 (m, 2H), 2.07-2.12 (m, 2H), 2.17 (s, 3H), 2.88-2.92 (m, 1H), 3.60-3.67 (m, 3H), 3.82-3.88 (m, 2H), 3.91-3.95 (dd, J=11.8 & 4.4 Hz, 2H), 4.97 (t, J=12 Hz, 2H), 5.40-5.43 (m, 1H), 7.12-7.15 (m, 2H), 7.27-7.30 (m, 2H), 8.25 (s, 1H).

Example 4

Preparation of trans-5-(4-((6-((1-(3-isopropyl-1,2,4-oxadiazol-5-yl)piperidin-4-yl)oxy)-5-methylpyrimidin-4-yl)oxy)phenyl)-1,3,2-dioxathiane 2-oxide Later fractions from column chromatography in example 3 were evaporated to yield the trans isomer $^1$HNMR: δ 1.30 (d, J=6.8 Hz, 6H), 1.93-1.99 (m, 2H), 2.07-2.13 (m, 2H), 2.19 (s, 3H), 2.87-2.92 (m, 1H), 3.08-3.10 (m, 1H), 3.62-3.68 (m, 2H), 3.82-3.89 (m, 2H), 4.08-4.12 (dd, J=12 & 3.2 Hz, 2H), 5.21 (dd, J=12 & 3.6 Hz, 2H), 5.41-5.44 (m, 1H), 7.14-7.16 (m, 2H), 7.52-7.54 (m, 2H), 8.26 (s, 1H).

Example 5

Preparation of cis-5-(4-((5-methyl-6-((1-(pyrimidin-2-yl)piperidin-4-yl)oxy)pyrimidin-4-yl)oxy)phenyl)-1,3,2-dioxathiane 2-oxide

Step I: Preparation of 4-chloro-5-methyl-6-(1-(pyrimidin-2-yl)piperidin-4-yloxy)pyrimidine Potassium tert-butoxide (2.86 gm, 0.01397 moles) was added to an ice-cold solution of 1-(pyrimidin-2-yl)piperidin-4-ol (2.50 gm, 0.01397 moles) and 4,6-dichloro-5-methylpyrimidine (2.27 mg, 0.01397 moles) in dry THF (15 ml) and the reaction mixture was stirred for 5 hours at 30° C. The reaction mixture was poured into ice cold water, solid precipitated was filtered and dried under vacuum to obtain 140 mg of product.

$^1$HNMR: δ 1.79-1.87 (m, 2H), 2.04-2.11 (m, 2H), 2.23 (s, 3H), 3.69-3.76 (m, 2H), 4.16-4.22 (m, 2H), 5.41-5.46 (m, 1H), 6.49 (t, J=4.48 Hz, 1H), 8.31 (d, J=4.8 Hz, 2H), 8.40 (s, 1H).

Step II: Preparation of 4-(4-(2,2-dimethyl-1,3-dioxan-5-yl)phenoxy)-5-methyl-6-(1-(pyrimidin-2-yl)piperidin-4-yloxy)pyrimidine Cesium carbonate (2.97 mg, 0.00914 moles) was added to a solution 4-chloro-5-methyl-6-(1-(pyrimidin-2-yl)piperidin-4-yloxy)pyrimidine (1.39 gm, 0.00457 moles) and 4-(2,2-dimethyl-1,3-dioxan-5-yl)phenol (950 mg, 0.00457 moles) in dry DMF (10 ml) and the reaction mixture was stirred at 60° C. for 12 hours. Then reaction mixture was poured into ice cold water and extracted with ethyl acetate. The organic extract was successively washed with water & brine, dried over sodium sulfate and concentrated under reduced pressure. The crude product so obtained was purified by column chromatography (silica gel) using 22% ethyl acetate in hexane as eluent to obtain 1.5 gm product as white solid.

Step III: Preparation of 2-(4-(5-methyl-6-(1-(pyrimidin-2-yl)piperidin-4-yloxy)pyrimidin-4-yloxy)phenyl)propane-1,3-diol To a solution of 4-(4-(2,2-dimethyl-1,3-dioxan-5-yl)phenoxy)-5-methyl-6-(1-(pyrimidin-2-yl)piperidin-4-yloxy)pyrimidine (1.5 gm, 0.0031 moles) in acetone (20 ml) conc. HCl (2 ml) was added portion-wise and the reaction mixture was stirred for 3 hours at 27° C. The reaction mixture was concentrated and the residue was dissolved in ethyl acetate. The organic extract was successively washed with water & brine, dried over sodium sulfate and evaporated under reduced pressure to yield 700 mg product as white solid Step IV: Preparation of Cis-5-(4-((5-methyl-6-((1-(pyrimidin-2-yl)piperidin-4-yl)oxy)pyrimidin-4-yl)oxy)phenyl)-1,3,2-dioxathiane 2-oxide To an ice-cold solution of 2-(4-(5-methyl-6-(1-(pyrimidin-2-yl)piperidin-4-yloxy)pyrimidin-4-yloxy)phenyl)propane-1,3-diol (700 mg, 0.0016 moles) in dichloromethane (10 ml) pyridine (0.512 ml, 0.0064 mole) was added followed by thionyl chloride (0.115 ml, 0.0016 mole) and reaction mixture was stirred for 3 hours at 27° C. The reaction mixture was poured into ice cold water and extracted with dichloromethane. The organic extract was washed with water, dried over calcium chloride and evaporated under reduced pressure. The crude product containing a mixture of cis and trans isomers was purified by column chromatography using 22% ethyl acetate in hexane as eluent.
$^1$HNMR: δ 1.81-1.89 (m, 2H), 2.04-2.11 (m, 2H), 2.17 (s, 3H), 3.58-3.64 (m, 1H), 3.72-3.78 (m, 2H), 3.93 (dd, J=11.6 & 4.4 Hz, 2H), 4.17-4.23 (m, 2H), 4.97 (t, J=11.8 Hz, 2H), 5.41-5.45 (m, 1H), 6.47 (t, J=4.8 Hz, 1H), 7.14 (d, J=8.8 Hz, 2H), 7.27-7.29 (m, 2H), 8.26 (s, 1H), 8.31 (d, J=4.4 Hz, 2H).

Example 6

Preparation of trans-5-(4-((5-methyl-6-((1-(pyrimidin-2-yl)piperidin-4-yl)oxy)pyrimidin-4-yl)oxy)phenyl)-1,3,2-dioxathiane 2-oxide Later fractions from column chromatography in example 3 were evaporated to yield the trans isomer
$^1$HNMR: δ 1.82-1.90 (m, 2H), 2.05-2.12 (m, 2H), 2.17 (s, 3H), 3.08-3.11 (m, 1H), 3.72-3.78 (m, 2H), 4.11 (dd, J=12 & 3.2 Hz, 2H), 4.17-4.23 (m, 2H), 5.20 (dd, J=12 & 4.0 Hz, 2H), 5.41-5.46 (m, 1H), 6.49 (t, J=4.8 Hz, 1H), 7.12-7.17 (m, 2H), 7.53 (d, J=8.4 Hz, 2H), 8.26 (s, 1H), 8.30 (d, J=4.4 Hz, 2H).

Example 7

Preparation of cis-5-(4-((2-(1-(pyrimidin-2-yl)piperidin-4-yl)thiazol-4-yl)methoxy)phenyl)-1,3,2-dioxathiane 2-oxide Step I: Preparation of 4-((4-(2,2-dimethyl-1,3-dioxan-5-yl)phenoxy)methyl)-2-(1-(pyrimidin-2-yl)piperidin-4-yl)thiazole Cesium carbonate (735 mg, 0.0022 moles) was added to a solution of (2-(1-(pyrimidin-2-yl)piperidin-4-yl)thiazol-4-yl)methyl methanesulfonate (490 gm, 0.00112 moles) and 4-(2,2-dimethyl-1,3-dioxan-5-yl)phenol (281 mg, 0.001384 moles) in DMF (10 ml) and the reaction mixture was stirred at 60° C. for 2 hours. Then the reaction mixture was then poured into ice cold water and extracted with ethyl acetate. The organic extract was successively washed with water & brine, dried over sodium sulfate and concentrated under reduced pressure. The crude product so obtained was purified by column chromatography (silica gel) using 22% ethyl acetate in hexane as eluent to obtain 600 mg product as white solid.

Step II: Preparation of 2-(4-((2-(1-(pyrimidin-2-yl)piperidin-4-yl)thiazol-4-yl)methoxy)phenyl)propane-1,3-diol To a solution of 4-((4-(2,2-dimethyl-1,3-dioxan-5-yl)phenoxy)methyl)-2-(1-(pyrimidin-2-yl)piperidin-4-yl)thiazole (500 mg, 0.0010 moles) in acetone (20 ml), conc. HCl (2 ml) was added portion-wise and the reaction mixture was stirred for 12 hours at 27° C. The reaction mixture was concentrated and the residue was dissolved in ethyl acetate. The organic layer was successively washed with water & brine, dried over sodium sulfate and evaporated under reduced pressure to yield 500 mg product as white solid Step IV: Preparation of cis-5-(4-((2-(1-(pyrimidin-2-yl)piperidin-4-yl)thiazol-4-yl)methoxy)phenyl)-1,3,2-dioxathiane 2-oxide To an ice-cold solution of 2-(4-((2-(1-(pyrimidin-2-yl)piperidin-4-yl)thiazol-4-yl)methoxy)phenyl)propane-1,3-diol (500 mg, 0.00108 moles) in dichloromethane (10 ml) pyridine (0.512 ml, 0.0064 mole) was added followed by thionyl chloride (0.095 ml, 0.0013 mole) and the reaction mixture was stirred for 2 hours at 27° C. The reaction mixture was poured into ice cold water and extracted with dichloromethane.
The organic extract was washed with water, dried over calcium chloride and evaporated under reduced pressure to yield crude product containing a mixture of cis and trans isomers, which were separated by column chromatography using 28% ethyl acetate in hexane as eluent.
$^1$HNMR: δ 1.79-1.83 (m, 2H), 2.21 (d, J=10.8 Hz, 2H), 3.02-3.09 (m, 2H), 3.28-3.31 (m, 1H), 3.53-3.54 (m, 1H), 3.87 (dd, J=12 & 4.8 Hz, 2H), 4.85-4.95 (m, 4H), 5.15 (s, 2H), 6.48 (t, J=4.8 Hz, 1H), 6.98 (d, J=8.8 Hz, 2H), 7.17 (m, 3H), 8.31 (d, J=4.8 Hz, 2H)

Example 8

Preparation of trans-5-(4-((2-(1-(pyrimidin-2-yl)piperidin-4-yl)thiazol-4-yl)methoxy)phenyl)-1,3,2-dioxathiane 2-oxide Later fractions from column chromatography in example 3 were evaporated to yield the trans isomer.
$^1$HNMR: δ 1.76-1.86 (m, 2H), 2.22 (d, J=10.8 Hz, 2H), 3.02-3.09 (m, 3H), 3.27-3.35 (m, 1H), 4.07 (dd, J=12 & 3.6 Hz, 2H), 4.88 (d, J=13.6 Hz, 2H), 5.14 (dd, J=12 & 3.6 Hz, 2H), 5.18 (s, 2H), 6.48 (t, J=4.6 Hz, 1H), 6.98-7.02 (m, 2H), 7.21 (s, 1H), 7.37-7.41 (m, 2H), 8.31 (d, J=4.8 Hz, 2H).
The following compounds were prepared by procedure similar to those described in example 1-4 with appropriate variations in reactants, reaction conditions and quantities of reagents.

Example 9 cis-5-(4-((6-((1-(5-ethylpyrimidin-2-yl)piperidin-4-yl)oxy)-5-methylpyrimidin-4-yl)oxy)phenyl)-1,3,2-dioxathiane 2-oxide $^1$HNMR: δ 1.20 (t, J=7.6 Hz, 3H), 1.80-1.88 (m, 2H), 2.05-2.10 (m, 2H), 2.16 (s, 3H), 2.47 (q, J=7.8 Hz, 2H), 3.58-3.64 (m, 1H), 3.67-3.73 (m, 2H), 3.93 (dd, J=11.6 & 4.4 Hz, 2H), 4.15-4.21 (m, 2H), 4.97 (t, J=10.4 Hz, 2H), 5.40-5.44 (m, 1H), 7.13 (d, J=8.4 Hz, 2H), 7.28 (d, J=8.4 Hz, 2H), 8.19 (s, 2H), 8.26 (s, 1H).

Example 10 trans-5-(4-((6-((1-(5-ethylpyrimidin-2-yl)piperidin-4-yl)oxy)-5-methylpyrimidin-4-yl)oxy)phenyl)-1,3,2-dioxathiane 2-oxide $^1$HNMR: δ 1.22 (t, J=7.6 Hz, 3H), 1.81-1.89 (m, 2H), 2.05-2.11 (m, 2H), 2.18 (s, 3H), 2.48 (q, J=7.6 Hz, 2H), 3.08-3.10 (m, 1H), 3.67-3.73 (m, 2H), 4.10 (dd, J=12 & 2.8 Hz, 2H), 4.15-4.21 (m, 2H), 5.20 (dd, J=12.0 & 2.8 Hz, 2H), 5.40-5.44 (m, 1H), 7.15 (d, J=8.4 Hz, 2H), 7.53 (d, J=8.4 Hz, 2H), 8.19 (s, 2H), 8.27 (s, 1H).

Example 11 cis-5-(4-((6-(4-(3-isopropyl-1,2,4-oxadiazol-5-yl) piperidin-1-yl)-5-methylpyrimidin-4-yl)oxy)phenyl)-1,3,2-dioxathiane 2-oxide $^1$HNMR: δ 1.34 (d, J=6.8 Hz, 6H), 2.04-2.11 (m, 2H), 2.19-2.20 (m, 2H), 2.23 (s, 3H), 3.06-3.12 (m, 3H), 3.15-3.21 (m, 1H), 3.58-3.64 (m, 1H), 3.86-3.95 (m, 4H), 4.97 (t, J=11.6 Hz, 2H), 7.12 (d, J=8.4 Hz, 2H), 7.28 (d, J=8.4 Hz, 2H), 8.28 (s, 1H).

Example 12 trans-5-(4-((6-(4-(3-isopropyl-1,2,4-oxadiazol-5-yl) piperidin-1-yl)-5-methylpyrimidin-4-yl)oxy)phenyl)-1,3,2-dioxathiane 2-oxide $^1$HNMR: δ 1.35 (d, J=6.8 Hz, 6H), 2.02-2.11 (m, 2H), 2.20-2.23 (m, 2H), 2.24 (s, 3H), 3.06-3.12 (m, 4H), 3.14-3.21 (m, 1H), 3.86-3.90 (m, 2H), 4.10 (dd, J=11.6 & 2.8 Hz, 2H), 5.20 (dd, J=11.6 & 3.6 Hz, 2H), 7.14 (d, J=8.4 Hz, 2H), 7.52 (d, J=8.8 Hz, 2H), 8.30 (s, 1H).

Example 13 cis-5-(4-((2-(1-(5-ethylpyrimidin-2-yl)piperidin-4-yl)thiazol-4-yl)methoxy)phenyl)-1,3,2-dioxathiane 2-oxide $^1$HNMR: δ 1.19 (t, J=7.6 Hz, 3H), 1.75-1.85 (m, 2H), 2.20 (d, J=11.2 Hz, 2H), 2.45 (q, J=7.6 Hz, 2H), 3.00-3.07 (m, 2H), 3.25-3.32 (m, 1H), 3.48-3.56 (m, 1H), 3.87 (dd, J=11.6 & 4.4 Hz, 2H), 4.82 (d, J=13.2 Hz, 2H), 4.92 (t, J=11.6 Hz, 2H), 5.15 (s, 2H), 6.97 (d, J=8.8 Hz, 2H), 7.14-7.18 (m, MA), 8.18 (s, 2H).

Example 14 trans-5-(4-((2-(1-(5-ethylpyrimidin-2-yl)piperidin-4-yl)thiazol-4-yl)methoxy)phenyl)-1,3,2-dioxathiane 2-oxide $^1$HNMR: δ 1.19 (t, J=7.6 Hz, 3H), 1.79-1.83 (m, 2H), 2.20 (d, J=12.8 Hz, 2H), 2.47 (q, J=7.6 Hz, 2H), 3.00-3.06 (m, 3H), 3.29 (m, 1H), 4.07 (dd, J=12.0 & 3.6 Hz, 2H), 4.83 (d, J=13.6 Hz, 2H), 5.14 (dd, J=12 & 4.0 Hz, 2H), 5.17 (s, 2H), 7.00 (d, J=8.8 Hz, 2H), 7.20 (s, 1H), 7.39 (d, J=8.4 Hz, 2H), 8.18 (s, 2H).

Example 15 cis-tert-butyl 4-((5-methyl-6-(4-(2-oxido-1,3,2-dioxathian-5-yl)phenoxy)pyrimidin-4-yl)oxy)piperidine-1-carboxylate $^1$HNMR: δ 1.48 (s, 9H), 1.78-1.79 (m, 2H), 1.96-1.99 (m, 2H), 2.16 (s, 3H), 3.35-3.40 (m, 2H), 3.55-3.61 (m, 1H), 3.65-3.72 (m, 2H), 3.93 (dd, J=11.6 & 4.4 Hz, 2H), 4.97 (t, J=12 Hz, 2H), 5.32 (m, 1H), 7.13 (d, J=8.8 Hz, 2H), 7.28 (d, J=8.4 Hz, 2H), 8.23 (s, 1H).

Example 16 trans-tert-butyl 4-((5-methyl-6-(4-(2-oxido-1,3,2-dioxathian-5-yl)phenoxy)pyrimidin-4-yl)oxy)piperidine-1-carboxylate $^1$HNMR: δ 1.48 (s, 9H), 1.75-1.82 (m, 2H), 1.96-2.01 (m, 2H), 2.17 (s, 3H), 3.09 (t, J=3.14 Hz, 1H), 3.35-3.41 (m, 2H), 3.70-3.76 (m, 2H), 4.19 (dd, J=12.0 & 3.2 Hz, 2H), 5.20 (dd, J=12.0 & 4.0 Hz, 2H), 5.31-5.35 (m, 1H), 7.14 (d, J=6.4 Hz, 2H), 7.52 (d, J=8.4 Hz, 2H), 8.25 (s, 1H).

Example 17 cis-tert-butyl 4-(4-((4-(2-oxido-1,3,2-dioxathian-5-yl)phenoxy)methyl)thiazol-2-yl)piperidine-1-carboxylate $^1$HNMR: δ 1.47 (s, 9H), 1.68-1.78 (m, 2H), 2.10 (d, J=11.2 Hz, 2H), 2.87 (t, J=11.6 Hz, 2H), 3.13-3.19 (m, 1H), 3.48-3.56 (m, 1H), 3.88 (dd, J=11.6 & 4.8 Hz, 2H), 4.20 (bs, 2H), 4.92 (t, J=11.6 Hz, 2H), 5.30 (s, 2H), 6.98 (d, J=8.4 Hz, 2H), 7.16 (d, J=8.8 Hz, 2H), 7.20 (s, 1H).

Example 18 trans-tert-butyl 4-(4-((4-(2-oxido-1,3,2-dioxathian-5-yl)phenoxy)methyl)thiazol-2-yl)piperidine-1-carboxylate $^1$HNMR: δ 1.47 (s, 9H), 1.68-1.79 (m, 2H), 2.10 (d, J=13.2 Hz, 2H), 2.87 (t, J=11.6 Hz, 2H), 3.04-3.06 (m, 1H), 3.13-3.19 (m, 1H), 4.07 (dd, J=11.6 & 4.0 Hz, 2H), 4.20 (bs, 2H), 5.13-5.175 (m, 4H), 7.00 (d, J=8.8 Hz, 2H), 7.21 (s, 1H), 7.39 (d, J=8.8 Hz, 2H).

Example 19 trans-tert-butyl 4-(2-(4-(2-oxido-1,3,2-dioxathian-5-yl)phenoxy)ethoxy)piperidine-1-carboxylate $^1$HNMR: δ 1.45 (s, 9H), 1.52-1.55 (m, 2H), 1.83-1.86 (m, 2H), 3.04-3.13 (m, 3H), 3.54-3.58 (m, 1H), 3.74-3.78 (m, 2H), 3.82 (t, J=5.2 Hz, 2H), 4.07 (dd, J=12.2 & 3.4 Hz, 2H), 4.12 (t, J=4.8 Hz, 2H), 5.13 (dd, J=12.0 & 4.0 Hz, 2H), 6.91-6.94 (m, 2H), 7.37 (dd, J=11.6 & 2.8 Hz, 21-1).

Example 20 cis-tert-butyl 4-(3-((5-methyl-6-(4-(2-oxido-1,3,2-dioxathian-5-yl)phenoxy)pyrimidin-4-yl)oxy)propyl)piperidine-1-carboxylate $^1$HNMR: δ 1.10-1.41 (m, 2H), 1.39-1.43 (m, 3H), 1.45 (s, 9H), 1.68 (d, J=12.8 Hz, 2H), 1.80-1.84 (m, 2H), 2.15 (s, 3H), 2.68 (m, 2H), 3.59-3.61 (m, 1H), 3.93 (dd, J=12.0 & 4.8 Hz, 2H), 4.08-4.15 (m, 2H), 4.37 (t, J=6.6 Hz, 2H), 4.97 (t, J=12 Hz, 2H), 7.13 (d, J=8.4 Hz, 2H), 7.28 (d, J=8.8 Hz, 2H), 8.25 (s, 1H).

Example 21 trans-tert-butyl 4-(3-((5-methyl-6-(4-(2-oxido-1,3,2-dioxathian-5-yl)phenoxy)pyrimidin-4-yl)oxy)propyl)piperidine-1-carboxylate $^1$HNMR: δ 1.10-1.41 (m, 2H), 1.39-1.42 (m, 3H), 1.46 (s, 9H), 1.67-1.71 (m, 2H), 1.81-1.84 (m, 2H), 2.17 (s, 3H), 2.69 m, 2H), 3.08-3.10 (m, 1H), 4.10 (dd, J=12 & 3.2 Hz, 4H), 4.37 (t, J=6.6 Hz, 2H), 5.20 (dd, J=12.0 & 4.0 Hz, 2H), 7.14 (d, J=8.4 Hz, 2H), 7.52 (d, J=8.4 Hz, 2H), 8.26 (s, 1H).

Example 22 cis-5-(4-(3-((1-(pyrimidin-2-yl)piperidin-4-yl)oxy) propoxy)phenyl)-1,3,2-dioxathiane 2-oxide ¹HNMR: δ 1.17-1.23 (m, 2H), 1.42 (q, J=7.8 Hz, 2H), 1.56-1.59 (m, 1H), 1.79-1.84 (m, 4H), 2.82-2.89 (m, 2H), 3.48-3.54 (m, 1H), 3.87 (dd, J=11.6 & 4.4 Hz, 2H), 3.94 (t, J=6.6 Hz, 2H), 4.74 (d, J=12.8 Hz, 2H), 4.92 (t, J=11.8 Hz, 2H), 6.43 (t, J=4.6 Hz, 1H), 6.87 (d, J=8.8 Hz, 2H), 7.14 (d, J=8.8 Hz, 2H), 8.28 (d, J=4.8 Hz, 2H).

Example 23 trans-5-(4-(3-((1-(pyrimidin-2-yl)piperidin-4-yl)oxy) propoxy)phenyl)-1,3,2-dioxathiane 2-oxide ¹HNMR: δ 1.18-1.22 (m, 2H), 1.43 (q, J=7.2 Hz, 2H), 1.57-1.60 (m, 1H), 1.79-1.86 (m, 4H), 2.86 (t, J=12.7 Hz, 2H), 3.05 (t, J=3.8 Hz, 1H), 3.96 (t, J=6.4 Hz, 2H), 4.08 (dd, J=11.6 & 3.6 Hz, 2H), 4.74 (d, J=13.6 Hz, 2H), 5.12 (dd, J=12.0 & 4.0 Hz, 2H), 6.43 (t, J=4.6 Hz, 1H), 6.90 (d, J=8.8 Hz, 2H), 7.37 (d, J=8.4 Hz, 2H), 8.28 (d, J=4.4 Hz, 2H).

Example 24 cis-tert-butyl-4-((5-methyl-6-(4-((2-oxido-1,3,2-dioxathian-5-yl)methyl)phenoxy)pyrimidin-4-yl) oxy)piperidine-1-carboxylate ¹HNMR: δ 1.48 (s, 9H), 1.74-1.81 (m, 2H), 1.95-2.00 (m, 2H), 2.16 (s, 3H), 2.49 (d, J=7.6 Hz, 2H), 2.67-2.73 (m, 1H), 3.34-3.41 (m, 2H), 3.70-3.75 (m, 2H), 3.79 (dd, J=11.6 & 4.4 Hz, 2H), 4.62 (t, J=11.6 Hz, 2H), 5.30-5.34 (m, 1H), 7.07 (d, J=8.4 Hz, 2H), 7.17 (d, J=8.4 Hz, 2H), 8.23 (s, 1H).

Example 25 trans-tert-butyl-4-((5-methyl-6-(4-((2-oxido-1,3,2-dioxathian-5-yl)methyl)phenoxy)pyrimidin-4-yl) oxy)piperidine-1-carboxylate ¹HNMR: δ 1.48 (s, 9H), 1.73-1.81 (m, 2H), 1.88-1.92 (m, 1H), 1.95-2.00 (m, 2H), 2.16 (s, 3H), 3.14 (d, J=8.0 Hz, 2H), 3.34-3.41 (m, 2H), 3.68-3.75 (m, 4H), 5.04-5.07 (m, 2H), 5.29-5.34 (m, 1H), 7.08 (d, J=8.4 Hz, 2H), 7.26 (d, J=8.4 Hz, 2H), 8.23 (s, 1H).

Example 26 tert-butyl 4-((5-methyl-6-(4-((2-oxido-1,3,2-dioxathiolan-4-yl)methyl)phenoxy)pyrimidin-4-yl)oxy) piperidine-1-carboxylate ¹HNMR: δ 1.48 (s, 9H), 1.74-1.81 (m, 2H), 1.95-2.00 (m, 2H), 2.16 (s, 3H), 3.08-3.14 (m, 1H), 3.33-3.41 (m, 3H), 3.69-3.75 (m, 2H), 4.08 (m, 1H), 4.48 (d, J=7.2 Hz, 1H), 4.66 (m, 1H), 5.30-5.34 (m, 1H), 7.09 (d, J=8.8 Hz, 2H), 7.25-7.30 (m, 2H), 8.23 (s, 1H).

Example 27 cis-isobutyl 4-((5-methyl-6-(4-(2-oxido-1,3,2-dioxathian-5-yl)phenoxy)pyrimidin-4-yl)oxy)piperidine-1-carboxylate ¹HNMR: δ 0.95 (d, J=6.8 Hz, 6H), 1.77-1.84 (m, 2H), 1.92-2.02 (m, 3H), 2.16 (s, 3H), 3.42-3.48 (m, 2H), 3.58-3.64 (m, 1H), 3.74-3.80 (m, 2H), 3.88 (d, J=6.8 Hz, 2H), 3.93 (dd, J=11.6 & 4.4 Hz, 2H), 4.97 (t, J=11.6 Hz, 2H), 5.33-5.37 (m, 1H), 7.13 (d, J=8.8 Hz, 2H), 7.28 (d, J=8.4 Hz, 2H), 8.24 (s, 1H).

Example 28 trans-isobutyl 4-((5-methyl-6-(4-(2-oxido-1,3,2-dioxathian-5-yl)phenoxy)pyrimidin-4-yl)oxy)piperidine-1-carboxylate ¹HNMR: δ 0.95 (d, J=6.8 Hz, 6H), 1.76-1.85 (m, 2H), 1.90-2.03 (m, 3H), 2.18 (s, 3H), 3.07-3.11 (m, 1H), 3.42-3.48 (m, 2H), 3.74-3.80 (m, 2H), 3.88 (d, J=6.8 Hz, 2H), 4.09 (dd, J=12.0 & 2.8 Hz, 2H), 5.20 (dd, J=12 & 3.6 Hz, 2H), 5.32-5.38 (m, 1H), 7.14 (d, J=8.8 Hz, 2H), 7.53 (d, J=8.8 Hz, 2H), 8.25 (s, 1H).

Example 29 cis-5-(4-((6-((1-(3-isopropyl-1,2,4-oxadiazol-5-yl) piperidin-4-yl)oxy)-5-methylpyrimidin-4-yl)oxy) benzyl)-1,3,2-dioxathiane 2-oxide ¹HNMR: δ 1.29 (d, J=7.2 Hz, 6H), 1.91-1.98 (m, 2H), 2.07-2.12 (m, 2H), 2.17 (s, 3H), 2.49 (d, J=8.0 Hz, 2H), 2.67-2.73 (m, 1H), 2.87-2.93 (m, 1H), 3.61-3.68 (m, 2H), 3.78-3.88 (m, 4H), 4.62 (t, J=11.6 Hz, 2H), 5.40-5.43 (m, 1H), 7.07 (d, J=8.4 Hz, 2H), 7.17 (d, J=8.4 Hz, 2H), 8.24 (s, 1H).

Example 30 trans-5-(4-((6-((1-(3-isopropyl-1,2,4-oxadiazol-5-yl) piperidin-4-yl)oxy)-5-methylpyrimidin-4-yl)oxy) benzyl)-1,3,2-dioxathiane 2-oxide ¹HNMR: δ 1.29 (d, J=7.2 Hz, 6H), 1.88-1.98 (m, 3H), 2.06-2.13 (m, 2H), 2.18 (s, 3H), 2.87-2.94 (m, 1H), 3.14 (d, J=8.4 Hz, 2H), 3.61-3.68 (m, 4H), 3.82-3.88 (m, 2H), 5.07 (dd, J=12.0 & 1.2 Hz, 2H), 5.40-5.44 (m, 1H), 7.09 (d, J=8.4 Hz, 2H), 7.269 (d, J=6.4 Hz, 2H), 8.24 (s, 1H).

Example 31 cis-5-(4-((6-((1-(5-ethylpyrimidin-2-yl)piperidin-4-yl)oxy)-5-methylpyrimidin-4-yl)oxy)benzyl)-1,3,2-dioxathiane 2-oxide ¹HNMR: δ 1.21 (t, J=7.6 Hz, 3H), 1.81-1.88 (m, 2H), 2.05-2.11 (m, 2H), 2.17 (s, 3H), 2.44-2.50 (m, 4H), 2.67-2.72 (m, 1H), 3.67-3.73 (m, 2H), 3.81 (dd, J=12.0 & 4.4 Hz, 2H), 4.15-4.21 (m, 2H), 4.62 (t, J=11.6 Hz, 2H), 5.40-5.44 (m, 1H), 7.08 (d, J=8.8 Hz, 2H), 7.17 (d, J=8.4 Hz, 2H), 8.19 (s, 2H), 8.25 (s, 1H).

Example 32 trans-5-(4-((6-((1-(5-ethylpyrimidin-2-yl)piperidin-4-yl)oxy)-5-methylpyrimidin-4-yl)oxy)benzyl)-1,3,2-dioxathiane 2-oxide ¹HNMR: δ 1.20 (t, J=7.6 Hz, 3H), 1.83-1.88 (m, 3H), 2.05-2.08 (m, 2H), 2.17 (s, 3H), 2.44-2.50 (q, J=7.6 Hz, 2H), 3.14 (d, J=8.4 Hz, 2H), 3.67-3.73 (m, 4H), 4.15-4.20 (m, 2H), 5.06 (dd, J=10.4 & 1.2 Hz, 2H), 5.44 (m, 1H), 7.09 (d, J=8.4 Hz, 2H), 7.26 (d, J=8.4 Hz, 2H), 8.19 (s, 2H), 8.25 (s, 1H).

Example 33 cis-ethyl 4-((5-methyl-6-(4-(2-oxido-1,3,2-dioxathian-5-yl)phenoxy)pyrimidin-4-yl)oxy)piperidine-1-carboxylate ¹HNMR: δ 1.28 (t, J=7.2 Hz, 3H), 1.78-1.82 (m, 2H), 1.97-2.01 (m, 2H), 2.18 (s, 3H), 3.41-3.47 (m, 2H), 3.58-3.62 (m, 1H), 3.73-3.78 (m, 2H), 3.93 (dd, J=11.6 & 4.4 Hz, 2H), 4.15 (q, J=7.2 Hz, 2H), 4.97 (t, J=3.6 Hz, 2H), 5.33-5.35 (m, 1H), 7.13 (d, J=8.8 Hz, 2H), 7.28 (d, J=8.4 Hz, 2H), 8.24 (s, 1H).

Example 34 trans-ethyl 4-((5-methyl-6-(4-(2-oxido-1,3,2-dioxathian-5-yl)phenoxy)pyrimidin-4-yl)oxy)piperidine-1-carboxylate ¹HNMR: δ 1.28 (t, J=7.2 Hz, 3H), 1.77-1.84 (m, 2H), 1.97-2.01 (m, 2H), 2.18 (s, 3H), 3.08-3.10 (m, 1H), 3.41-3.47 (m, 2H), 3.74-3.79 (m, 2H), 4.10 (dd, J=12.0 & 4.0 Hz, 2H), 4.15 (q, J=7.2 Hz, 2H), 5.20 (dd, J=12.4 & 4.0 Hz, 2H), 5.33-5.37 (m, 1H), 7.13-7.16 (m, 2H), 7.53 (d, J=8.4 Hz, 2H), 8.25 (s, 1H).

Example 35 cis-benzyl 4-((5-methyl-6-(4-(2-oxido-1,3,2-dioxathian-5-yl)phenoxy)pyrimidin-4-yl)oxy)piperidine-1-carboxylate ¹HNMR: δ 1.82 (bs, 2H), 1.99 (bs, 2H), 2.16 (s, 3H), 3.45-3.51 (m, 2H), 3.57-3.65 (m, 1H), 3.76-3.82 (m, 2H), 3.93 (dd, J=11.6 & 4.4 Hz, 2H), 4.97 (t, J=12.0 Hz, 2H), 5.15 (s, 2H), 5.32-5.37 (m, 1H), 7.13 (d, J=8.8 Hz, 2H), 7.26-7.29 (m, 2H), 7.31-7.38 (m, 5H), 8.23 (s, 1H).

Example 36 trans-benzyl 4-((5-methyl-6-(4-(2-oxido-1,3,2-dioxathian-5-yl)phenoxy)pyrimidin-4-yl)oxy)piperidine-1-carboxylate ¹HNMR: δ 1.82 (bs, 2H), 1.99-2.01 (m, 2H), 2.17 (s, 3H), 3.09 (t, J=3.2 Hz, 1H), 3.46-3.52 (m, 2H), 3.76-3.82 (m, 2H), 4.10 (dd, J=12.4 & 3.2 Hz, 2H), 5.15 (s, 2H), 5.20 (dd, J=12 & 3.6 Hz, 2H), 5.33-5.37 (m, 1H), 7.13-7.16 (m, 2H), 7.32-7.38 (m, 5H), 7.53 (d, J=8.4 Hz, 2H), 8.24 (s, 1H).

Example 37 cis-5-(4-(((6-((1-benzylpiperidin-4-yl)oxy)-5-methylpyrimidin-4-yl)oxy)phenyl)-1,3,2-dioxathiane 2-oxide ¹HNMR: δ 1.80 (bs, 2H), 2.04 (bs, 2H), 2.15 (s, 3H), 2.30 (bs, 2H), 2.73 (bs, 2H), 3.55-3.65 (m, 3H), 3.91 (dd, J=11.6 & 4.4 Hz, 2H), 4.97 (t, J=12 Hz, 2H), 5.19 (bs, 1H), 7.12 (d, J=8.8 Hz, 2H), 7.26-7.28 (m, 3H), 7.33-7.34 (m, 4H), 8.23 (s, 1H).

Example 38 trans-5-(4-(((6-((1-benzylpiperidin-4-yl)oxy)-5-methylpyrimidin-4-yl)oxy)phenyl)-1,3,2-dioxathiane 2-oxide ¹HNMR: δ 1.90 (bs, 2H), 1.97-2.04 (m, 2H), 2.16 (s, 3H), 2.35-2.45 (m, 2H), 2.77 (bs, 2H), 3.07-3.10 (m, 1H), 3.55-3.65 (m, 2H), 4.10 (dd, J=11.6 & 4.4 Hz, 2H), 5.18-5.22 (m, 3H), 7.11-7.15 (m, 2H), 7.28-7.30 (m, 2H), 7.32-7.36 (m, 3H), 7.52 (d, J=8.0 Hz, 2H), 8.24 (s, 1H).

Example 39 cis-ethyl 4-((5-methyl-6-(4-((2-oxido-1,3,2-dioxathian-5-yl)methyl)phenoxy)pyrimidin-4-yl)oxy)piperidine-1-carboxylate ¹HNMR: δ 1.28 (t, J=7.2 Hz, 3H), 1.77-1.83 (m, 2H), 1.97-2.02 (m, 2H), 2.16 (s, 3H), 2.49 (d, J=7.6 Hz, 2H), 2.67-2.71 (m, 1H), 3.41-3.47 (m, 2H), 3.75-3.76 (m, 2H), 3.80 (dd, J=11.6 & 4.0 Hz, 2H), 4.15 (q, J=7.2 Hz, 2H), 4.62 (t, J=11.6 Hz, 2H), 5.32-5.36 (m, 1H), 7.07 (d, J=8.4 Hz, 2H), 7.17 (d, J=8.4 Hz, 2H), 8.23 (s, 1H).

Example 40 trans-ethyl 4-((5-methyl-6-(4-((2-oxido-1,3,2-dioxathian-5-yl)methyl)phenoxy)pyrimidin-4-yl)oxy)piperidine-1-carboxylate ¹HNMR: δ 1.28 (t, J=7.2 Hz, 3H), 1.75-1.83 (m, 2H), 1.88-1.92 (m, 1H), 1.97-2.02 (m, 2H), 2.17 (s, 3H), 3.14 (d, J=8.0 Hz, 2H), 3.41-3.47 (m, 2H), 3.69 (d, J=10.8 Hz, 2H), 3.74-3.78 (m, 2H), 4.16 (q, J=7.2 Hz, 2H), 5.06 (dd, J=11.6 & 2.4 Hz, 2H), 5.32-5.36 (m, 1H), 7.08 (d, J=8.8 Hz, 2H), 7.26 (d, J=8.4 Hz, 2H), 8.23 (s, 1H).

Example 41 cis-5-(4-((5-methyl-6-((1-(pyrimidin-2-yl)piperidin-4-yl)oxy)pyrimidin-4-yl)oxy)benzyl)-1,3,2-dioxathiane 2-oxide ¹HNMR: δ 1.83-1.89 (m, 2H), 2.04-2.10 (m, 2H), 2.17 (s, 3H), 2.49 (d, J=7.6 Hz, 2H), 2.67-2.72 (m, 1H), 3.72-3.78 (m, 2H), 3.82 (dd, J=11.6 & 4.4 Hz, 2H), 4.17-4.23 (m, 2H), 4.62 (t, J=11.6 Hz, 2H), 5.41-5.45 (m, 1H), 6.49 (t, J=4.8 Hz, 1H), 7.08 (d, J=8.4 Hz, 2H), 7.17 (d, J=8.4 Hz, 2H), 8.25 (s, 1H), 8.32 (d, J=4.8 Hz, 2H).

Example 42 trans-5-(4-((5-methyl-6-((1-(pyrimidin-2-yl)piperidin-4-yl)oxy)pyrimidin-4-yl)oxy)benzyl)-1,3,2-dioxathiane 2-oxide ¹HNMR: δ 1.81-1.90 (m, 3H), 2.04-2.10 (m, 2H), 2.17 (s, 3H), 3.14 (d, J=8.0 Hz, 2H), 3.69 (d, J=11.2 Hz, 2H), 3.73-3.78 (m, 2H), 4.17-4.23 (m, 2H), 5.04-5.07 (m, 2H), 5.41-5.45 (m, 1H), 6.49 (t, J=4.8 Hz, 1H), 7.09 (d, J=8.4 Hz, 2H), 7.26 (d, J=8.0 Hz, 2H), 8.26 (s, 1H), 8.32 (d, J=4.8 Hz, 2H).

Example 43 cis-isobutyl 4-((5-methyl-6-(4-((2-oxido-1,3,2-dioxathian-5-yl)methyl)phenoxy)pyrimidin-4-yl)oxy)piperidine-1-carboxylate $^1$HNMR: δ 0.95 (d, J=6.8 Hz, 6H), 1.78-1.82 (m, 2H) 1.93-2.01 (m, 3H), 2.17 (s, 3H), 2.49 (d, J=5.6 Hz, 2H), 2.68-2.72 (m, 1H), 3.42-3.48 (m, 2H), 3.75-3.83 (m, 4H), 3.88 (d, J=6.4 Hz, 2H), 4.62 (t, J=11.6 Hz, 2H), 5.33-5.36 (m, 1H), 7.07 (d, J=8.0 Hz, 2H), 7.17 (d, J=8.4 Hz, 2H), 8.23 (s, 1H).

Example 44 trans-isobutyl 4-((5-methyl-6-(4-((2-oxido-1,3,2-dioxathian-5-yl)methyl)phenoxy)pyrimidin-4-yl)oxy)piperidine-1-carboxylate $^1$HNMR: δ0.95 (d, J=6.8 Hz, 6H), 1.79-1.81 (m, 2H), 1.90-1.98 (m, 4H), 2.17 (s, 3H), 3.14 (d, J=8.0 Hz, 2H), 3.43-3.48 (m, 2H), 3.69 (d, J=11.6 Hz, 2H), 3.75-3.78 (m, 2H), 3.88 (d, J=6.8 Hz, 2H), 5.06 (d, J=8.0 Hz, 2H), 5.34-5.35 (m, 1H), 7.08 (d, J=8.0 Hz, 2H), 7.26 (s, 2H), 8.23 (s, 1H).

Example 45 cis-N-(2,4-dichlorophenyl)-4-((5-methyl-6-(4-(2-oxido-1,3,2-dioxathian-5-yl)phenoxy)pyrimidin-4-yl)oxy)piperidine-1-carboxamide $^1$HNMR: δ 1.91 (bs, 2H), 2.08 (bs, 2H), 2.17 (s, 3H), 3.15 (s, 2H), 3.42 (m, 1H), 3.50 (bs, 2H), 3.92 (dd, J=11.6 & 4.4 Hz, 2H), 4.97 (t, J=12 Hz, 2H), 5.43 (bs, 1H), 6.43 (bs, 1H), 7.13 (d, J=8.8 Hz, 2H), 7.21 (d, J=8.4 Hz, 1H), 7.28-7.32 (m, 3H), 7.6 (s, 1H), 8.25 (s, 1H).

Example 46 trans-N-(2,4-dichlorophenyl)-4-((5-methyl-6-(4-(2-oxido-1,3,2-dioxathian-5-yl)phenoxy)pyrimidin-4-yl)oxy)piperidine-1-carboxamide $^1$HNMR: δ 1.91 (bs, 2H), 2.00 (s, 2H), 2.17 (s, 3H), 3.00-3.09 (m, 1H), 3.50 (bs, 2H), 3.75 (bs, 2H), 4.10 (dd, J=11.6 & 4.4 Hz, 2H), 5.21 (dd, J=12 & 4.0 Hz, 2H), 5.41 (bs, 1H), 6.50 (s, 1H), 7.15 (d, J=8.8 Hz, 2H), 7.21 (d, J=8.4 Hz, 1H), 7.28 (d, J=8.4 Hz, 1H), 7.33 (d, J=8.8 Hz, 1H), 7.53 (d, J=6.8 Hz, 2H), 7.60 (s, 1H), 8.26 (s, 1H).

Example 47 cis-isopropyl 4-((5-methyl-6-(4-(2-oxido-1,3,2-dioxathian-5-yl)phenoxy)pyrimidin-4-yl)oxy)piperidine-1-carboxylate $^1$HNMR: δ 1.26 (d, J=6.4 Hz, 6H), 1.76-1.81 (m, 2H), 1.96-2.00 (m, 2H), 2.16 (s, 3H), 3.39-3.45 (m, 2H), 3.58-3.64 (m, 1H), 3.74-3.78 (m, 2H), 3.93 (dd, J=11.6 & 4.4 Hz, 2H), 4.90-4.94 (m, 1H), 4.97 (t, J=11.6 Hz, 2H), 5.32-5.36 (m, 1H), 7.13 (d, J=8.4 Hz, 2H), 7.28 (d, J=8.4 Hz, 2H), 8.24 (s, 1H).

Example 48 trans-isopropyl 4-((5-methyl-6-(4-(2-oxido-1,3,2-dioxathian-5-yl)phenoxy)pyrimidin-4-yl)oxy)piperidine-1-carboxylate $^1$HNMR: δ 1.27 (d, J=6.4 Hz, 6H), 1.76-1.82 (m, 2H), 1.99-2.02 (m, 2H), 2.19 (s, 3H), 3.10 (t, J=3.2 Hz, 1H), 3.40-3.47 (m, 2H), 3.76-3.79 (m, 2H), 4.11 (dd, J=12.0 & 4.0 Hz, 2H), 4.92-4.98 (m, 1H), 5.22 (dd, J=12.0 & 3.6 Hz, 2H), 5.34-5.37 (m, 1H), 7.16 d, J=8.8 Hz, 2H), 7.54 (d, J=8.4 Hz, 2H), 8.26 (s, 1H).

Example 49 cis-isopropyl 4-((5-methyl-6-(4-((2-oxido-1,3,2-dioxathian-5-yl)methyl)phenoxy)pyrimidin-4-yl)oxy)piperidine-1-carboxylate $^1$HNMR: δ 1.26 (d, J=6.4 Hz, 6H), 1.77-1.80 (m, 2H), 1.96-2.00 (m, 2H), 2.16 (s, 3H), 2.49 (d, J=7.60 Hz, 2H), 2.67-2.73 (m, 1H), 3.39-3.45 (m, 2H), 3.74-3.76 (m, 2H), 3.81 (dd, J=11.6 & 4.4 Hz, 2H), 4.62 (t, J=11.6 Hz, 2H), 4.90-4.97 (m, 1H), 5.32-5.35 (m, 1H), 7.07 (d, J=8.4 Hz, 2H), 7.17 (d, J=8.4 Hz, 2H), 8.23 (s, 1H).

Example 50 trans-isopropyl 4-((5-methyl-6-(4-((2-oxido-1,3,2-dioxathian-5-yl)methyl)phenoxy)pyrimidin-4-yl)oxy)piperidine-1-carboxylate $^1$HNMR: δ 1.26 (d, J=6.4 Hz, 6H), 1.76-1.82 (m, 2H), 1.90-1.92 (m, 1H), 1.97-1.98 (m, 2H), 2.17 (s, 3H), 3.14 (d, J=8.0 Hz, 2H), 3.39-3.45 (m, 2H), 3.70 (d, J=10.8 Hz, 2H), 3.74-3.76 (m, 2H), 4.92-4.95 (m, 1H), 5.06 (dd, J=12.0 & 2.8 Hz, 2H), 5.32-5.35 (m, 1H), 7.08 (d, J=8.4 Hz, 2H), 7.26 (d, J=8.4 Hz, 2H), 823 (s, 1H).

Example 51 cis-tert-butyl 4-(4-((2-oxido-1,3,2-dioxathian-5-yl)methyl)phenoxy)piperidine-1-carboxylate $^1$HNMR: δ 1.46 (s, 9H), 1.71-1.77 (m, 2H), 1.88-1.93 (m, 2H), 2.42 (d, J=7.6 Hz, 2H), 2.62-2.65 (m, 1H), 3.30-3.36 (m, 2H), 3.66-3.75 (m, 2H), 3.74-3.78 (m, 2H), 4.41-4.44 (m, 1H), 4.62 (t, J=11.6 Hz, 2H), 6.84-6.86 (m, 2H), 7.02 (d, J=1.2 Hz, 2H).

Example 52 trans-tert-butyl 4-(4-((2-oxido-1,3,2-dioxathian-5-yl)methyl)phenoxy)piperidine-1-carboxylate $^1$HNMR: δ 1.46 (s, 9H), 1.70-1.77 (m, 2H), 1.82-1.93 (m, 3H), 3.06 (d, J=8.0 Hz, 2H), 3.29-3.36 (m, 2H), 3.67 (dd, J=12.0 & 4.4 Hz, 2H), 3.68 (m, 2H), 4.41-4.45 (m, 1H), 5.01-5.04 (m, 2H), 6.87 (d, J=8.8 Hz, 2H), 7.12 (d, J=8.4 Hz, 2H).

Example 53 cis-5-(4-((1-(3-isopropyl-1,2,4-oxadiazol-5-yl)piperidin-4-yl)oxy)benzyl)-1,3,2-dioxathiane 2-oxide $^1$HNMR: δ 1.28 (d, J=6.8 Hz, 6H), 1.89-1.95 (m, 2H), 1.98-2.03 (m, 2H), 2.42 (d, J=7.6 Hz, 2H), 2.62-2.67 (m, 1H), 2.86-2.92 (m, 1H), 3.59-3.65 (m, 2H), 3.74-3.84 (m, 4H), 4.52-4.55 (m, 1H), 4.60 (t, J=11.6 Hz, 2H), 6.84-6.86 (m, 2H), 7.04 (d, J=11.2 Hz, 2H).

Example 54 trans-5-(4-((1-(3-isopropyl-1,2,4-oxadiazol-5-yl)piperidin-4-yl)oxy)benzyl)-1,3,2-dioxathiane 2-oxide ¹HNMR: δ 1.28 (d, J=6.8 Hz, 6H), 1.82-1.85 (m, 1H), 1.89-1.95 (m, 2H), 1.98-2.04 (m, 2H), 2.86-2.92 (m, 1H), 3.07 (d, J=8.0 Hz, 2H), 3.59-3.67 (m, 4H), 3.77-3.83 (m, 2H), 4.53-4.56 (m, 1H), 5.02-5.05 (m, 2H), 6.88 (d, J=8.8 Hz, 2H), 7.14 (d, J=8.8 Hz, 2H).

Example 55 cis-tert-butyl 4-(4-((4-((2-oxido-1,3,2-dioxathian-5-yl)methyl)phenoxy)methyl)thiazol-2-yl)piperidine-1-carboxylate ¹HNMR: δ 1.47 (s, 9H), 1.71-1.75 (m, 2H), 2.10 (d, J=11.6 Hz, 2H), 2.43 (d, J=7.6 Hz, 2H), 2.63-2.65 (m, 1H), 2.85-2.87 (m, 2H), 3.13-3.19 (m, 1H), 3.75 (dd, J=11.6 & 4.4 Hz, 2H), 4.15-4.25 (m, 2H), 4.59 (t, J=11.6 Hz, 2H), 5.14 (s, 2H), 6.92-6.95 (m, 2H), 7.04 (d, J=8.4 Hz, 2H), 7.21 (s, 1H).

Example 56 trans-tert-butyl 4-(4-((4-((2-oxido-1,3,2-dioxathian-5-yl)methyl)phenoxy)methyl)thiazol-2-yl)piperidine-1-carboxylate ¹HNMR: δ 1.47 (s, 9H), 1.71-1.77 (m, 2H), 1.84 (t, J=4.0 Hz, 1H), 2.10 (d, J=14.4 Hz, 2H), 2.85-2.89 (m, 2H), 3.07 (d, J=8.4 Hz, 2H), 3.13-3.19 (m, 1H), 3.66 (dd, J=12.0 & 1.6 Hz, 2H), 4.15-4.25 (m, 2H), 5.01-5.05 (m, 2H), 5.15 (s, 2H), 6.96 (d, J=4.8 Hz, 2H), 7.14 (d, J=8.8 Hz, 2H), 7.21 (s, 1H).

Example 57 cis-tert-butyl 4-(2-methoxy-4-((2-oxido-1,3,2-dioxathian-5-yl)methyl)phenoxy)piperidine-1-carboxylate ¹HNMR: δ 1.46 (s, 9H), 1.74-1.77 (m, 2H), 1.88-1.90 (m, 2H), 2.42 (d, J=8.0 Hz, 2H), 2.60-2.75 (m, 1H), 3.20-3.26 (m, 2H), 3.74-3.78 (m, 4H), 3.83 (s, 3H), 4.33-4.37 (m, 1H), 4.60 (t, J=11.6 Hz, 2H), 6.61-6.64 (m, 2H), 6.85 (d, J=8.0 Hz, 1H).

Example 58 trans-tert-butyl 4-(2-methoxy-4-((2-oxido-1,3,2-dioxathian-5-yl)methyl)phenoxy)piperidine-1-carboxylate ¹HNMR: δ 1.46 (s, 9H), 1.72-1.79 (m, 2H), 1.85-1.93 (m, 3H), 3.06 (d, J=8.4 Hz, 2H), 3.19-3.26 (m, 2H), 3.68 (dd, J=11.6 & 1.2 Hz, 2H), 3.78-3.81 (m, 2H), 3.84 (s, 3H), 4.33-4.37 (m, 1H), 5.02-5.06 (m, 2H), 6.71-6.74 (m, 2H), 6.88 (d, J=8.0 Hz, 1H).

Example 59 cis-5-(4-((1-(5-ethylpyrimidin-2-yl)piperidin-4-yl)oxy)benzyl)-1,3,2-dioxathiane 2-oxide ¹HNMR: δ 1.2 (t, J=7.6 Hz, 3H), 1.77-1.84 (m, 2H), 1.98-2.04 (m, 2H), 2.41-2.49 (m, 4H), 2.61-2.69 (m, 1H), 3.59-3.65 (m, 2H), 3.77 (dd, J=11.6 & 4.4 Hz, 2H), 4.14-4.20 (m, 2H), 4.48-4.54 (m, 1H), 4.60 (t, J=11.6 Hz, 2H), 6.88 (d, J=8.8 & 2.0 Hz, 2H), 7.04 (d, J=8.8 Hz, 2H), 8.18 (s, 2H).

Example 60 trans-5-(4-((1-(5-ethylpyrimidin-2-yl)piperidin-4-yl)oxy)benzyl)-1,3,2-dioxathiane 2-oxide ¹HNMR: δ 1.2 (t, J=7.60 Hz, 3H), 7.149-1.85 (m, 3H), 1.98-2.05 (m, 2H), 2.46 (q, J=15.2 Hz, 2H), 3.06 (d, J=8.0 Hz, 2H), 3.59-3.63 (m, 2H), 3.68 (d, J=10.4 & 1.6 Hz, 2H), 4.14-4.19 (m, 2H), 4.49-4.54 (m, 1H), 5.02-5.05 (m, 2H), 6.88-6.92 (m, 2H), 7.12 (dd, J=8.8 & 2.8 Hz, 2H), 8.18 (s, 2H).

Example 61 cis-5-(3-chloro-4-((6-((1-(3-isopropyl-1,2,4-oxadiazol-5-yl)piperidin-4-yl)oxy)-5-methylpyrimidin-4-yl)oxy)benzyl)-1,3,2-dioxathiane 2-oxide ¹HNMR: δ 1.26 (d, J=6.0 Hz, 6H), 1.91-1.99 (m, 2H), 2.07-2.14 (m, 2H), 2.18 (s, 3H), 2.49 (d, J=7.6 Hz, 2H), 2.68-2.74 (m, 1H), 2.87-2.94 (m, 1H), 3.61-3.68 (m, 2H), 3.79-3.89 (m, 4H), 4.62 (t, J=11.6 Hz, 2H), 5.40-5.43 (m, 1H), 7.07 (d, J=8.4 Hz, 1H), 7.17 (d, J=8.4 Hz, 1H), 7.26 (s, 1H), 8.20 (s, 1H).

Example 62 trans-5-(3-chloro-4-((6-((1-(3-isopropyl-1,2,4-oxadiazol-5-yl)piperidin-4-yl)oxy)-5-methylpyrimidin-4-yl)oxy)benzyl)-1,3,2-dioxathiane 2-oxide ¹HNMR: δ 1.29 (d, J=6.8 Hz, 6H), 1.89-1.99 (m, 3H), 1.91-1.99 (m, 2H), 2.21 (s, 3H), 2.87-2.94 (m, 1H), 3.14 (d, J=8.0 Hz, 2H), 3.61-3.69 (m, 4H), 3.83-3.89 (m, 2H), 5.06-5.10 (m, 2H), 5.40-5.44 (m, 1H), 7.21 (s, 2H), 7.34 (s, 1H), 8.24 (s, 1H).

Example 63 cis-tert-butyl 4-((6-(2-chloro-4-((2-oxido-1,3,2-dioxathian-5-yl)methyl)phenoxy)-5-methylpyrimidin-4-yl)oxy)piperidine-1-carboxylate ¹HNMR: δ 1.48 (s, 9H), 1.76-1.96 (m, 2H), 1.97-2.01 (m, 2H), 2.20 (s, 3H), 2.48 (d, J=7.2 Hz, 2H), 2.69-2.72 (m, 1H), 3.34-3.40 (m, 2H), 3.71-3.75 (m, 2H), 3.82 (dd, J=12.0 & 4.4 Hz, 2H), 4.62 (t, J=11.6 Hz, 2H), 5.30-5.34 (m, 1H), 7.07-7.10 (m, 1H), 7.16 (d, J=8.0 Hz, 1H), 7.26 (s, 1H), 8.19 (s, 1H).

Example 64 trans-tert-butyl 4-((6-(2-chloro-4-((2-oxido-1,3,2-dioxathian-5-yl)methyl)phenoxy)-5-methylpyrimidin-4-yl)oxy)piperidine-1-carboxylate ¹HNMR: δ 1.48 (s, 9H), 1.76-1.81 (m, 2H), 1.97-2.01 (m, 3H), 2.20 (s, 3H), 3.14 (d, J=8 Hz, 2H), 3.34-3.40 (m, 2H), 3.66-3.74 (m, 4H), 5.06-5.10 (m, 2H), 5.30-5.34 (m, 1H), 7.18 (s, 2H), 7.34 (s, 1H), 8.20 (s, 1H).

Example 65 cis-isobutyl 4-((6-(2-chloro-4-(2-oxido-1,3,2-dioxathian-5-yl)phenoxy)-5-methylpyrimidin-4-yl)oxy)piperidine-1-carboxylate ¹HNMR: δ 0.95 (d, J=6.8 Hz, 6H), 1.80-1.83 (m, 2H), 1.92-2.02 (m, 3H), 2.16 (s, 3H), 3.41-3.48 (m, 2H), 3.57-3.64 (m, 1H), 3.76-3.80 (m, 2H), 3.88 (d, J=6.8 Hz, 2H), 3.94 (dd, J=11.6 & 4.4 Hz, 2H), 4.96-4.98 (m, 2H), 5.33-5.36 (m, 1H), 7.14 (s, 1H), 7.28 (s, 1H), 7.36 (s, 1H), 8.24 (s, 1H).

Example 66 trans-isobutyl 4-((6-(2-chloro-4-(2-oxido-1,3,2-dioxathian-5-yl)phenoxy)-5-methylpyrimidin-4-yl)oxy)piperidine-1-carboxylate ¹HNMR: δ 0.95 (d, J=6.8 Hz, 6H), 1.80-1.83 (m, 2H), 1.93-2.00 (m, 3H), 2.18 (s, 3H), 3.02 (m, 1H), 3.42-3.48 (m, 2H), 3.75-3.79 (m, 2H), 3.88 (d, J=6.8 Hz, 2H), 4.06 (dd, J=11.6 & 4.4 Hz, 2H), 5.26 (dd, J=12.0 & 3.6 Hz, 2H), 5.33-5.36 (m, 1H), 7.24 (s, 1H), 7.44 (dd, J=8.4 & 2.0 Hz, 1H), 7.64 (d, J=2.4 Hz, 1H), 8.21 (s, 1H).

Example 67 cis-isobutyl 4-((6-(2-chloro-4-((2-oxido-1,3,2-dioxathian-5-yl)methyl)phenoxy)-5-methylpyrimidin-4-yl)oxy)piperidine-1-carboxylate ¹HNMR: δ 0.95 (d, J=6.8 Hz, 6H), 1.78-1.85 (m, 2H), 1.92-2.03 (m, 3H), 2.17 (s, 3H), 2.48 (d, J=7.6 Hz, 2H), 2.66-2.74 (m, 1H), 3.41-3.48 (m, 2H), 3.75-3.80 (m, 4H), 3.88 (d, J=6.8 Hz, 2H), 4.62 (t, J=11.6 Hz, 2H), 5.32-5.37 (m, 1H), 7.06-7.10 (m, 1H), 7.16 (d, J=8.0 Hz, 1H), 7.36 (s, 1H), 8.19 (s, 1H).

Example 68 trans-isobutyl 4-((6-(2-chloro-4-((2-oxido-1,3,2-dioxathian-5-yl)methyl)phenoxy)-5-methylpyrimidin-4-yl)oxy)piperidine-1-carboxylate ¹HNMR: δ 0.95 (d, J=6.8 Hz, 6H), 1.78-1.83 (m, 2H), 1.92-2.03 (m, 4H), 2.17 (s, 3H), 3.14 (d, J=8.0 Hz, 2H), 3.42-3.48 (m, 2H), 3.68 (d, J=10.8 Hz, 2H), 3.76-3.80 (m, 2H), 3.88 (d, J=6.8 Hz, 2H), 5.08 (d, J=10.4 Hz, 2H), 5.32-5.37 (m, 1H), 7.07-7.09 (m, 2H), 7.34 (s, 1H), 8.20 (s, 1H).

Example 69 cis-isobutyl 4-((6-(2-methoxy-4-((2-oxido-1,3,2-dioxathian-5-yl)methyl)phenoxy)-5-methylpyrimidin-4-yl)oxy)piperidine-1-carboxylate ¹HNMR: δ 0.95 (d, J=6.8 Hz, 6H), 1.78-1.85 (m, 2H), 1.92-1.98 (m, 3H), 2.19 (s, 3H), 2.48 (d, J=7.6 Hz, 2H), 2.70-2.75 (m, 1H), 3.42-3.48 (m, 2H), 3.71 (s, 3H), 3.75-3.84 (m, 4H), 3.88 (d, J=6.8 Hz, 2H), 4.64 (t, J=11.2 Hz, 2H), 5.32-5.36 (m, 1H), 6.75-6.76 (m, 2H), 7.04 (d, J=8.4 Hz, 1H), 8.18 (s, 1H).

Example 70 trans-isobutyl 4-((6-(2-methoxy-4-((2-oxido-1,3,2-dioxathian-5-yl)methyl)phenoxy)-5-methylpyrimidin-4-yl)oxy)piperidine-1-carboxylate ¹HNMR: δ 0.95 (d, J=6.8 Hz, 6H), 1.78-1.85 (m, 3H), 1.92-1.98 (m, 3H), 2.19 (s, 3H), 3.14 (d, J=8.0 Hz, 2H), 3.42-3.48 (m, 2H), 3.69-3.72 (m, 4H), 3.72 (s, 3H), 3.88 (d, J=6.8 Hz, 2H), 5.07 (dd, J=11.6 & 2.4 Hz, 2H), 5.31-5.35 (m, 1H), 6.84-6.86 (m, 2H), 7.05 (d, J=8.4 Hz, 1H), 8.19 (s, 1H).

Example 71 cis-tert-butyl 4-((6-(2-methoxy-4-((2-oxido-1,3,2-dioxathian-5-yl)methyl)phenoxy)-5-methylpyrimidin-4-yl)oxy)piperidine-1-carboxylate ¹HNMR: δ 1.48 (s, 9H), 1.76-1.79 (m, 2H), 1.96-2.01 (m, 2H), 2.18 (s, 3H), 2.49 (d, J=8 Hz, 2H), 2.69-2.75 (m, 1H), 3.34-3.40 (m, 2H), 3.71-3.74 (m, 2H), 3.75 (s, 3H), 3.83 (dd, J=11.6 & 4.4 Hz, 2H), 4.63 (t, J=11.6 Hz, 2H), 5.29-5.33 (m, 1H), 6.75 (t, J=5.6 Hz, 2H), 7.03-7.05 (m, 1H), 8.18 (s, 1H).

Example 72 trans-tert-butyl 4-((6-(2-methoxy-4-((2-oxido-1,3,2-dioxathian-5-yl)methyl)phenoxy)-5-methylpyrimidin-4-yl)oxy)piperidine-1-carboxylate ¹HNMR: δ 1.48 (s, 9H), 1.77-1.79 (m, 2H), 1.93-1.95 (m, 3H), 2.19 (s, 3H), 3.14 (d, J=8 Hz, 2H), 3.34-3.41 (m, 2H), 3.71-3.74 (m, 4H), 3.76 (s, 3H), 5.07 (d, J=12.0 Hz, 2H), 5.29-5.33 (m, 1H), 6.84 (d, J=6.8 Hz, 2H), 7.05 (d, J=8.4 Hz, 1H), 8.19 (s, 1H).

Example 73 cis-5-(4-((6-((1-(3-isopropyl-1,2,4-oxadiazol-5-yl)piperidin-4-yl)oxy)-5-methylpyrimidin-4-yl)oxy)-3-methoxybenzyl)-1,3,2-dioxathiane 2-oxide ¹HNMR: δ 1.30 (d, J=6.0 Hz, 6H), 1.92-1.97 (m, 2H), 2.04-2.12 (m, 2H), 2.19 (s, 3H), 2.49 (d, J=7.6 Hz, 2H), 2.69-2.75 (m, 1H), 2.87-2.94 (m, 1H), 3.61-3.68 (m, 2H), 3.76 (s, 3H), 3.80-3.88 (m, 4H), 4.63 (t, J=11.6 Hz, 2H), 5.38-5.42 (m, 1H), 6.75-6.76 (m, 2H), 7.04 (dd, J=8.4 & 3.2 Hz, 1H), 8.19 (s, 1H).

Example 74 trans-5-(4-((6-((1-(3-isopropyl-1,2,4-oxadiazol-5-yl)piperidin-4-yl)oxy)-5-methylpyrimidin-4-yl)oxy)-3-methoxybenzyl)-1,3,2-dioxathiane 2-oxide ¹HNMR: δ 1.26 (d, J=6.0 Hz, 6H), 1.91-1.98 (m, 3H), 2.04-2.12 (m, 2H), 2.20 (s, 3H), 2.87-2.94 (m, 1H), 3.14 (d, J=8.4 Hz, 2H), 3.62-3.66 (m, 2H), 3.67-3.72 (m, 2H), 3.76 (s, 3H), 3.82-3.88 (m, 2H), 5.05-5.54 (m, 2H), 5.38-5.42 (m, 1H), 6.83-6.85 (m, 2H), 7.06 (d, J=8.4 Hz, 1H), 8.19 (s, 1H).

Example 75 cis-tert-butyl 4-((5-methyl-6-((6-((2-oxido-1,3,2-dioxathian-5-yl)methyl)pyridin-3-yl)oxy)pyrimidin-4-yl)oxy)piperidine-1-carboxylate ¹HNMR: δ 1.48 (s, 9H), 1.74-1.80 (m, 2H), 1.95-2.00 (m, 2H), 2.18 (s, 3H), 2.65 (d, J=7.2 Hz, 2H), 2.99-3.04 (m, 1H), 3.34-3.40 (m, 2H), 3.70-3.87 (m, 2H), 3.89 (dd, J=11.6 & 4.4 Hz, 2H), 4.68 (t, J=11.6, Hz, 2H), 5.31-5.35 (m, 1H), 7.16 (d, J=8.4 Hz, 1H), 7.44 (dd, J=8.4 & 2.8 Hz, 1H), 8.21 (s, 1H), 8.40 (s, 1H).

Example 76 trans-tert-butyl 4-((5-methyl-6-(((6-((2-oxido-1,3,2-dioxathian-5-yl)methyl)pyridin-3-yl)oxy)pyrimidin-4-yl)oxy)piperidine-1-carboxylate $^1$HNMR: δ 1.48 (s, 9H), 1.74-1.80 (m, 2H), 1.97-2.00 (m, 2H), 2.18 (s, 3H), 2.36 (t, J=7.2 Hz, 1H), 3.32 (d, J=8.0 Hz, 2H), 3.35-3.40 (m, 2H), 3.70-3.83 (m, 4H), 5.11 (dd, J=11.6 & 4.4 Hz, 2H), 5.31-5.35 (m, 1H), 7.30 (d, J=8.4 Hz, 1H), 7.46 (dd, J=8.4 & 2.8 Hz, 1H), 8.21 (s, 1H), 8.40 (s, 1H).

Example 77 cis-tert-butyl 4-((6-(4-(2-oxido-1,3,2-dioxathian-5-yl)phenoxy)pyrimidin-4-yl)oxy)piperidine-1-carboxylate $^1$HNMR: δ 1.47 (s, 9H), 1.69-1.75 (m, 2H), 1.97-1.99 (m, 2H), 3.23-3.30 (m, 2H), 3.59-3.65 (m, 1H), 3.76-3.79 (m, 2H), 3.93 (dd, J=11.6 & 4.4 Hz, 2H), 4.97 (t, J=12 Hz, 2H), 5.26-5.30 (m, 1H), 6.15 (s, 1H), 7.13-7.16 (m, 2H), 7.28-7.31 (m, 2H), 8.41 (s, 1H).

Example 78 trans-tert-butyl 4-((6-(4-(2-oxido-1,3,2-dioxathian-5-yl)phenoxy)pyrimidin-4-yl)oxy)piperidine-1-carboxylate $^1$HNMR: δ 1.47 (s, 9H), 1.68-1.76 (m, 2H), 1.97-1.99 (m, 2H), 3.08 (t, J=6.0 Hz, 1H), 3.23-3.30 (m, 2H), 3.76-3.79 (m, 2H), 4.08 (dd, J=12.0 & 2.8 Hz, 2H), 5.23 (dd, J=12 & 4.0 Hz, 2H), 5.26-5.30 (m, 1H), 6.14 (s, 1H), 7.15-7.17 (m, 2H), 7.55 (d, J=8.8 Hz, 2H), 8.43 (s, 1H).

Example 79 cis-tert-butyl 4-(4-((4-(2-oxido-1,3,2-dioxathian-5-yl)phenoxy)methyl)phenoxy)piperidine-1-carboxylate $^1$HNMR: δ 1.46 (s, 9H), 1.72-1.79 (m, 2H), 1.88-1.94 (m, 2H), 3.30-3.36 (m, 2H), 3.49-3.55 (m, 1H), 3.67-3.71 (m, 2H), 3.86-3.90 (m, 2H), 4.45-4.49 (m, 1H), 4.96 (t, J=10.8 Hz, 2H), 4.96 (s, 2H), 6.90-6.97 (m, 4H), 7.13-7.16 (m, 2H), 7.33 (d, J=8.8 Hz, 2H).

Example 80

Iso-butyl 4-((6-(4-(2,2-dioxido-1,3,2-dioxathian-5-yl)phenoxy)-5-methylpyrimidin-4-yl)oxy)piperidine-1-carboxylate To a solution of iso-butyl 4-((5-methyl-6-(4-(2-oxido-1,3,2-dioxathian-5-yl)phenoxy)pyrimidin-4-yl)oxy)piperidine-1-carboxylate (100 mg, 0.000198 mole) in acetonitrile (1.2 mL) were added NaIO$_4$ (59 mg, 0.000277 mole) and RuCl$_3$.3H$_2$O (0.5 mg, 0.0000198 mole) in 0.2 mL water. After stirring the suspension at 30° C. for 30 minutes, 0.8 mL water and 1.2 mL diethyl ether were added. The layers were separated, and the aqueous layer was extracted with diethyl ether. The combined ether layer was dried over sodium sulfate, the solvents were evaporated to yield 50 mg product as white solid.

$^1$HNMR: δ 0.95 (d, J=6.8 Hz, 6H), 1.78-1.82 (m, 2H), 1.92-2.02 (m, 3H), 2.16 (s, 3H), 3.41-3.48 (m, 2H), 3.60-3.65 (m, 1H), 3.74-3.80 (m, 2H), 3.88 (d, J=6.4 Hz, 2H), 4.68 (dd, J=12.0 & 4.0 Hz, 2H), 4.91 (t, J=11.6 Hz, 2H), 5.33-5.36 (m, 1H), 7.17 (dd, J=6.8 & 2.0 Hz, 2H), 7.31 (dd, J=6.8 & 2.0 Hz, 2H), 8.23 (s, 1H).

The following compounds were prepared by procedure similar to that described in example 80 with appropriate variations in reactants, reaction conditions and quantities of reagents.

Example 81

5-(4-((6-((1-(3-isopropyl-1,2,4-oxadiazol-5-yl)piperidin-4-yl)oxy)-5-methylpyrimidin-4-yl)oxy)phenyl)-1,3,2-dioxathiane 2,2-dioxide $^1$HNMR: δ 1.29 (d, J=6.8 Hz, 6H), 1.93-1.98 (m, 2H), 2.04-2.14 (m, 2H), 2.18 (s, 3H) 2.87-2.94 (m, 1H), 3.60-3.67 (m, 3H), 3.82-3.88 (m, 2H), 4.67-4.70 (m, 2H), 4.88-4.94 (m, 2H), 5.40-5.44 (m, 1H), 7.17 (dd, J=6.8 & 2.0 Hz, 2H), 7.32 (dd, J=8.4 & 2.0 Hz, 2H), 8.24 (s, 1H).

Example 82 isobutyl 4-((6-(4-((2,2-dioxido-1,3,2-dioxathian-5-yl)methyl)phenoxy)-5-methylpyrimidin-4-yl)oxy)piperidine-1-carboxylate $^1$HNMR: δ 0.95 (d, J=6.8 Hz, 6H), 1.75-1.84 (m, 2H), 1.92-2.02 (m, 3H), 2.17 (s, 3H), 2.38-2.41 (m, 1H), 2.83 (d, J=8.0 Hz, 2H), 3.42-3.48 (m, 2H), 3.74-3.80 (m, 2H), 3.88 (d, J=6.4 Hz, 2H), 4.50 (dd, J=11.6 & 6.8 Hz, 2H), 4.71 (dd, J=11.6 & 3.6 Hz, 2H), 5.33-5.36 (m, 1H), 7.10 (d, J=8.4 Hz, 2H), 7.21 (d, J=8.4 Hz, 2H), 8.23 (s, 1H).

Example 83

5-(4-((6-((1-(5-ethylpyrimidin-2-yl)piperidin-4-yl)oxy)-5-methylpyrimidin-4-yl)oxy)benzyl)-1,3,2-dioxathiane 2,2-dioxide $^1$HNMR: δ 1.20 (t, J=7.6 Hz, 3H), 1.80-1.88 (m, 2H), 2.04-2.11 (m, 2H), 2.17 (s, 3H), 2.37-2.43 (m, 1H), 2.47 (q, J=7.6 Hz, 2H), 2.83 (d, J=8.0 Hz, 2H), 3.68-3.73 (m, 2H), 4.16-4.18 (m, 2H), 4.51 (dd, J=11.6 & 6.8 Hz, 2H), 4.71 (dd, J=11.6 & 3.6 Hz, 2H), 5.40-5.44 (m, 1H), 7.10-7.12 (m, 2H), 7.21 (d, J=8.4 Hz, 2H), 8.19 (s, 2H), 8.25 (s, 1H).

Example 84

5-(4-((6-(4-(3-isopropyl-1,2,4-oxadiazol-5-yl)piperidin-1-yl)-5-nitropyrimidin-4-yl)oxy)phenyl)-1,3,2-dioxathiane 2,2-dioxide $^1$HNMR: δ 1.33 (d, J=6.8 Hz, 6H), 1.97-2.07 (m, 2H), 2.19-2.23 (m, 2H), 3.04-3.11 (m, 1H), 3.24-3.35 (m, 3H), 3.60-3.65 (m, 1H), 4.08-4.13 (m, 2H), 4.67-4.71 (dd, J=12 & 4.8 Hz, 2H), 4.87-4.93 (m, 2H), 7.18-7.21 (m, 2H), 7.32-7.35 (m, 2H), 8.19 (s, 1H).

Example 85

5-(4-((6-((1-(5-ethylpyrimidin-2-yl)piperidin-4-yl)oxy)-5-methylpyrimidin-4-yl)oxy)phenyl)-1,3,2-dioxathiane 2,2-dioxide ¹HNMR: δ 1.20 (t, J=7.6 Hz, 3H), 1.80-1.88 (m, 2H), 2.04-2.11 (m, 2H), 2.17 (s, 3H), 2.45-2.50 (q, J=8.0 Hz, 2H), 3.60-3.73 (m, 3H), 4.15-4.21 (m, 2H), 4.66-4.70 (m, 2H), 4.88-4.94 (m, 2H), 5.40-5.44 (m, 1H), 7.17 (dd, J=6.8 & 2.0 Hz, 2H), 7.31 (dd, J=8.8 & 2.0 Hz, 2H), 8.19 (s, 2H), 8.25 (s, 1H).

Example 86

5-(4-((6-(4-(3-isopropyl-1,2,4-oxadiazol-5-yl)piperidin-1-yl)-5-methylpyrimidin-4-yl)oxy)phenyl)-1,3,2-dioxathiane 2,2-dioxide ¹HNMR: δ 1.34 (d, J=7.2 Hz, 6H), 2.01-2.20 (m, 3H), 2.20-2.24 (m, 5H), 3.05-3.20 (m, 4H), 3.60-3.65 (m, 1H), 3.88 (d, J=13.6 Hz, 2H), 4.65-4.70 (m, 2H), 4.88-4.93 (m, 2H), 7.13-7.17 (m, 2H), 7.30-7.33 (m, 2H), 8.28 (s, 1H).

Example 87 tert-butyl 4-((6-(4-(2,2-dioxido-1,3,2-dioxathian-5-yl)phenoxy)-5-methylpyrimidin-4-yl)oxy)piperidine-1-carboxylate ¹HNMR: δ 1.48 (s, 9H), 1.75-1.81 (m, 2H), 1.96-2.00 (m, 2H), 2.16 (s, 3H), 3.34-3.65 (m, 2H), 3.60-3.65 (m, 1H), 3.69-3.78 (m, 2H), 4.66-4.70 (m, 2H), 4.88-4.93 (m, 2H), 5.31-5.35 (m, 1H), 7.17 (dd, J=9.2 & 2.8 Hz, 2H), 7.30-7.32 (m, 2H), 8.23 (s, 1H).

Example 88 tert-butyl 4-(2-(4-(2,2-dioxido-1,3,2-dioxathian-5-yl)phenoxy)ethoxy)piperidine-1-carboxylate ¹HNMR (DMSO-d6): δ 1.27-1.34 (m, 2H), 1.37 (s, 9H), 1.76-1.79 (m, 2H), 2.98-2.00 (m, 2H), 3.49-3.53 (m, 1H), 3.58-3.69 (m, 3H), 3.72 (t, J=4.8 Hz, 2H), 4.06 (t, J=4.4 Hz, 2H), 4.86 (d, J=7.2 Hz, 4H), 6.94 (d, J=8.8 Hz, 2H), 7.30 (d, J=8.8 Hz, 2H).

Example 89 tert-butyl 4-(3-((6-(4-(2,2-dioxido-1,3,2-dioxathian-5-yl)phenoxy)-5-methylpyrimidin-4-yl)oxy)propyl)piperidine-1-carboxylate ¹HNMR: δ 1.10-1.17 (m, 2H), 1.37-1.43 (m, 3H), 1.45 (s, 9H), 1.68 (d, J=12.0 Hz, 2H), 1.79-1.86 (m, 2H), 2.16 (s, 3H), 2.68 (t, J=10.8 Hz, 2H), 3.60-3.65 (m, 1H), 4.09-4.13 (m, 2H), 4.37 (t, J=6.8 Hz, 2H), 4.68 (dd, J=12.0 & 4.8 Hz, 2H), 4.90 (t, J=11.6 Hz, 2H), 7.16 (d, J=8.4 Hz, 2H), 7.31 (d, J=8.4 Hz, 2H), 8.24 (s, 1H).

Example 90 tert-butyl 4-((6-(4-((2,2-dioxido-1,3,2-dioxathian-5-yl)methyl)phenoxy)-5-methylpyrimidin-4-yl)oxy)piperidine-1-carboxylate ¹HNMR: δ 1.48 (s, 9H), 1.75-1.95 (m, 2H), 1.95-2.00 (m, 2H), 2.17 (s, 3H), 2.39-2.41 (m, 1H), 2.83 (d, J=8.0 Hz, 2H), 3.34-3.41 (m, 2H), 3.69-3.75 (m, 2H), 4.50 (dd, J=11.6 & 6.4 Hz, 2H), 4.70 (dd, J=11.6 & 3.6 Hz, 2H), 5.31-5.34 (m, 1H), 7.09-7.12 (m, 2H), 7.21 (d, J=8.8 Hz, 2H), 8.23 (s, 1H).

Example 91 ethyl 4-((6-(4-(2,2-dioxido-1,3,2-dioxathian-5-yl)phenoxy)-5-methylpyrimidin-4-yl)oxy)piperidine-1-carboxylate ¹HNMR: δ 1.28 (t, J=7.2 Hz, 3H), 1.77-1.83 (m, 2H), 1.97-2.02 (m, 2H), 2.16 (s, 3H), 3.41-3.47 (m, 2H), 3.60-3.65 (m, 1H), 3.74-3.78 (m, 2H), 4.15 (q, J=14.4 Hz, 2H), 4.68 (dd, J=11.6 & 4.8 Hz, 2H), 4.88-4.93 (m, 2H), 5.3-5.36 (m, 1H), 7.17 (dd, J=6.8 & 2.0 Hz, 2H), 7.31 (d, J=8.4 Hz, 2H), 8.23 (s, 1H).

Example 92 benzyl 4-((6-(4-(2,2-dioxido-1,3,2-dioxathian-5-yl)phenoxy)-5-methylpyrimidin-4-yl)oxy)piperidine-1-carboxylate ¹HNMR: δ 1.81-1.83 (m, 2H), 1.99-2.04 (m, 2H), 2.16 (s, 3H), 3.45-3.51 (m, 2H), 3.61-3.63 (m, 1H), 3.76-3.81 (m, 2H), 4.66-4.70 (m, 2H), 4.91 (t, J=10.8 Hz, 2H), 5.15 (s, 2H), 5.34-5.35 (m, 1H), 7.16 (dd, J=6.8 & 2.0 Hz, 2H), 7.30-7.34 (m, 3H), 7.38 (d, J=4.4 Hz, 4H), 8.23 (s, 1H).

Example 93

Ethyl 4-((6-(4-((2,2-dioxido-1,3,2-dioxathian-5-yl)methyl)phenoxy)-5-methylpyrimidin-4-yl)oxy)piperidine-1-carboxylate ¹HNMR: δ 1.28 (t, J=7.2 Hz, 3H), 1.75-1.84 (m, 2H), 1.97-2.02 (m, 2H), 2.17 (s, 3H), 2.37-2.42 (m, 1H), 2.83 (d, J=8.0 Hz, 2H), 3.41-3.47 (m, 2H), 3.74-3.78 (m, 2H), 4.13-4.18 (q, J=7.0 Hz, 2H), 4.49-4.53 (dd, J=11.4 & 6.6 Hz, 2H), 4.69-4.72 (dd, J=11.6 & 3.6 Hz, 2H), 5.32-5.37 (m, 1H), 7.09-7.11 (dd, J=6.8 & 2 Hz, 2H), 7.21 (d, J=8.4 Hz, 2H), 8.23 (s, 1H).

Example 94

5-(4-((5-methyl-6-((1-(pyrimidin-2-yl)piperidin-4-yl)oxy)pyrimidin-4-yl)oxy)benzyl)-1,3,2-dioxathiane 2,2-dioxide ¹HNMR: δ 1.83-1.88 (m, 2H), 2.05-2.10 (m, 2H), 2.17 (s, 3H), 2.38-2.42 (m, 1H), 2.83 (d, J=8.0 Hz, 2H), 3.72-3.78 (m, 2H), 4.17-4.22 (m, 2H), 4.51 (dd, J=11.6 & 6.8 Hz, 2H), 4.71 (dd, J=11.6 & 3.6 Hz, 2H), 5.42-5.44 (m, 1H), 6.49 (t, J=4.8 Hz, 1H), 7.10-7.11 (m, 2H), 7.21 (d, J=8.4 Hz, 2H), 8.25 (s, 1H), 8.32 (d, J=4.8 Hz, 2H).

Example 95

Isopropyl 4-((6-(4-(2,2-dioxido-1,3,2-dioxathian-5-yl)phenoxy)-5-methylpyrimidin-4-yl)oxy)piperidine-1-carboxylate ¹HNMR: δ 1.26 (d, J=6.0 Hz, 6H), 1.77-1.80 (m, 2H), 1.97-2.01 (m, 2H), 2.16 (s, 3H), 3.39-3.45 (m, 2H), 3.58-3.65 (m, 1H), 3.74-3.76 (m, 2H), 4.68 (dd, J=11.6 & 4.8 Hz, 2H), 4.88-4.97 (m, 3H), 5.32-5.36 (m, 1H), 7.16 (d, J=8.8 Hz, 2H), 7.31 (d, J=8.8 Hz, 2H), 8.23 (s, 1H).

Example 96

Isopropyl 4-((6-(4-((2,2-dioxido-1,3,2-dioxathian-5-yl)methyl)phenoxy)-5-methylpyrimidin-4-yl)oxy)piperidine-1-carboxylate $^1$HNMR: δ 1.26 (d, J=6.4 Hz, 6H), 1.77-1.81 (m, 2H), 1.97-2.00 (m, 2H), 2.17 (s, 3H), 2.38-2.41 (m, 1H), 2.83 (d, J=8.0 Hz, 2H), 3.39-3.45 (m, 2H), 3.74-3.77 (m, 2H), 4.50 (dd, J=11.2 & 6.4 Hz, 2H), 7.71 (dd, J=11.6 & 3.6 Hz, 2H), 4.91-4.97 (m, 1H), 5.32-5.36 (m, 1H), 7.11 (d, J=8.4 Hz, 2H), 7.21 (d, J=8.4 Hz, 2H), 8.23 (s, 1H).

Example 97 tert-butyl 4-(4-((2,2-dioxido-1,3,2-dioxathian-5-yl)methyl)phenoxy)piperidine-1-carboxylate $^1$HNMR: δ 1.46 (s, 9H), 1.71-1.76 (m, 2H), 1.88-1.93 (m, 2H), 2.35-2.37 (m, 1H), 2.74 (d, J=8.0 Hz, 2H), 3.30-3.36 (m, 2H), 3.66-3.72 (m, 2H), 4.42-4.50 (m, 3H), 4.63-4.67 (dd, J=11.6 & 3.6 Hz, 2H), 6.87 (d, J=8.4 Hz, 2H), 7.07 (d, J=8.4 Hz, 2H).

Example 98

5-(4-((1-(5-ethylpyrimidin-2-yl)piperidin-4-yl)oxy)benzyl)-1,3,2-dioxathiane 2,2-dioxide $^1$HNMR: δ 1.19 (t, J=7.6 Hz, 3H), 1.78-1.52 (m, 2H), 1.99-2.04 (m, 2H), 2.36 (m, 1H), 2.46 (q, J=7.6 Hz, 2H), 2.74 (d, J=8.0 Hz, 2H), 3.60-3.66 (m, 2H), 4.14-4.20 (m, 2H), 4.46-4.54 (m, 3H), 4.66 (dd, J=11.6 & 4.0 Hz, 2H), 6.90 (dd, J=6.8 & 2.0 Hz, 2H), 7.08 (d, J=8.4 Hz, 2H), 8.18 (s, 2H).

Example 99

5-(3-chloro-4-((6-((1-(3-isopropyl-1,2,4-oxadiazol-5-yl)piperidin-4-yl)oxy)-5-methylpyrimidin-4-yl)oxy)benzyl)-1,3,2-dioxathiane 2,2-dioxide $^1$HNMR: δ 1.29 (d, J=6.8 Hz, 6H), 1.91-1.99 (m, 2H), 2.07-2.13 (m, 2H), 2.21 (s, 3H), 2.36-2.40 (m, 1H), 2.83-2.94 (m, 3H), 3.61-3.67 (m, 2H), 3.83-3.89 (m, 2H), 4.50 (dd, J=11.6 & 6.0 Hz, 2H), 4.74 (dd, J=11.6 & 3.6 Hz, 2H), 5.40-5.44 (m, 1H), 7.10-7.23 (m, 2H), 7.30 (d, J=2.0 Hz, 1H), 8.20 (s, 1H).

Example 100

Isobutyl 4-((6-(2-chloro-4-(2,2-dioxido-1,3,2-dioxathian-5-yl)phenoxy)-5-methylpyrimidin-4-yl)oxy)piperidine-1-carboxylate $^1$HNMR: δ 0.96 (d, J=6.8 Hz, 6H), 1.80-1.86 (m, 2H), 1.93-2.05 (m, 3H), 2.21 (s, 3H), 3.42-3.49 (m, 2H), 3.56-3.64 (m, 1H), 3.76-3.82 (m, 2H), 3.90 (d, J=6.8 Hz, 2H), 4.73 (dd, J=12.0 & 4.8 Hz, 2H), 4.87-4.95 (m, 2H), 5.33-5.39 (m, 1H), 7.18 (dd, J=6.4 & 2.0 Hz, 1H), 7.33 (d, J=8.8 Hz, 1H), 7.41 (s, 1H), 8.20 (s, 1H).

Example 101

Isobutyl 4-((6-(2-chloro-4-((2,2-dioxido-1,3,2-dioxathian-5-yl)methyl)phenoxy)-5-methylpyrimidin-4-yl)oxy)piperidine-1-carboxylate $^1$HNMR: δ 0.95 (d, J=6.4 Hz, 6H), 1.78-1.83 (m, 2H), 1.92-2.03 (m, 3H), 2.20 (s, 3H), 2.37-2.38 (m, 1H), 2.85 (d, J=8.0 Hz, 2H), 3.41-3.48 (m, 2H), 3.75-3.88 (m, 2H), 3.88 (d, J=6.8 Hz, 2H), 4.49 (dd, J=11.6 & 6.0 Hz, 2H), 4.74 (dd, J=12.0 & 3.6 Hz, 2H), 5.33-5.36 (m, 1H), 7.14 (dd, J=8.76 & 2.0 Hz, 1H), 7.20 (d, J=8.4 Hz, 1H), 7.30 (d, J=2.0 Hz, 1H), 8.19 (s, 1H).

Example 102

Isobutyl 4-((6-(4-((2,2-dioxido-1,3,2-dioxathian-5-yl)methyl)-2-methoxyphenoxy)-5-methylpyrimidin-4-yl)oxy)piperidine-1-carboxylate $^1$HNMR: δ 0.95 (d, J=6.8 Hz, 6H), 1.78-1.83 (m, 2H), 1.93-2.05 (m, 3H), 2.19 (s, 3H), 2.39-2.42 (m, 1H), 2.83 (d, J=8.0 Hz, 2H), 3.42-3.48 (m, 2H), 3.74-3.80 (m, 5H), 3.88 (d, J=8.0 Hz, 2H), 4.52 (dd, J=11.6 & 6.4 Hz, 2H), 4.73 (dd, J=11.6 & 3.6 Hz, 2H), 5.32-5.34 (m, 1H), 6.79-6.81 (m, 2H), 7.07 (dd, J=8.4 & 3.6 Hz, 1H), 8.18 (s, 1H).

Example 103 tert-butyl 4-((6-(4-((2,2-dioxido-1,3,2-dioxathian-5-yl)methyl)-2-methoxyphenoxy)-5-methylpyrimidin-4-yl)oxy)piperidine-1-carboxylate $^1$HNMR: δ 1.48 (s, 9H), 1.75-1.81 (m, 2H), 1.95-2.00 (m, 2H), 2.18 (s, 3H), 2.40-2.43 (m, 1H), 2.83 (d, J=8.0 Hz, 2H), 3.34-3.40 (m, 2H), 3.70-3.74 (m, 2H), 3.76 (s, 3H), 4.52 (dd, J=11.6 & 6.4 Hz, 2H), 4.72 (dd, J=11.6 & 3.6 Hz, 2H), 5.29-5.33 (m, 1H), 6.78-6.80 (m, 2H), 7.073 (d, J=8.4 Hz, 1H), 8.17 (s, 1H).

Example 104

5-(4-((6-((1-(3-isopropyl-1,2,4-oxadiazol-5-yl)piperidin-4-yl)oxy)-5-methylpyrimidin-4-yl)oxy)-3-methoxybenzyl)-1,3,2-dioxathiane 2,2-dioxide $^1$HNMR: δ 1.30 (d, J=6.8 Hz, 6H), 1.91-1.98 (m, 2H), 2.07-2.13 (m, 2H), 2.19 (s, 3H), 2.39-2.41 (m, 1H), 2.84 (d, J=8.0 Hz, 2H), 2.87-2.94 (m, 1H), 3.61-3.68 (m, 2H), 3.76 (s, 3H), 3.82-3.88 (m, 2H), 4.52 (dd, J=11.6 & 6.4 Hz, 2H), 4.73 (dd, J=11.6 & 3.6 Hz, 2H), 5.39-5.42 (m, 1H), 6.80 (dd, J=5.2 & 2.0 Hz, 2H), 7.07 (dd, J=5.2 & 2.0 Hz, 1H), 8.19 (s, 1H).

Example 105 tert-butyl 4-((6-(4-(2,2-dioxido-1,3,2-dioxathian-5-yl)phenoxy)pyrimidin-4-yl)oxy)piperidine-1-carboxylate $^1$HNMR: δ 1.48 (s, 9H), 1.70-1.75 (m, 2H), 1.96-2.00 (m, 2H), 3.24-3.30 (m, 2H), 3.60-3.65 (m, 1H), 3.76-3.79 (m, 2H), 4.67-4.72 (m, 2H), 4.88-4.93 (m, 2H), 5.27-5.31 (m, 1H), 6.18 (s, 1H), 7.18 (d, J=8.4 Hz, 2H), 7.32-7.35 (d, J=8.4 Hz, 2H), 8.40 (s, 1H).

Example 106 tert-butyl 4-(4-((4-(2,2-dioxido-1,3,2-dioxathian-5-yl)phenoxy)methyl)phenoxy)piperidine-1-carboxylate ¹HNMR: δ 1.47 (s, 9H), 1.72-1.77 (m, 2H), 1.89-1.93 (m, 2H), 3.30-3.37 (m, 2H), 3.55-3.57 (m, 1H), 3.66-3.72 (m, 2H), 4.68-4.48 (m, 1H), 4.61 (dd, J=11.6 & 4.8 Hz, 2H), 4.86 (t, J=11.6 Hz, 2H), 4.97 (s, 2H), 6.92 (d, J=8.4 Hz, 2H), 6.97 (d, J=8.8 Hz, 2H), 7.17 (d, J=8.4 Hz, 2H), 7.33 (d, J=8.8 Hz, 2H).

Example 107 tert-butyl 4-(4-((2,2-dioxido-1,3,2-dioxathian-5-yl)methyl)-2-methoxyphenoxy)piperidine-1-carboxylate ¹HNMR: δ 1.46 (s, 9H), 1.73-1.79 (m, 2H), 1.88-1.93 (m, 2H), 2.36-2.38 (m, 1H), 2.75 (d, J=8.0 Hz, 2H), 3.21-3.27 (m, 2H), 3.77-3.80 (m, 2H), 3.84 (s, 3H), 4.35-4.37 (m, 1H), 4.48 (dd, J=11.2 & 6.4 Hz, 2H), 4.67 (dd, J=11.2 & 3.6 Hz, 2H), 6.67 (d, J=7.2 Hz, 2H), 6.88 (d, J=8.0 Hz, 1H).

Example 108 tert-butyl 4-(4-((4-(2,2-dioxido-1,3,2-dioxathian-5-yl)phenoxy)methyl)thiazol-2-yl)piperidine-1-carboxylate ¹HNMR: δ 1.47 (s, 9H), 1.71-1.78 (m, 2H), 2.08-2.12 (d, J=12.8 Hz, 2H), 2.87 (t, J=12.8 Hz, 2H), 3.13-3.18 (m, 1H), 3.53-3.59 (m, 1H), 4.20-4.21 (m, 2H), 4.60-4.64 (m, 2H), 4.84-4.89 (m, 2H), 5.15 (s, 2H), 7.01 (dd, J=6.8 & 2.0 Hz, 2H), 7.16-7.20 (m, 3H),

Example 109 tert-butyl 4-((6-(4-((2,2-dioxido-1,3,2-dioxathiolan-4-yl)methyl)phenoxy)-5-methylpyrimidin-4-yl)oxy)piperidine-1-carboxylate ¹HNMR: δ 1.48 (s, 9H), 1.73-1.81 (m, 2H), 1.96-2.00 (m, 2H), 2.16 (s, 3H), 3.07 (dd, J=14.4 & 6.4 Hz, 1H), 3.31-3.41 (m, 3H), 3.71-3.74 (m, 2H), 4.46 (t, J=8.2 Hz, 1H), 4.66-4.70 (q, J=6.0 Hz, 1H), 5.12-5.17 (m, 1H), 5.31-5.34 (m, 1H), 7.12 (d, J=8.4 Hz, 2H), 7.26 (d, J=6.8 Hz, 2H), 8.23 (s, 1H).

Example 110

5-(4-(3-(1-(pyrimidin-2-yl)piperidin-4-yl)propoxy)phenyl)-1,3,2-dioxathiane 2,2-dioxide ¹HNMR: δ 1.14-1.30 (m, 2H), 1.40-1.45 (m, 3H), 1.78-1.86 (m, 4H), 2.82-2.89 (m, 2H), 3.53-3.58 (m, 1H), 3.94 (t, J=6.4 Hz, 2H), 4.60 (dd, J=12.0 & 4.8 Hz, 2H), 4.80 (d, J=13.2 Hz, 2H), 4.86 (t, J=11.6 Hz, 2H), 6.34 (t, J=4.8 Hz, 1H), 6.89 (d, J=8.8 Hz, 2H), 7.16 (d, J=8.8 Hz, 2H), 8.28 (d, J=4.8 Hz, 2H).

The following compounds are prepared by following the processes described above with suitable modifications as may be necessary.

Example 111 cis-tert-butyl 4-(4-((4-((2-oxido-1,3,2-dioxathian-5-yl)methyl)phenoxy)methyl)phenoxy)piperidine-1-carboxylate

Example 112

5-(4-((5-methyl-6-((1-(pyrimidin-2-yl)piperidin-4-yl)oxy)pyrimidin-4-yl)oxy)phenyl)-1,3,2-dioxathiane 2,2-dioxide

Example 113

5-(4-(2-((1-(5-ethylpyrimidin-2-yl)piperidin-4-yl)oxy)ethoxy)phenyl)-1,3,2-dioxathiane 2,2-dioxide

Example 114

5-(4-(2-((1-(3-isopropyl-1,2,4-oxadiazol-5-yl)piperidin-4-yl)oxy)ethoxy)phenyl)-1,3,2-dioxathiane 2,2-dioxide

Example 115

5-(4-((2-(1-(pyrimidin-2-yl)piperidin-4-yl)thiazol-4-yl)methoxy)phenyl)-1,3,2-dioxathiane 2,2-dioxide

Example 116

5-(4-((2-(1-(5-ethylpyrimidin-2-yl)piperidin-4-yl)thiazol-4-yl)methoxy)phenyl)-1,3,2-dioxathiane 2,2-dioxide

Example 117

5-(4-(2-((1-(pyrimidin-2-yl)piperidin-4-yl)oxy)ethoxy)phenyl)-1,3,2-dioxathiane 2,2-dioxide

Example 118 tert-butyl 4-((6-(4-(2,2-dioxido-1,3,2-dioxathiolan-4-yl)phenoxy)-5-methylpyrimidin-4-yl)oxy)piperidine-1-carboxylate

Example 119

5-(4-((6-((1-benzylpiperidin-4-yl)oxy)-5-methylpyrimidin-4-yl)oxy)phenyl)-1,3,2-dioxathiane 2,2-dioxide

Example 120

N-(2,4-dichlorophenyl)-4-((6-(4-(2,2-dioxido-1,3,2-dioxathian-5-yl)phenoxy)-5-methylpyrimidin-4-yl)oxy)piperidine-1-carboxamide

Example 121

5-(4-((1-(3-isopropyl-1,2,4-oxadiazol-5-yl)piperidin-4-yl)oxy)benzyl)-1,3,2-dioxathiane 2,2-dioxide

Example 122 tert-butyl 4-(4-((2,2-dioxido-1,3,2-dioxathian-5-yl)methyl)-3-methoxyphenoxy)piperidine-1-carboxylate

Example 123 tert-butyl 4-((6-(2-chloro-4-((2,2-dioxido-1,3,2-dioxathian-5-yl)methyl)phenoxy)-5-methylpyrimidin-4-yl)oxy)piperidine-1-carboxylate

Example 124 tert-butyl 4-((6-((6-((2,2-dioxido-1,3,2-dioxathian-5-yl)methyl)pyridin-3-yl)oxy)-5-methylpyrimidin-4-yl)oxy)piperidine-1-carboxylate

Example 125 tert-butyl 4-(4-((4-((2,2-dioxido-1,3,2-dioxathian-5-yl)methyl)phenoxy)methyl)phenoxy)piperidine-1-carboxylate

Example 126 tert-butyl 4-(4-((4-((2,2-dioxido-1,3,2-dioxathian-5-yl)methyl)phenoxy)methyl)thiazol-2-yl)piperidine-1-carboxylate

Example 127

5-(4-(((6-((1-(3-isopropyl-1,2,4-oxadiazol-5-yl)piperidin-4-yl)oxy)-5-methylpyrimidin-4-yl)oxy)benzyl)-1,3,2-dioxathiane 2,2-dioxide The novel compounds of the present invention can be formulated into suitable pharmaceutically acceptable compositions by combining with suitable excipients by techniques and processes and concentrations as are well known. Thus a pharmaceutical composition comprising the compounds of the present invention may comprise of a suitable binder, suitable bulking agent &/or diluent and any other suitable agents as may be necessary. Optionally, the pharmaceutical composition may be suitably coated with suitable coating agents.

The compounds of formula (I) or pharmaceutical compositions containing them are useful as ligands of the GPR-119 receptor suitable for humans and other warm blooded animals, and may be administered either by oral, topical or parenteral administration.

The quantity of active component, that is, the compounds of formula (I) according to this invention, in the pharmaceutical composition and unit dosage form thereof may be varied or adjusted widely depending upon several factors such as the particular application method, the potency of the particular compound and the desired concentration.

Biological Activity:

The biological activity of the compounds of the present invention were tested in the following in vitro and in vivo models mentioned here.

cAMP assay: A stable cell line expressing recombinant human GPR 119 receptor was established and used to investigate the efficacy of the compounds of the invention based on the intracellular levels of cyclic AMP (cAMP) using commercially available cAMP kits. Compounds of the invention produced a concentration dependent increase in cAMP level and $EC_{50}$ values of representative compounds were provided in table 1.

TABLE 1

| Example | $EC_{50}$ nM |
|---|---|
| 1 | 31 |
| 3 | 13 |
| 4 | 11 |
| 9 | 12 |
| 10 | 73.6 |
| 15 | 4.2 |
| 16 | 15 |
| 27 | 27 |
| 28 | 57 |
| 32 | 86 |
| 33 | 86 |
| 34 | 93 |
| 39 | 94 |
| 44 | 108 |

In Vivo Efficacy Studies:

Feed Intake in Sprague Dawley Rats:

Sprague Dawley rats of 6-8 week age are used for this experiment they are kept for acclimatization in reversed light/dark cycle for 15 days. Animals will have free access to a standard chow diet and water during acclimatization period. After 15 days reversed light/dark cycle acclimatization animals are trained for fasting induced feed intake for 5 days till they show consistent feed intake. Grouping was done based on the monitored feed intake during the training days. On treatment day each group of animals are dosed with test compound or vehicle by appropriate routes of administration (orally or intraperitoneally). Exactly 30 min. after treatment, measured amount of standard chow diet is provided and recorded as O-min feed offered. Then subsequently 2, 4, 6 and 24 hour after O-min, feed intake is measured and the cumulative feed intakes are calculated. The change in cumulative feed intake as compared to vehicle treated control at each time point is calculated for test compound. Results are provided in table 2 and table 3.

TABLE 2 administration (intraperitoneally).

| Example | Dose (mg/kg) | % reduction in food in take | | | |
|---|---|---|---|---|---|
| | | 2 hour | 4 hour | 6 hour | 24 hour |
| 1 | 25 | 45 | 24 | 8.5 | 4 |
| 5 | 25 | 35 | 17 | 21 | 8 |
| 9 | 25 | 44 | 37 | 30 | 24 |
| 4 | 25 | 40 | 33 | 21 | — |
| 3 | 25 | 34 | 25 | 25 | 17 |
| 16 | 25 | 21 | 27 | 10 | — |
| 15 | 25 | 47 | 31 | 28 | 19 |
| 17 | 25 | 34 | 34 | 24 | 13 |
| 28 | 25 | 67 | 59 | 40 | 24 |
| 27 | 25 | 35 | 35 | 31 | 17 |
| 31 | 25 | 28 | 34 | 28 | 9 |
| 32 | 25 | 50 | 37 | 32 | 18 |
| 29 | 25 | 50 | 24 | 5 | 4 |
| 30 | 25 | 39 | 31 | 5 | 9 |
| 33 | 25 | 70 | 44 | 24 | 21 |
| 34 | 25 | 45 | 30 | 19 | 10 |

TABLE 3

| | | administration (oral). | | | |
|---|---|---|---|---|---|
| | Dose | % reduction in food in take | | | |
| Example | (mg/kg) | 2 hour | 4 hour | 6 hour | 24 hour |
| 10 | 50 | 36 | 29 | 15 | 15 |
| 9 | 50 | 25 | 12 | 6 | 2 |
| 4 | 50 | 30 | 24 | 9.5 | 6 |
| 28 | 50 | 24 | 19 | 9 | 2 |
| 27 | 50 | 23 | 20 | 23 | 5 |
| 44 | 50 | 38 | 30 | 24 | 7 |
| 48 | 50 | 32 | 17 | 17 | 10 |
| 45 | 50 | 28 | 28 | 16 | 7 |
| 47 | 50 | 23 | 16 | 3 | 3 |
| 55 | 50 | 33 | 5.3 | — | — |
| 59 | 50 | 23 | 21 | 15 | 11 |
| 60 | 50 | 39 | 31 | 24 | 5.3 |
| 63 | 50 | 44 | 41 | 25 | 15 |

Oral Glucose Tolerance Tests (OGTT) in C57/BL6 Mice:

C57/BL6 mice of 6-8 week age are used for this experiment. Animals are grouped based on non-fasting serum glucose levels and kept on fasting for overnight (day before OGTT). On the experiment day, each animal receive a single dose of vehicle/test compounds (30 mg/kg) administered orally, 30 min post dosing animals are bled for basal glucose level estimation and at the same time glucose load (3 gm/kg) will be administered per orally. Blood is collected at time points corresponding to 20, 40, 60 and 120 min after glucose load administration. Serum is separated for determination of glucose levels and change in area under curve for glucose is calculated and provided in table 4 as % reduction in AUC.

TABLE 4

| Example | % reduction in AUC at 50 mg/kg |
|---|---|
| 1 | 23 |
| 10 | 29 |
| 9 | 31 |
| 4 | 31 |
| 3 | 23 |
| 16 | 34 |
| 18 | 11 |
| 17 | 34 |
| 20 | 25 |
| 28 | 40 |
| 27 | 30 |
| 32 | 41 |
| 33 | 30 |
| 34 | 27 |
| 44 | 31 |
| 63 | 31 |

Thus, the compounds of the present invention are selective to the GPR-119 receptor and shows potential to reduce food intake and thereby has potential to help control/reduce obesity. Additionally, they have potential glucose reducing effects in various degrees. Thus, these compounds may be useful as potential treatments of diabetes and/or obesity.

The novel compounds of the present invention (I) may be formulated into suitable pharmaceutically acceptable compositions by combining with suitable excipients by techniques and processes and concentrations as are well known.

The compounds of formula (I) or pharmaceutical compositions containing them are suitable for humans and other warm blooded animals, and may be administered either by oral, topical or parenteral administration or other suitable routes based on the requirement of the patients for the treatment of various disease conditions associated with dyslipidemia, obesity etc.

The pharmaceutical composition is provided by employing conventional techniques. Preferably the composition is in unit dosage form containing an effective amount of the active component, that is, the compounds of formula (I) according to this invention.

The quantity of active component, that is, the compounds of formula (I) according to this invention, in the pharmaceutical composition and unit dosage form thereof may be varied or adjusted widely depending upon the particular application method, the potency of the particular compound and the desired concentration. Generally, the quantity of active component will range between 0.5% to 90% by weight of the composition.

While the present invention has been described in terms of its specific embodiments, certain modifications and equivalents will be apparent to those skilled in the art and are intended to be included within the scope of the present invention.

We claim:

1. A compound having the structure of Formula (I),

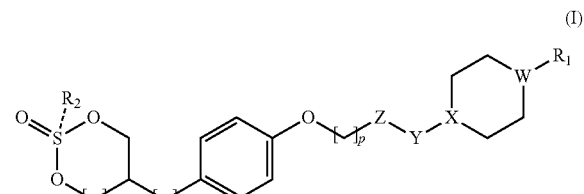

(I)

or its pharmaceutically acceptable salts, pharmaceutically acceptable solvates, enantiomers, stereoisomers, wherein $R_1$ represents optionally substituted groups selected from linear or branched $(C_1-C_6)$alkyl, aralkyl, cycloalkyl, cycloalkylalkyl, heterocyclyl, heterocyclylalkyl, heteroaryl, heteroaralkyl or the groups $C(O)OR_3$, $C(O)R_3$, and $SO_2R_3$, wherein $R_3$ represents H, or optionally substituted groups selected from linear or branched $(C_1-C_6)$ alkyl, aryl, aralkyl, cycloalkyl, cycloalkylalkyl, heterocyclyl, heterocyclylalkyl, heteroaryl, heteroaralkyl groups;

'Z' when present represents an optionally substituted single or fused group selected from aryl, heteroaryl, heterocyclyl, cycloalkyl groups; 'Y' represents either a bond or groups selected from oxygen, —NH, S, SO, $SO_2$ or $NR_4$, wherein $R_4$ represents, linear or branched $(C_1-C_6)$alkyl; 'X' and 'W' may be same or different & independently represents C or N; 'm' 'n' and 'p' independently represents an integer ranging from 0 to 4; and $R_2$ may be optionally present and when present represents an oxo group.

2. The compound according to claim 1, wherein 'Z' is absent and all other symbols are as defined in claim 1.

3. The compound according to claim 1, wherein 'Z' represents optionally substituted single or fused group selected from aryl, heteroaryl, heterocyclyl, cycloalkyl groups and all other symbols are as defined in claim 1.

4. The compound according to claim 1, wherein 'Y' represents a bond and all other symbols are as defined in claim 1.

5. The compound according to claim 1, wherein 'Y' is selected from oxygen, —NH, S, SO, $SO_2$ or $NR_4$, wherein $R_4$ represents, linear or branched $(C_1-C_6)$alkyl groups and all other symbols are as defined in claim 1.

6. The compound according to claim 1, wherein 'Z' is absent, 'Y' represents a bond and all other symbols are as defined in claim 1.

7. The compound according to claim 1, wherein 'Z' is absent, Y' is selected from oxygen, —NH, S, SO, $SO_2$ or $NR_4$ wherein $R_4$ represents, linear or branched $(C_1$-$C_6)$alkyl groups and all other symbols are as defined in claim 1.

8. The compound according to claim 1, wherein $R_1$ represents optionally substituted groups selected from linear or branched $(C_1$-$C_6)$alkyl, aralkyl, cycloalkyl, cycloalkylalkyl, heterocyclyl, heterocyclylalkyl, heteroaryl, heteroaralkyl groups and all other symbols are as defined in claim 1.

9. The compound according to claim 1, wherein $R_1$ represents the groups $C(O)OR_3$, $C(O)R_3$, and $SO_2R_3$ wherein $R_3$ represents optionally substituted groups selected from H, linear or branched $(C_1$-$C_6)$alkyl, aryl, aralkyl, cycloalkyl, cycloalkylalkyl, heterocyclyl, heterocyclylalkyl, heteroaryl, heteroaralkyl groups and all other symbols are as defined in claim 1.

10. The compound according to claim 1, wherein 'Z' is absent, $R_1$ represents optionally substituted groups selected from linear or branched $(C_1$-$C_6)$alkyl, aralkyl, cycloalkyl, cycloalkylalkyl, heterocyclyl, heterocyclylalkyl, heteroaryl, heteroaralkyl groups and all other symbols are as defined in claim 1.

11. The compound according to claim 1, wherein 'Z' is absent, $R_1$ represents the groups $C(O)OR_3$, $C(O)R_3$, and $SO_2R_3$ wherein $R_3$ represents optionally substituted groups selected from H, linear or branched $(C_1$-$C_6)$alkyl, aryl, aralkyl, cycloalkyl, cycloalkylalkyl, heterocyclyl, heterocyclylalkyl, heteroaryl, heteroaralkyl groups and all other symbols are as defined in claim 1.

12. The compound according to claim 1, wherein 'Z' represents optionally substituted single or fused group selected from aryl, heteroaryl, heterocyclyl, cycloalkyl groups, and $R_1$ represents optionally substituted groups selected from linear or branched $(C_1$-$C_6)$alkyl, aralkyl, cycloalkyl, cycloalkylalkyl, heterocyclyl, heterocyclylalkyl, heteroaryl, heteroaralkyl groups and all other symbols are as defined in claim 1.

13. The compound according to claim 1, wherein 'Z' represents optionally substituted single or fused group selected from aryl, heteroaryl, heterocyclyl, cycloalkyl groups and $R_1$ represents the groups $C(O)OR_3$, $C(O)R_3$, and $SO_2R_3$ wherein $R_3$ represents H, optionally substituted groups selected from linear or branched $(C_1$-$C_6)$alkyl, aryl, aralkyl, cycloalkyl, cycloalkylalkyl, heterocyclyl, heterocyclylalkyl, heteroaryl, heteroaralkyl groups and all other symbols are as defined in claim 1.

14. The compound according to claim 1, wherein 'Z' is absent, 'Y' is a bond and $R_1$ represents optionally substituted groups selected from linear or branched $(C_1$-$C_6)$alkyl, aralkyl, cycloalkyl, cycloalkylalkyl, heterocyclyl, heterocyclylalkyl, heteroaryl, heteroaralkyl groups and all other symbols are as defined in claim 1.

15. The compound according to claim 1, wherein 'Z' is absent, 'Y' is a bond and $R_1$ represents the groups $C(O)OR_3$, $C(O)R_3$, and $SO_2R_3$ wherein $R_3$ represents optionally substituted groups selected from H, linear or branched $(C_1$-$C_6)$ alkyl, aryl, aralkyl, cycloalkyl, cycloalkylalkyl, heterocyclyl, heterocyclylalkyl, heteroaryl, heteroaralkyl groups and all other symbols are as defined in claim 1.

16. The compound according to claim 1, wherein 'Z' is absent, 'Y' is selected from oxygen, —NH, S, SO, $SO_2$ or $NR_4$ wherein $R_4$ represents, linear or branched $(C_1$-$C_6)$alkyl groups and $R_1$ represents optionally substituted groups selected from linear or branched $(C_1$-$C_6)$alkyl, aralkyl, cycloalkyl, cycloalkylalkyl, heterocyclyl, heterocyclylalkyl, heteroaryl, heteroaralkyl groups and all other symbols are as defined in claim 1.

17. The compound according to claim 1, wherein 'Z' is absent, 'Y' is selected from oxygen, —NH, S, SO, $SO_2$ or $NR_4$, wherein $R_4$ represents, linear or branched $(C_1$-$C_6)$alkyl groups and $R_1$ represents the groups $C(O)OR_3$, $C(O)R_3$, and $SO_2R_3$ wherein $R_3$ represents H, optionally substituted groups selected from linear or branched $(C_1$-$C_6)$alkyl, aryl, aralkyl, cycloalkyl, cycloalkylalkyl, heterocyclyl, heterocyclylalkyl, heteroaryl, heteroaralkyl groups and all other symbols are as defined in claim 1.

18. The compound according to claim 1, wherein 'Y' is a bond and $R_1$ represents the groups $C(O)OR_3$, $C(O)R_3$, and $SO_2R_3$ wherein $R_3$ represents optionally substituted groups selected from H, linear or branched $(C_1$-$C_6)$alkyl, aryl, aralkyl, cycloalkyl, cycloalkylalkyl, heterocyclyl, heterocyclylalkyl, heteroaryl, heteroaralkyl groups and all other symbols are as defined in claim 1.

19. The compound according to claim 1, wherein 'Y' is selected from oxygen, —NH, S, SO, $SO_2$ or $NR_4$, wherein $R_4$ represents, linear or branched $(C_1$-$C_6)$alkyl groups and $R_1$ represents optionally substituted groups selected from linear or branched $(C_1$-$C_6)$alkyl, aralkyl, cycloalkyl, cycloalkylalkyl, heterocyclyl, heterocyclylalkyl, heteroaryl, heteroaralkyl groups and all other symbols are as defined in claim 1.

20. The compound of Formula (I) according to claim 1, wherein 'Z' represents a heteroaryl group.

21. The compound of Formula (I) according to claim 1, wherein 'Y' represents either a bond or oxygen atom.

22. The compound of Formula (I) according to claim 1, wherein $R_1$ represents a heteroaryl group or the group $C(O)OR_3$.

23. The compound of Formula (I) according to claim 1, wherein $R_3$ is selected from H, linear or branched $(C_1$-$C_6)$ alkyl, aryl, aralkyl group.

24. The compound of Formula (I) according to claim 1, wherein the substituents on 'Z' or '$R_1$' are independently selected from hydroxyl, oxo, halo, thio, nitro, amino, cyano, formyl, or substituted or unsubstituted groups selected from amidino, alkyl, haloalkyl, alkoxy, haloalkoxy, alkenyl, alkynyl, cycloalkyl, cycloalkenyl, bicycloalkyl, bicycloalkenyl, alkoxy, alkenoxy, cycloalkoxy, aryl, aryloxy, aralkyl, aralkoxy, heterocylyl, heteroaryl, heterocyclylalkyl, heteroaralkyl, heteroaryloxy, heteroaralkoxy, heterocyclyloxy, heterocyclylalkoxy, heterocyclylalkoxyacyl, acyl, acyloxy, acylamino, monosubstituted or disubstituted amino, arylamino, aralkylamino, carboxylic acid and its derivatives such as esters and amides, carbonylamino, hydroxyalkyl, aminoalkyl, alkoxyalkyl, aryloxyalkyl, aralkoxyalkyl, alkylthio, thioalkyl, arylthio, alkylsulfonylamino, alkylsulfonyloxy, alkoxycarbonylamino, aryloxycarbonylamino, aralkyloxycarbonylamino, aminocarbonylamino, alkylaminocarbonylamino, alkoxyamino, hydroxylamino, sulfenyl derivatives, sulfonyl derivatives, sulfonic acid and its derivatives, wherein each of these groups may independently be present one or more times either on 'Z' or '$R_1$'.

25. The compound of Formula (I) according to claim 1, wherein the substituents on 'Z' or '$R_1$' are independently selected from halo, thio, nitro, amino, cyano, or substituted or unsubstituted groups selected from alkyl, haloalkyl, alkoxy, haloalkoxy, aryl, aralkyl, sulfenyl derivatives, sulfonyl derivatives, sulfonic acid and its derivatives, wherein each of these groups may independently be present one or more times either on 'Z' or '$R_1$'.

26. A compound selected from the group consisting of:
cis-5-(4-((6-(4-(3-isopropyl-1,2,4-oxadiazol-5-yl)piperidin-1-yl)-5-nitropyrimidin-4-yl)oxy)phenyl)-1,3,2-dioxathiane 2-oxide;
trans-5-(4-((6-(4-(3-isopropyl-1,2,4-oxadiazol-5-yl)piperidin-1-yl)-5-nitropyrimidin-4-yl)oxy)phenyl)-1,3,2-dioxathiane 2-oxide;
cis-5-(4-((6-((1-(3-isopropyl-1,2,4-oxadiazol-5-yl)piperidin-4-yl)oxy)-5-methylpyrimidin-4-yl)oxy)phenyl)-1,3,2-dioxathiane 2-oxide;

trans-5-(4-(((6-((1-(3-isopropyl-1,2,4-oxadiazol-5-yl)piperidin-4-yl)oxy)-5-methylpyrimidin-4-yl)oxy)phenyl)-1,3,2-dioxathiane 2-oxide;

cis-5-(4-((5-methyl-6-((1-(pyrimidin-2-yl)piperidin-4-yl)oxy)pyrimidin-4-yl)oxy)phenyl)-1,3,2-dioxathiane 2-oxide;

trans 5-(4-((5-methyl-6-((1-(pyrimidin-2-yl)piperidin-4-yl)oxy)pyrimidin-4-yl)oxy)phenyl)-1,3,2-dioxathiane 2-oxide;

cis-5-(4-((2-(1-(pyrimidin-2-yl)piperidin-4-yl)thiazol-4-yl)methoxy)phenyl)-1,3,2-dioxathiane 2-oxide;

trans-5-(4-((2-(1-(pyrimidin-2-yl)piperidin-4-yl)thiazol-4-yl)methoxy)phenyl)-1,3,2-dioxathiane 2-oxide;

cis-5-(4-(((6-((1-(5-ethylpyrimidin-2-yl)piperidin-4-yl)oxy)-5-methylpyrimidin-4-yl)oxy)phenyl)-1,3,2-dioxathiane 2-oxide;

trans-5-(4-(((6-((1-(5-ethylpyrimidin-2-yl)piperidin-4-yl)oxy)-5-methylpyrimidin-4-yl)oxy)phenyl)-1,3,2-dioxathiane 2-oxide;

cis-5-(4-((6-(4-(3-isopropyl-1,2,4-oxadiazol-5-yl)piperidin-1-yl)-5-methylpyrimidin-4-yl)oxy)phenyl)-1,3,2-dioxathiane 2-oxide;

trans-5-(4-((6-(4-(3-isopropyl-1,2,4-oxadiazol-5-yl)piperidin-1-yl)-5-methylpyrimidin-4-yl)oxy)phenyl)-1,3,2-dioxathiane 2-oxide;

cis-5-(4-((2-((1-(5-ethylpyrimidin-2-yl)piperidin-4-yl)thiazol-4-yl)methoxy)phenyl)-1,3,2-dioxathiane 2-oxide;

trans-5-(4-((2-(1-(5-ethylpyrimidin-2-yl)piperidin-4-yl)thiazol-4-yl)methoxy)phenyl)-1,3,2-dioxathiane 2-oxide;

cis-tert-butyl 4-((5-methyl-6-(4-(2-oxido-1,3,2-dioxathian-5-yl)phenoxy)pyrimidin-4-yl)oxy)piperidine-1-carboxylate;

trans-tert-butyl 4-((5-methyl-6-(4-(2-oxido-1,3,2-dioxathian-5-yl)phenoxy)pyrimidin-4-yl)oxy)piperidine-1-carboxylate;

cis-tert-butyl 4-(4-((4-(2-oxido-1,3,2-dioxathian-5-yl)phenoxy)methyl)thiazol-2-yl)piperidine-1-carboxylate;

trans-tert-butyl 4-(4-((4-(2-oxido-1,3,2-dioxathian-5-yl)phenoxy)methyl)thiazol-2-yl)piperidine-1-carboxylate;

trans-tert-butyl 4-(2-(4-(2-oxido-1,3,2-dioxathian-5-yl)phenoxy)ethoxy)piperidine-1-carboxylate;

cis-tert-butyl 4-(3-((5-methyl-6-(4-(2-oxido-1,3,2-dioxathian-5-yl)phenoxy)pyrimidin-4-yl)oxy)propyl)piperidine-1-carboxylate;

trans-tert-butyl 4-(3-((5-methyl-6-(4-(2-oxido-1,3,2-dioxathian-5-yl)phenoxy)pyrimidin-4-yl)oxy)propyl)piperidine-1-carboxylate;

cis-5-(4-(3-((1-(pyrimidin-2-yl)piperidin-4-yl)oxy)propoxy)phenyl)-1,3,2-dioxathiane 2-oxide;

trans-5-(4-(3-((1-(pyrimidin-2-yl)piperidin-4-yl)oxy)propoxy)phenyl)-1,3,2-dioxathiane 2-oxide;

cis-tert-butyl 4-((5-methyl-6-(4-((2-oxido-1,3,2-dioxathian-5-yl)methyl)phenoxy)pyrimidin-4-yl)oxy)piperidine-1-carboxylate;

trans-tert-butyl 4-((5-methyl-6-(4-((2-oxido-1,3,2-dioxathian-5-yl)methyl)phenoxy)pyrimidin-4-yl)oxy)piperidine-1-carboxylate;

tert-butyl 4-((5-methyl-6-(4-((2-oxido-1,3,2-dioxathiolan-4-yl)methyl)phenoxy)pyrimidin-4-yl)oxy)piperidine-1-carboxylate;

cis-isobutyl 4-((5-methyl-6-(4-(2-oxido-1,3,2-dioxathian-5-yl)phenoxy)pyrimidin-4-yl)oxy)piperidine-1-carboxylate;

trans-isobutyl 4-((5-methyl-6-(4-(2-oxido-1,3,2-dioxathian-5-yl)phenoxy)pyrimidin-4-yl)oxy)piperidine-1-carboxylate;

cis-5-(4-(((6-((1-(3-isopropyl-1,2,4-oxadiazol-5-yl)piperidin-4-yl)oxy)-5-methylpyrimidin-4-yl)oxy)benzyl)-1,3,2-dioxathiane 2-oxide;

trans-5-(4-(((6-((1-(3-isopropyl-1,2,4-oxadiazol-5-yl)piperidin-4-yl)oxy)-5-methylpyrimidin-4-yl)oxy)benzyl)-1,3,2-dioxathiane 2-oxide;

cis-5-(4-(((6-((1-(5-ethylpyrimidin-2-yl)piperidin-4-yl)oxy)-5-methylpyrimidin-4-yl)oxy)benzyl)-1,3,2-dioxathiane 2-oxide;

trans-5-(4-(((6-((1-(5-ethylpyrimidin-2-yl)piperidin-4-yl)oxy)-5-methylpyrimidin-4-yl)oxy)benzyl)-1,3,2-dioxathiane 2-oxide;

cis-ethyl 4-((5-methyl-6-(4-(2-oxido-1,3,2-dioxathian-5-yl)phenoxy)pyrimidin-4-yl)oxy)piperidine-1-carboxylate;

trans-ethyl 4-((5-methyl-6-(4-(2-oxido-1,3,2-dioxathian-5-yl)phenoxy)pyrimidin-4-yl)oxy)piperidine-1-carboxylate;

cis-benzyl 4-((5-methyl-6-(4-(2-oxido-1,3,2-dioxathian-5-yl)phenoxy)pyrimidin-4-yl)oxy)piperidine-1-carboxylate;

trans-benzyl 4-((5-methyl-6-(4-(2-oxido-1,3,2-dioxathian-5-yl)phenoxy)pyrimidin-4-yl)oxy)piperidine-1-carboxylate;

cis-5-(4-(((6-((1-benzylpiperidin-4-yl)oxy)-5-methylpyrimidin-4-yl)oxy)phenyl)-1,3,2-dioxathiane 2-oxide;

trans-5-(4-(((6-((1-benzylpiperidin-4-yl)oxy)-5-methylpyrimidin-4-yl)oxy)phenyl)-1,3,2-dioxathiane 2-oxide;

cis-ethyl 4-((5-methyl-6-(4-((2-oxido-1,3,2-dioxathian-5-yl)methyl)phenoxy)pyrimidin-4-yl)oxy)piperidine-1-carboxylate;

trans-ethyl 4-((5-methyl-6-(4-((2-oxido-1,3,2-dioxathian-5-yl)methyl)phenoxy)pyrimidin-4-yl)oxy)piperidine-1-carboxylate;

cis-5-(4-((5-methyl-6-((1-(pyrimidin-2-yl)piperidin-4-yl)oxy)pyrimidin-4-yl)oxy)benzyl)-1,3,2-dioxathiane 2-oxide;

trans-5-(4-((5-methyl-6-((1-(pyrimidin-2-yl)piperidin-4-yl)oxy)pyrimidin-4-yl)oxy)benzyl)-1,3,2-dioxathiane 2-oxide;

cis-isobutyl 4-((5-methyl-6-(4-((2-oxido-1,3,2-dioxathian-5-yl)methyl)phenoxy)pyrimidin-4-yl)oxy)piperidine-1-carboxylate;

trans-isobutyl 4-((5-methyl-6-(4-((2-oxido-1,3,2-dioxathian-5-yl)methyl)phenoxy)pyrimidin-4-yl)oxy)piperidine-1-carboxylate;

cis-N-(2,4-dichlorophenyl)-4-((5-methyl-6-(4-(2-oxido-1,3,2-dioxathian-5-yl)phenoxy)pyrimidin-4-yl)oxy)piperidine-1-carboxamide;

trans-N-(2,4-dichlorophenyl)-4-((5-methyl-6-(4-(2-oxido-1,3,2-dioxathian-5-yl)phenoxy)pyrimidin-4-yl)oxy)piperidine-1-carboxamide;

cis-isopropyl 4-((5-methyl-6-(4-(2-oxido-1,3,2-dioxathian-5-yl)phenoxy)pyrimidin-4-yl)oxy)piperidine-1-carboxylate;

trans-isopropyl 4-((5-methyl-6-(4-(2-oxido-1,3,2-dioxathian-5-yl)phenoxy)pyrimidin-4-yl)oxy)piperidine-1-carboxylate;

cis-isopropyl 4-((5-methyl-6-(4-((2-oxido-1,3,2-dioxathian-5-yl)methyl)phenoxy)pyrimidin-4-yl)oxy)piperidine-1-carboxylate;

trans-isopropyl 4-((5-methyl-6-(4-((2-oxido-1,3,2-dioxathian-5-yl)methyl)phenoxy)pyrimidin-4-yl)oxy)piperidine-1-carboxylate;

cis-tert-butyl 4-(4-((2-oxido-1,3,2-dioxathian-5-yl)methyl)phenoxy)piperidine-1-carboxylate;
trans-tert-butyl 4-(4-((2-oxido-1,3,2-dioxathian-5-yl)methyl)phenoxy)piperidine-1-carboxylate;
cis-5-(4-((1-(3-isopropyl-1,2,4-oxadiazol-5-yl)piperidin-4-yl)oxy)benzyl)-1,3,2-dioxathiane 2-oxide;
trans-5-(4-((1-(3-isopropyl-1,2,4-oxadiazol-5-yl)piperidin-4-yl)oxy)benzyl)-1,3,2-dioxathiane 2-oxide;
cis-tert-butyl 4-(4-((4-((2-oxido-1,3,2-dioxathian-5-yl)methyl)phenoxy)methyl)thiazol-2-yl)piperidine-1-carboxylate;
trans-tert-butyl 4-(4-((4-((2-oxido-1,3,2-dioxathian-5-yl)methyl)phenoxy)methyl)thiazol-2-yl)piperidine-1-carboxylate;
cis-tert-butyl 4-(2-methoxy-4-((2-oxido-1,3,2-dioxathian-5-yl)methyl)phenoxy)piperidine-1-carboxylate;
trans-tert-butyl 4-(2-methoxy-4-((2-oxido-1,3,2-dioxathian-5-yl)methyl)phenoxy)piperidine-1-carboxylate;
cis-5-(4-((1-(5-ethylpyrimidin-2-yl)piperidin-4-yl)oxy)benzyl)-1,3,2-dioxathiane 2-oxide;
trans-5-(4-((1-(5-ethylpyrimidin-2-yl)piperidin-4-yl)oxy)benzyl)-1,3,2-dioxathiane 2-oxide;
cis-5-(3-chloro-4-((6-((1-(3-isopropyl-1,2,4-oxadiazol-5-yl)piperidin-4-yl)oxy)-5-methylpyrimidin-4-yl)oxy)benzyl)-1,3,2-dioxathiane 2-oxide;
trans-5-(3-chloro-4-((6-((1-(3-isopropyl-1,2,4-oxadiazol-5-yl)piperidin-4-yl)oxy)-5-methylpyrimidin-4-yl)oxy)benzyl)-1,3,2-dioxathiane 2-oxide;
cis-tart-butyl 4-((6-(2-chloro-4-((2-oxido-1,3,2-dioxathian-5-yl)methyl)phenoxy)-5-methylpyrimidin-4-yl)oxy)piperidine-1-carboxylate;
trans-tert-butyl 4-((6-(2-chloro-4-((2-oxido-1,3,2-dioxathian-5-yl)methyl)phenoxy)-5-methylpyrimidin-4-yl)oxy)piperidine-1-carboxylate;
cis-isobutyl 4-((6-(2-chloro-4-(2-oxido-1,3,2-dioxathian-5-yl)phenoxy)-5-methylpyrimidin-4-yl)oxy)piperidine-1-carboxylate;
trans-isobutyl 4-((6-(2-chloro-4-(2-oxido-1,3,2-dioxathian-5-yl)phenoxy)-5-methylpyrimidin-4-yl)oxy)piperidine-1-carboxylate;
cis-isobutyl 4-((6-(2-chloro-4-((2-oxido-1,3,2-dioxathian-5-yl)methyl)phenoxy)-5-methylpyrimidin-4-yl)oxy)piperidine-1-carboxylate;
trans-isobutyl 4-((6-(2-chloro-4-((2-oxido-1,3,2-dioxathian-5-yl)methyl)phenoxy)-5-methylpyrimidin-4-yl)oxy)piperidine-1-carboxylate;
cis-isobutyl 4-((6-(2-methoxy-4-((2-oxido-1,3,2-dioxathian-5-yl)methyl)phenoxy)-5-methylpyrimidin-4-yl)oxy)piperidine-1-carboxylate;
trans-isobutyl 4-((6-(2-methoxy-4-((2-oxido-1,3,2-dioxathian-5-yl)methyl)phenoxy)-5-methylpyrimidin-4-yl)oxy)piperidine-1-carboxylate;
cis-tert-butyl 4-((6-(2-methoxy-4-((2-oxido-1,3,2-dioxathian-5-yl)methyl)phenoxy)-5-methylpyrimidin-4-yl)oxy)piperidine-1-carboxylate;
trans-tert-butyl 4-((6-(2-methoxy-4-((2-oxido-1,3,2-dioxathian-5-yl)methyl)phenoxy)-5-methylpyrimidin-4-yl)oxy)piperidine-1-carboxylate;
cis-5-(4-((6-((1-(3-isopropyl-1,2,4-oxadiazol-5-yl)piperidin-4-yl)oxy)-5-methylpyrimidin-4-yl)oxy)-3-methoxybenzyl)-1,3,2-dioxathiane 2-oxide;
trans-5-(4-((6-((1-(3-isopropyl-1,2,4-oxadiazol-5-yl)piperidin-4-yl)oxy)-5-methylpyrimidin-4-yl)oxy)-3-methoxybenzyl)-1,3,2-dioxathiane 2-oxide;
cis-tert-butyl 4-((5-methyl-6-((6-((2-oxido-1,3,2-dioxathian-5-yl)methyl)pyridin-3-yl)oxy)pyrimidin-4-yl)oxy)piperidine-1-carboxylate;
trans-tert-butyl 4-((5-methyl-6-((6-((2-oxido-1,3,2-dioxathian-5-yl)methyl)pyridin-3-yl)oxy)pyrimidin-4-yl)oxy)piperidine-1-carboxylate;
cis-tert-butyl 4-((6-(4-(2-oxido-1,3,2-dioxathian-5-yl)phenoxy)pyrimidin-4-yl)oxy)piperidine-1-carboxylate;
trans-tert-butyl 4-((6-(4-(2-oxido-1,3,2-dioxathian-5-yl)phenoxy)pyrimidin-4-yl)oxy)piperidine-1-carboxylate;
cis-tert-butyl 4-(4-((4-(2-oxido-1,3,2-dioxathian-5-yl)phenoxy)methyl)phenoxy)piperidine-1-carboxylate;
cis-tert-butyl 4-(4-((4-((2-oxido-1,3,2-dioxathian-5-yl)methyl)phenoxy)methyl)phenoxy)piperidine-1-carboxylate;
isobutyl 4-((6-(4-(2,2-dioxido-1,3,2-dioxathian-5-yl)phenoxy)-5-methylpyrimidin-4-yl)oxy)piperidine-1-carboxylate;
5-(4-((6-((1-(3-isopropyl-1,2,4-oxadiazol-5-yl)piperidin-4-yl)oxy)-5-methylpyrimidin-4-yl)oxy)phenyl)-1,3,2-dioxathiane 2,2-dioxide;
isobutyl 4-((6-(4-((2,2-dioxido-1,3,2-dioxathian-5-yl)methyl)phenoxy)-5-methylpyrimidin-4-yl)oxy)piperidine-1-carboxylate;
5-(4-((6-((1-(5-ethylpyrimidin-2-yl)piperidin-4-yl)oxy)-5-methylpyrimidin-4-yl)oxy)benzyl)-1,3,2-dioxathiane 2,2-dioxide;
5-(4-((6-(4-(3-isopropyl-1,2,4-oxadiazol-5-yl)piperidin-1-yl)-5-nitropyrimidin-4-yl)oxy)phenyl)-1,3,2-dioxathiane 2,2-dioxide;
5-(4-((5-methyl-6-((1-(pyrimidin-2-yl)piperidin-4-yl)oxy)pyrimidin-4-yl)oxy)phenyl)-1,3,2-dioxathiane 2,2-dioxide;
5-(4-((6-((1-(5-ethylpyrimidin-2-yl)piperidin-4-yl)oxy)-5-methylpyrimidin-4-yl)oxy)phenyl)-1,3,2-dioxathiane 2,2-dioxide;
5-(4-((2-(1-(pyrimidin-2-yl)piperidin-4-yl)thiazol-4-yl)methoxy)phenyl)-1,3,2-dioxathiane 2,2-dioxide;
5-(4-((6-(4-(3-isopropyl-1,2,4-oxadiazol-5-yl)piperidin-1-yl)-5-methylpyrimidin-4-yl)oxy)phenyl)-1,3,2-dioxathiane 2,2-dioxide;
5-(4-((2-(1-(5-ethylpyrimidin-2-yl)piperidin-4-yl)thiazol-4-yl)methoxy)phenyl)-1,3,2-dioxathiane 2,2-dioxide;
tert-butyl 4-((6-(4-(2,2-dioxido-1,3,2-dioxathian-5-yl)phenoxy)-5-methylpyrimidin-4-yl)oxy)piperidine-1-carboxylate;
tert-butyl 4-(2-(4-(2,2-dioxido-1,3,2-dioxathian-5-yl)phenoxy)ethoxy)piperidine-1-carboxylate;
tert-butyl 4-(3-((6-(4-(2,2-dioxido-1,3,2-dioxathian-5-yl)phenoxy)-5-methylpyrimidin-4-yl)oxy)propyl)piperidine-1-carboxylate;
5-(4-(2-((1-(pyrimidin-2-yl)piperidin-4-yl)oxy)ethoxy)phenyl)-1,3,2-dioxathiane 2,2-dioxide;
5-(4-(2-((1-(5-ethylpyrimidin-2-yl)piperidin-4-yl)oxy)ethoxy)phenyl)-1,3,2-dioxathiane 2,2-dioxide;
5-(4-(2-((1-(3-isopropyl-1,2,4-oxadiazol-5-yl)piperidin-4-yl)oxy)ethoxy)phenyl)-1,3,2-dioxathiane 2,2-dioxide;
tert-butyl 4-((6-(4-((2,2-dioxido-1,3,2-dioxathian-5-yl)methyl)phenoxy)-5-methylpyrimidin-4-yl)oxy)piperidine-1-carboxylate;
tert-butyl 4-((6-(4-(2,2-dioxido-1,3,2-dioxathiolan-4-yl)phenoxy)-5-methylpyrimidin-4-yl)oxy)piperidine-1-carboxylate;
5-(4-((6-((1-(3-isopropyl-1,2,4-oxadiazol-5-yl)piperidin-4-yl)oxy)-5-methylpyrimidin-4-yl)oxy)benzyl)-1,3,2-dioxathiane 2,2-dioxide;
ethyl 4-((6-(4-(2,2-dioxido-1,3,2-dioxathian-5-yl)phenoxy)-5-methylpyrimidin-4-yl)oxy)piperidine-1-carboxylate;

benzyl 4-((6-(4-(2,2-dioxido-1,3,2-dioxathian-5-yl)phenoxy)-5-methylpyrimidin-4-yl)oxy)piperidine-1-carboxylate;

5-(4-((6-((1-benzylpiperidin-4-yl)oxy)-5-methylpyrimidin-4-yl)oxy)phenyl)-1,3,2-dioxathiane 2,2-dioxide;

ethyl 4-((6-(4-((2,2-dioxido-1,3,2-dioxathian-5-yl)methyl)phenoxy)-5-methylpyrimidin-4-yl)oxy)piperidine-1-carboxylate;

5-(4-((5-methyl-6-((1-(pyrimidin-2-yl)piperidin-4-yl)oxy)pyrimidin-4-yl)oxy)benzyl)-1,3,2-dioxathiane 2,2-dioxide;

N-(2,4-dichlorophenyl)-4-((6-(4-(2,2-dioxido-1,3,2-dioxathian-5-yl)phenoxy)-5-methylpyrimidin-4-yl)oxy)piperidine-1-carboxamide;

isopropyl 4-((6-(4-(2,2-dioxido-1,3,2-dioxathian-5-yl)phenoxy)-5-methylpyrimidin-4-yl)oxy)piperidine-1-carboxylate;

isopropyl 4-((6-(4-((2,2-dioxido-1,3,2-dioxathian-5-yl)methyl)phenoxy)-5-methylpyrimidin-4-yl)oxy)piperidine-1-carboxylate;

tert-butyl 4-(4-((2,2-dioxido-1,3,2-dioxathian-5-yl)methyl)phenoxy)piperidine-1-carboxylate;

5-(4-((1-(3-isopropyl-1,2,4-oxadiazol-5-yl)piperidin-4-yl)oxy)benzyl)-1,3,2-dioxathiane 2,2-dioxide;

tert-butyl 4-(4-((4-((2,2-dioxido-1,3,2-dioxathian-5-yl)methyl)phenoxy)methyl)thiazol-2-yl)piperidine-1-carboxylate;

5-(4-((1-(5-ethylpyrimidin-2-yl)piperidin-4-yl)oxy)benzyl)-1,3,2-dioxathiane 2,2-dioxide;

5-(3-chloro-4-((6-((1-(3-isopropyl-1,2,4-oxadiazol-5-yl)piperidin-4-yl)oxy)-5-methylpyrimidin-4-yl)oxy)benzyl)-1,3,2-dioxathiane 2,2-dioxide;

tert-butyl 4-((6-(2-chloro-4-((2,2-dioxido-1,3,2-dioxathian-5-yl)methyl)phenoxy)-5-methylpyrimidin-4-yl)oxy)piperidine-1-carboxylate;

isobutyl 4-((6-(2-chloro-4-(2,2-dioxido-1,3,2-dioxathian-5-yl)phenoxy)-5-methylpyrimidin-4-yl)oxy)piperidine-1-carboxylate;

isobutyl 4-((6-(2-chloro-4-((2,2-dioxido-1,3,2-dioxathian-5-yl)methyl)phenoxy)-5-methylpyrimidin-4-yl)oxy)piperidine-1-carboxylate;

isobutyl 4-((6-(4-((2,2-dioxido-1,3,2-dioxathian-5-yl)methyl)-2-methoxyphenoxy)-5-methylpyrimidin-4-yl)oxy)piperidine-1-carboxylate;

tert-butyl 4-((6-(4-((2,2-dioxido-1,3,2-dioxathian-5-yl)methyl)-2-methoxyphenoxy)-5-methylpyrimidin-4-yl)oxy)piperidine-1-carboxylate;

5-(4-((6-((1-(3-isopropyl-1,2,4-oxadiazol-5-yl)piperidin-4-yl)oxy)-5-methylpyrimidin-4-yl)oxy)-3-methoxybenzyl)-1,3,2-dioxathiane 2,2-dioxide;

tert-butyl 4-((6-((6-((2,2-dioxido-1,3,2-dioxathian-5-yl)methyl)pyridin-3-yl)oxy)-5-methylpyrimidin-4-yl)oxy)piperidine-1-carboxylate;

tert-butyl 4-((6-(4-(2,2-dioxido-1,3,2-dioxathian-5-yl)phenoxy)pyrimidin-4-yl)oxy)piperidine-1-carboxylate;

tert-butyl 4-(4-((4-((2,2-dioxido-1,3,2-dioxathian-5-yl)methyl)phenoxy)methyl)phenoxy)piperidine-1-carboxylate;

tert-butyl 4-(4-((4-(2,2-dioxido-1,3,2-dioxathian-5-yl)phenoxy)methyl)phenoxy)piperidine-1-carboxylate;

tert-butyl 4-(4-((2,2-dioxido-1,3,2-dioxathian-5-yl)methyl)-2-methoxyphenoxy)piperidine-1-carboxylate;

tert-butyl 4-(4-((4-(2,2-dioxido-1,3,2-dioxathian-5-yl)phenoxy)methyl)thiazol-2-yl)piperidine-1-carboxylate;

tert-butyl 4-((6-(4-((2,2-dioxido-1,3,2-dioxathiolan-4-yl)methyl)phenoxy)-5-methylpyrimidin-4-yl)oxy)piperidine-1-carboxylate;

5-(4-(3-(1-(pyrimidin-2-yl)piperidin-4-yl)propoxy)phenyl)-1,3,2-dioxathiane 2,2-dioxide.

27. A pharmaceutical composition comprising a compound of Formula (I) as defined in claim 1 and optionally one or more pharmaceutically acceptable carriers, excipients or diluents.

28. A method for treating diabetes, comprising the step of providing the compound of formula (I) as defined in claim 1 or its suitable pharmaceutical compositions to a patient in need of such treatment.

29. A process for preparing compounds of Formula (I) as defined in claim 1, the process comprising the steps of:
i) reacting a compound of Formula (V) with thionyl chloride in one or more suitable solvents to obtain compounds of Formula (Ia), wherein each of the terms are as defined in claim 1

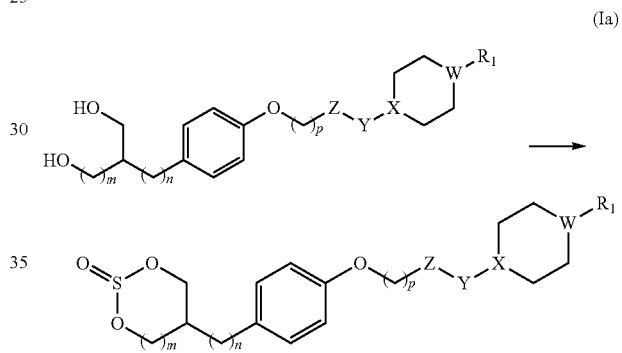

ii) and converting the compound of Formula (Ia) to compounds of Formula (I) by oxidizing with suitable oxidizing agents, wherein all the terms are as defined in claim 1

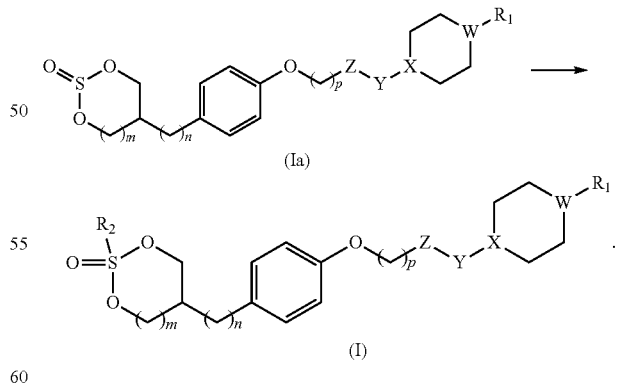

* * * * *